(12) United States Patent
Kisiel et al.

(10) Patent No.: US 7,585,842 B2
(45) Date of Patent: Sep. 8, 2009

(54) HUMAN KUNITZ-TYPE INHIBITOR WITH ENHANCED ANTIFIBRINOLYTIC ACTIVITY

(75) Inventors: Walter Kisiel, Albuquerque, NM (US); Hitendra S. Chand, Albuquerque, NM (US); S. Paul Bajaj, Los Angeles, CA (US)

(73) Assignee: The Reagents of the University of California, Oakland, CA (US)

( * ) Notice: Subject to any disclaimer, the term of this patent is extended or adjusted under 35 U.S.C. 154(b) by 160 days.

(21) Appl. No.: 11/646,776

(22) Filed: Dec. 28, 2006

(65) Prior Publication Data

US 2008/0026998 A1    Jan. 31, 2008

Related U.S. Application Data

(63) Continuation-in-part of application No. 11/107,643, filed on Apr. 15, 2005, now Pat. No. 7,432,238.

(60) Provisional application No. 60/754,913, filed on Dec. 29, 2005, provisional application No. 60/563,039, filed on Apr. 16, 2004.

(51) Int. Cl.
   *A61K 38/00* (2006.01)
(52) U.S. Cl. ......................................... 514/12; 530/350
(58) Field of Classification Search ................... 514/12; 530/350
   See application file for complete search history.

(56) References Cited

OTHER PUBLICATIONS

Seq ID No. 2 and AC 035536 & Seq ID No. 3 and AC 035536.*

* cited by examiner

*Primary Examiner*—Tekchand Saidha
(74) *Attorney, Agent, or Firm*—Ballard Spahr Andrews & Ingersoll, LLP

(57) ABSTRACT

A human Kunitz-type inhibitor polypeptide with enhanced antifibrinolytic activity, methods of making, and methods of use. The novel polypeptide is structurally similar to the KD1 domain of human tissue factor pathway inhibitor-2 (TFPI-2).

23 Claims, 15 Drawing Sheets
(3 of 15 Drawing Sheet(s) Filed in Color)

Human Tissue Factor Pathway Inhibitor-2

Wild-type TFPI-2 KD1

R24K TFPI-2 KD1

| Inhibitor | NH$_2$---P$_6$ | P$_5$ | P$_4$ | P$_3$ | P$_2$ | P$_1$ | P$_1'$ | P$_2'$ | P$_3'$ | P$_4'$ | P$_5'$--------P$_{18}'$-COOH |
|---|---|---|---|---|---|---|---|---|---|---|---|
| BPTI | --- | Y | T | G | P | C | K | A | R | I | I | R---------F--- |
| APPI | --- | E | T | G | P | C | R | A | M | I | I | R---------F--- |
| APPH | --- | M | T | G | P | C | R | A | V | M | P | R---------F--- |
| TFPI Domain 1 | --- | D | D | G | P | C | K | A | I | M | K | R---------F--- |
| TFPI Domain 2 | --- | D | P | G | I | C | R | G | Y | I | T | R---------F--- |
| TFPI Domain 3 | --- | D | L | G | L | C | R | A | N | E | N | R---------F--- |
| TFPI-2 Domain 1 | --- | D | Y | G | P | C | R | A | L | L | L | R---------F--- |
| TFPI-2 Domain 2 | --- | V | D | D | Q | C | E | G | S | T | E | K---------F--- |
| TFPI-2 Domain 3 | --- | D | E | G | L | C | S | A | N | V | T | R---------F--- |
| HAI-1 Domain 1 | --- | K | V | G | R | C | R | G | S | F | P | R---------F--- |
| HAI-1 Domain 2 | --- | D | T | G | L | C | K | E | S | I | P | R---------F--- |
| HAI-2 Domain 1 | --- | V | V | G | R | C | R | A | S | M | P | R---------F--- |
| HAI-2 Domain 2 | --- | V | T | G | P | C | R | A | S | F | P | R---------F--- |
| IαTI | --- | S | A | G | P | C | M | G | M | T | S | R---------F--- |
| PLI | --- | Y | T | G | P | C | K | A | R | M | I | K---------F--- |
| UPTI | --- | Y | T | G | P | C | R | A | H | F | I | R---------F--- |
| SPI 1 | --- | K | T | G | P | C | K | A | A | F | Q | R---------F--- |
| AsKC-1 | --- | D | V | G | R | C | R | A | S | H | P | R---------F--- |

Figure 4

```
              5         10        15        20        25        30        35        40        45        50        55
              .         .         .         .         .         .         .         .         .         .         .
BPTI   R P D F C L E P P Y T G P C K A R I I R Y F Y N A K A G L C Q T F V Y G G C R A K R N N F K S A E D C M R T C G G A
KD-1   N A E I C L L P L D Y G P C R A L L L R Y Y Y D R Y T Q S C R Q F L Y G G C E G N A N N F Y T W E A C D D A C W R I
```

HUMAN KUNITZ-TYPE INHIBITOR WITH ENHANCED ANTIFIBRINOLYTIC ACTIVITY

This application claims the benefit of U.S. Provisional Application Ser. No. 60/754,913, filed Dec. 29, 2005, and is a continuation-in-part of U.S. patent application Ser. No. 11/107,643, filed Apr. 15, 2005, now U.S. Pat. No. 7,432,238, which claims the benefit of U.S. Provisional Application Ser. No. 60/563,039, filed Apr. 16, 2004, each of which is incorporated herein by reference in its entirety.

STATEMENT OF GOVERNMENT RIGHTS

This invention was made with government support under a grant from the National Institutes of Health, Grant No. HL 64119 and National Institutes of Health Grants HL 70369 (PB) and HL 36365 (PB). The U.S. Government has certain rights in this invention.

BACKGROUND OF THE INVENTION

Proteinase inhibitors play a critical role in the regulation of several physiological processes such as blood coagulation, complement fixation, fibrinolysis, and fertilization (Bode and Huber, *Biochim. Biophys. Acta* 1477:241-252, 2000). Most of these inhibitors are proteins having characteristic polypeptide scaffolds, and are grouped into a number of families including the Kunitz (Laskowski and Kato, *Ann. Rev. Biochem.* 49: 593-626, 1980), Kazal (Laskowski and Kato, *Ann. Rev. Biochem.* 49: 593-626, 1980), Serpin (Potempa et al., *J. Biol. Chem.* 269: 15957-159, 60, 1994) and mucus (Wiedow et al., *J. Biol. Chem.* 265: 14791-14795, 1990) families.

The Kunitz-type family comprises serine proteinase inhibitors that include one or more Kunitz-type inhibitory domains. Bovine pancreatic trypsin inhibitor (BPTI) is the prototypical Kunitz-type inhibitor. The Kunitz-type family also includes tissue factor pathway inhibitor (TFPI) and type-2 tissue factor pathway inhibitor (TFPI-2). These two inhibitors have been investigated extensively in the past decade, and have been shown to play an important role in inhibiting serine proteinases involved in coagulation and fibrinolysis (Girard et al., *Nature* 338:518-520, 1989; Broze et al., *Biochemistry* 29: 7539-7546, 1990; Sprecher et al., *Proc. Natl. Acad. Sci. USA* 91: 3353-3357, 1994; Bajaj et al., *Thromb. Haemost.* 86:959-972, 2001).

Human TFPI-2, originally isolated from placenta and designated as placental protein 5 (PP5), is a matrix-associated inhibitor consisting of three tandemly arranged Kunitz-type proteinase inhibitor domains flanked by a short acidic amino terminus and a highly basic carboxy-terminal tail (Sprecher et al., *Proc. Natl. Acad. Sci. USA* 91:3353-3357, 1994; Miyagi et al., *J. Biochem.* 116:939-942, 1994) (see FIG. 1). A wide variety of cells including keratinocytes (Rao et al., *J. Invest. Dermatol.* 104: 379-383, 1995), dermal fibroblasts (Rao et al. *J. Invest. Dermatol.* 104: 379-383, 1995), smooth muscle cells (Herman et al. *J. Clin. Invest.* 107: 1117-1126, 2001), syncytiotrophoblasts (Udagawa et al. *Placenta* 19:217-223, 1998), synoviocytes (Sugiyama et al. *FEBS Lett.* 517: 121-128, 2002), and endothelial cells (Iino et al. *Arterioscler. Thromb. Vasc. Biol.* 18: 40-46, 1998) synthesize and secrete TFPI-2, primarily into their extracellular matrix. Three variants/isoforms of molecular mass 32 kDa, 30 kDa and 27 kDa are synthesized by these cells and are thought to represent differentially glycosylated forms (Rao et al., *Arch. Biochem. Biophys.* 335:45-52, 1996).

TFPI-2 exhibits inhibitory activity towards a broad spectrum of proteinases including trypsin, plasmin, chymotrypsin, cathepsin G, plasma kallikrein and the factor VIIa-tissue factor complex. However, TFPI-2 exhibits little, if any, inhibitory activity towards urokinase-type plasminogen activator (uPA), tissue-type plasminogen activator (tPA) and α-thrombin (Petersen et al., *Biochemistry* 35: 266-272, 1996). TFPI-2 presumably inhibits proteinases through a $P_1$ arginine residue (R24) in its Kunitz-type domain, since an R24Q TFPI-2 mutant exhibited only 5-10% inhibitory activity toward trypsin, plasmin and the factor VIIa-tissue factor complex (Kamei et al. *Thromb. Res.* 94: 147-152, 1999). Recently, TFPI-2 expression by a stably-transfected human high-grade glioma cell line SNB19 resulted in a diminished capacity to form tumors relative to their parental control or mock-transfected SNB19 cells following intracerebral injection of these cells into mice (Konduri et. al., *Oncogene* 20:6938-6945, 2001). This latter study provides strong experimental evidence that down-regulation of TFPI-2 by tumor cells, presumably through hypermethylation of the TFPI-2 promoter, plays a significant role in the invasive properties of human gliomas.

Plasmin is known to degrade fibrinogen after surgery. Bovine pancreatic trypsin inhibitor (BPTI), also known commercially as aprotinin or Trasylol® (commercially available from Bayer Corporation, West Haven, Conn.), is widely used in the clinic post-operatively by anesthesiologists for general surgery patients and patients undergoing cardiopulmonary bypass surgery to inhibit the degradation of fibrinogen (fibrinolysis) by plasmin arising through activation of the fibrinolytic pathway. Aprotinin inhibits the activity of plasmin. However, aprotinin, being of bovine origin, precipitates episodes of severe anaphylaxis on some occasions (0.5-1%). Accordingly, there is still a need in the art for improved formulations having antifibrinolytic activity that does not produce the undesirable side effects associated with traditional antifibrinolytic compositions.

SUMMARY OF THE INVENTION

The present invention provides a "KD1 polypeptide" that is structurally equivalent to or structurally similar to the primary structure of the KD1 domain of Kunitz inhibitor human type 2 tissue factor pathway inhibitor (TFPI-2) (SEQ ID NO:2), as well as methods for making and using a KD1 polypeptide.

In one embodiment, the KD1 polypeptide consists essentially of a primary structure that is equivalent to the primary structure of the wild-type KD1 domain of human tissue factor pathway inhibitor-2 (TFPI-2) (SEQ ID NO:2). In another embodiment, the KD1 polypeptide consists essentially of a primary structure that is similar to the primary structure of the wild-type KD1 domain of human tissue factor pathway inhibitor-2 (TFPI-2) (SEQ ID NO:2), preferably with the proviso that said polypeptide includes a lysine instead of arginine at position 24 (R24K) as defined for the wild-type KD1 amino acid sequence. In a preferred embodiment, the KD1 polypeptide consists essentially of the primary structure of the wild-type KD1 domain of TFPI-2 (SEQ ID NO:2), or a biologically active subunit thereof, with the proviso that said polypeptide includes a lysine instead of arginine at position 24 (R24K) as defined for the wild-type KD1 amino acid sequence; more preferably, the KD1 polypeptide comprises SEQ ID NO:3. A biologically active subunit of KD1 is characterized by deletions of 1, 2, 3, 4, 5, 6, 7, 8, 9, or 10 amino acid residues at either or both of the amino-terminal or carboxy-terminal end relative to the wild-type KD1 sequence.

In another embodiment, the KD1 polypeptide is a "double mutant" KD1 polypeptide or a "multiple mutant" KD1 polypeptide. The term "multiple mutant" is inclusive of the term "double mutant" and signifies a plurality of mutations (i.e., two or more) relative to the wild-type KD1 sequence. The multiple mutant KD1 polypeptide consists essentially of a primary structure that is similar to, and in some embodiments equivalent to, the primary structure of the wild-type KD1 domain of human tissue factor pathway inhibitor-2 (TFPI-2) (SEQ ID NO:2), or a biologically active subunit thereof, with the proviso that the polypeptide includes a lysine instead of arginine at position 24 (R24K) together with at least one of the following additional changes (mutations) with respect to the wild-type KD1 domain primary structure: an arginine instead of a leucine at position 26 (L26R); a threonine instead of a tyrosine at position 20 (Y20T); a glutamate or a tyrosine instead of an aspartate at position 19 (D19E or D19Y); and/or a glutamate or a lysine instead of a tyrosine at position 55 (Y55E or Y55K). The amino acid numbering is as defined for the wild-type KD1 amino acid sequence.

In another embodiment, the KD1 polypeptide consists essentially of a primary structure that is equivalent to or similar to the primary structure of the wild-type KD1 domain of TFPI-2 (SEQ ID NO:2), or a biologically active subunit thereof, with the proviso that said polypeptide includes at least one conservative amino acid substitution relative to the primary structure of the wild-type KD1 domain of TFPI-2, and preferably with the further proviso that said polypeptide includes a lysine instead of arginine at position 24 as defined for the wild-type KD1 amino acid sequence.

In another embodiment, the KD1 polypeptide consists essentially of a KD1 domain having a primary structure that is equivalent to or similar to the primary structure of the wild-type KD1 domain of human tissue factor pathway inhibitor-2 (TFPI-2) (SEQ ID NO:2); and optionally a multiply positively charged amino acid sequence disposed at either or both of the N-terminal or C-terminal end of the polypeptide. Preferably, the multiply positively charged amino acid sequence includes an amino acid sequence from the C-terminus of wild-type TFPI-2, more preferably the multiply positively charged amino acid sequence comprises amino acids 192 through 211 of SEQ ID NO:1.

In another embodiment, the KD1 polypeptide includes a covalently or noncovalently attached ligand, such as a receptor ligand or other type of molecule that can specifically target the KD1 polypeptide to a cell of interest.

The KD1 polypeptide of the invention preferably exhibits inhibitory activity against a serine protease that degrades fibrinogen.

The invention also provides a polynucleotide having a nucleotide sequence that encodes a KD1 polypeptide of the invention.

In another aspect, the invention includes pharmaceutical compositions that include a KD1 polypeptide of the invention, or a polynucleotide encoding said KD1 polypeptide, and a pharmaceutically acceptable carrier are also encompassed by the invention, as are polynucleotides encoding a KD1 polypeptide of the invention.

In yet another aspect, the invention includes methods of making a KD1 polypeptide and using a KD1 polypeptide. A method for making for making the KD1 polypeptide can include expressing the polypeptide in a recombinant system, isolating the polypeptide under conditions that cause unfolding of the polypeptide, and refolding the polypeptide in a buffer, preferably a buffer having about pH 9.

Methods of using a KD1 polypeptide preferably utilize wild-type KD1 polypeptide (SEQ ID NO:2) and R24K KD1 polypeptide (SEQ ID NO:3), including subunits thereof, a double or multiple mutant KD1 polypeptide, as well as the targeted forms of any of them as described herein. Targeted forms include a KD1 polypeptide consisting essentially of a KD1 domain having a primary structure that is equivalent to or similar to the primary structure of the wild-type KD1 domain of human tissue factor pathway inhibitor-2 (TFPI-2); and a multiply positively charged amino acid sequence disposed at either or both of the N-terminal or C-terminal end of the polypeptide.

The KD1 polypeptide of the invention, in any form described herein, can advantageously be used to treat a subject for a condition treatable by aprotinin. The condition treatable by aprotinin may be associated with surgery or cardiovascular disease. The KD1 polypeptide can also be used to treat other ailments including, but not limited to, allergies, asthma, cancer or a precancerous condition, influenza infection, or persons in need of surgery, in which case it can be administered to the subject before, during and/or after surgery. The surgery is preferably performed on a component of the vascular system, preferably cardiovascular system. The surgery may be orthopedic surgery.

The KD1 polypeptide of the invention, in any form described herein, or polynucleotide encoding it, can advantageously be used to treat a subject in need of inhibition of plasmin activity. At least one activity of plasmin can be inhibited. Examples of subjects who may be in need of inhibition of plasmin activity include subjects undergoing bone remodeling, subjects afflicted with hemophilia, and subjects afflicted with systemic inflammatory response syndrome (SIRS).

BRIEF DESCRIPTION OF THE DRAWINGS

The file of this patent contains at least one drawing executed in color. Copies of this patent with color drawings will be provided by the Office upon request and payment of the necessary fee.

FIG. 4 shows the amino acid sequences (SEQ ID NOs:4-21) surrounding the $P_1$ reactive site residue in selected Kunitz-type inhibitors. BPTI sequence is from Creighton & Charles (1987, J. Mol. Biol. 194, 11-22), APPI is from Ponte et al. (1988, Nature 331, 525-52), APPH is from Sprecher et al. (1993, Biochemistry 32, 4481-4486), TFPI is from Wun et al. (1988, J. Biol. Chem. 263, 6001-6004), TFPI-2 is from Sprecher et al. (1994, Proc. Natl. Acad. Sci. USA 91, 3353-3357), HAI-1 is from Shimomura et al. (1997, J. Biol. Chem. 272, 6370-6376), HAI-2 is from Kawaguchi et al. (1997, J. Biol. Chem. 272, 27558-27564), IαTI is from Kaumeyer et al. (1986, Nucleic Acids Res. 14, 7839-7850), PLI is from Drobnic-Kosorok et al. (1990, Biol. Chem. Hoppe Seyler 371, 57-61), UPTI is from Stallings-Mann et al. (1994, J. Biol. Chem. 269, 24090-24094), SPI1 is from Nirmala et al. (2001, Eur. J. Biochem. 268, 2064-2073), and AsKC1 is from Schweitz et al. (1995, J. Biol. Chem. 270, 25121-25126).

DETAILED DESCRIPTION OF ILLUSTRATIVE EMBODIMENTS

Abbreviations

KD1, the first Kunitz-type domain of human TFPI-2; TFPI-2, tissue factor pathway inhibitor-2; TFPI, tissue factor pathway inhibitor; VIIa, Factor VIIa; BPTI, bovine pancreatic trypsin inhibitor; APPI, amyloid precursor protein inhibitor; APPH, amyloid precursor protein homolog; HAI, hepatocyte growth factor activator inhibitor; IαTI, Inter-α-trypsin inhibitor; PLI, porcine leukocyte inhibitor; UPTI, uterine plasmin/trypsin inhibitor; SPI1, silk proteinase inhibitor-1; AsKC1, *A. sulcata* kalicludine1; TF, tissue factor; $K_i$, equilibrium inhibition constant; S-2251, H-D-Val-Leu-Lys-p-nitroanilide; S-2288, H-D-Ile-Pro-Arg-p-nitroanilide; IPTG, isopropylthiogalactopyranoside; SDS-PAGE, sodium dodecyl sulfate-polyacrylamide gel electrophoresis; BSA, bovine serum albumin; TBS, 50 mM Tris-HCl (pH 7.5) containing 100 mM NaCl.

Figure 1:
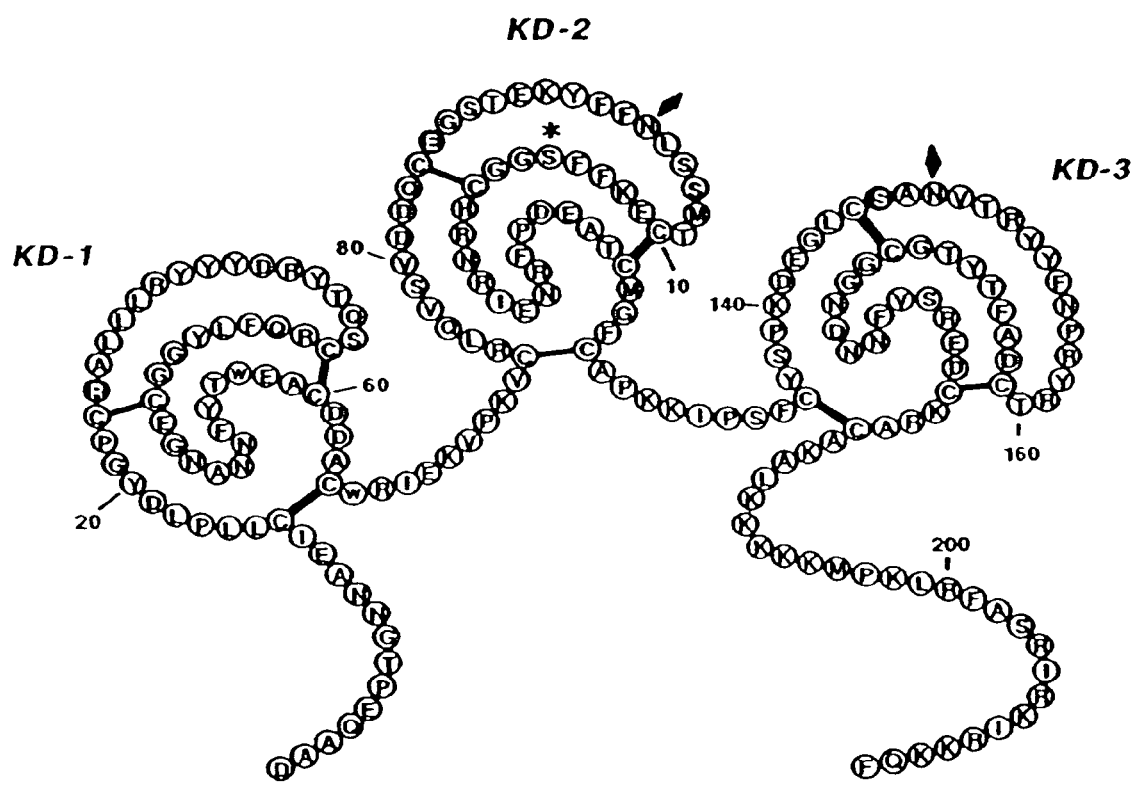
FIG. 1 is a schematic drawing of human tissue factor pathway inhibitor-2 (TFPI-2) including its amino acid sequence (SEQ ID NO:1).
Figure 2:
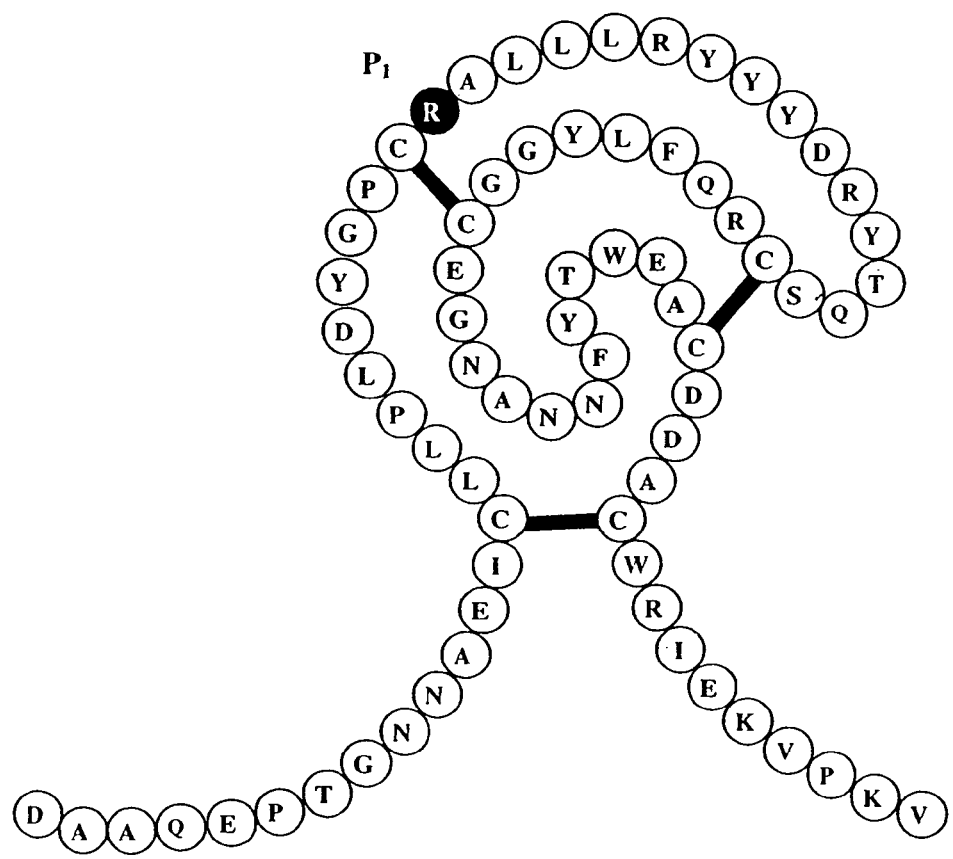
FIG. 2 is a schematic drawing of wild-type TFPI-2 KD1 domain including its amino acid sequence (SEQ ID NO:2). The amino acid sequence shows the arginine residue at the P1 position (Arg24).
Figure 3:
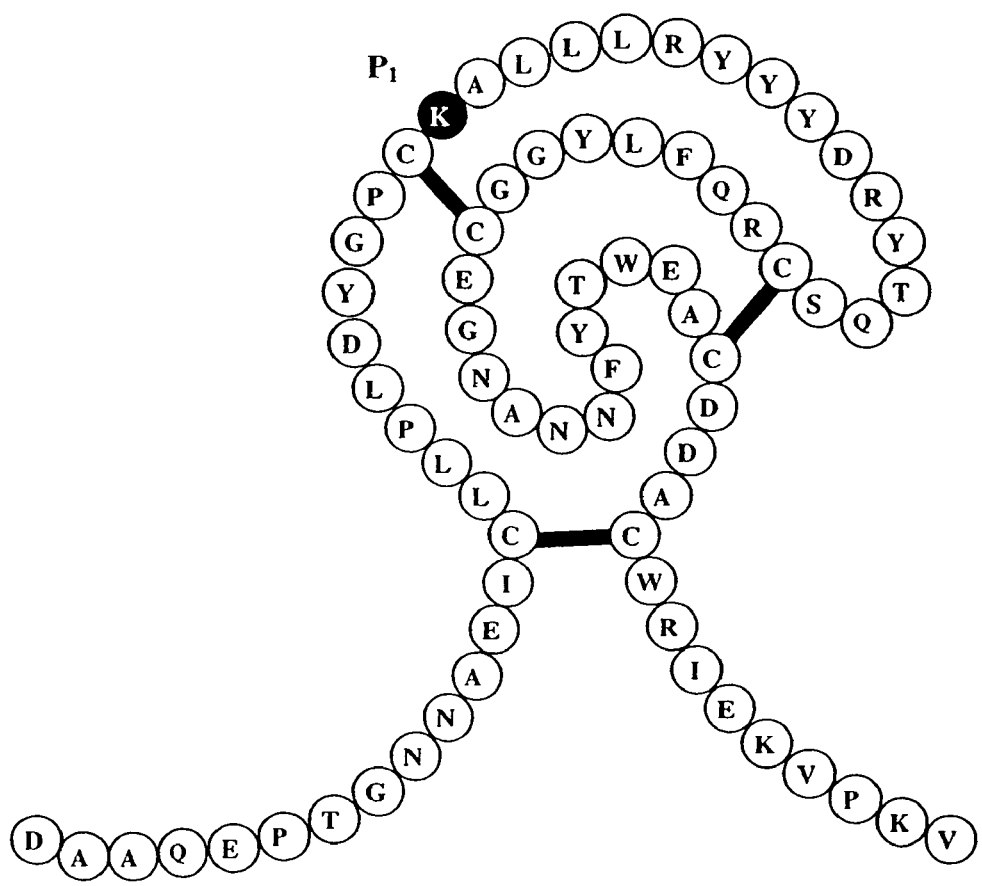
FIG. 3 is a schematic drawing of an R24K TFPI-2 KD1 domain including its amino acid sequence (SEQ ID NO:3). The amino acid sequence shows a lysine residue at the P1 position (Lys24).

The Kunitz inhibitor human type 2 tissue factor pathway inhibitor (TFPI-2) is a 213 amino acid polypeptide comprising three tandem Kunitz-type domains designated as KD1, KD2 and KD3 (FIG. 1). The wild-type KD1 domain includes approximately the first 72 amino acids of the TFPI-2 amino acid sequence (FIG. 2).

In one aspect, the present invention is directed to a KD1 polypeptide that is structurally similar to the first domain, KD1, of wild-type TFPI-2, but has been modified so as to contain a lysine residue at position 24 in place of the wild-type arginine. By "structurally similar" to KD1, it is meant that a polypeptide includes all or most of the amino acid sequence of the wild-type KD1 domain, as well as conservative amino acid substitutions. In other words, the primary structure (amino acid sequence) of the KD1 polypeptide of the invention is essentially the same as the primary structure (amino acid sequence) of wild-type KD1 (optionally including conservative amino acid substitutions), with the proviso that in this aspect of the invention a lysine is present at position 24. The change at position 24 is represented by the notation "R24K" (Arg to Lys at position 24, using the wild-type numbering system). The polypeptide of the invention is thus referred to herein as an "R24K KD1 polypeptide" or simply as "R24K KD1."

The term "structurally similar" to a wild-type KD1 polypeptide indicates that the polypeptide of the invention can include conservative substitutions, especially substitutions of hydrophobic amino acids, relative to the amino acids in wild-type KD1, as long as the substitutions do eliminate the biological activity of the R24K KD1 polypeptide as described below and, in this aspect of the invention, as long as the lysine at position 24 is maintained, since that change represents the essence of the novel polypeptide of this aspect of the invention. The biological activity of a KD1 polypeptide as a protease inhibitor can be readily evaluated using the assays described herein, and it is routine in the art to perform such assays.

Conservative substitutions for an amino acid are selected from other members of the class to which the amino acid belongs. For example, nonpolar (hydrophobic) amino acids include alanine, leucine, isoleucine, valine, proline, phenylalanine, tryptophan, tyrosine and glycine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$. The R24K KD1 polypeptide of the invention includes derivatives, analogs and variants of the polypeptides described herein.

Additionally, the term "structurally similar" to wild-type KD1 indicates that an embodiment of an R24K KD1 polypeptide that includes "most" of the amino acids in the wild-type KD1 domain can include a truncated form of KD1 (also referred to as a "subunit" of KD1) characterized by deletions of 1, 2, 3, 4, 5, 6, 7, 8, 9, or 10 amino acid residues at either or both of the amino-terminal or carboxy-terminal end relative to the wild-type KD1 sequence.

The R24K KD1 polypeptide of the invention may contain one or more additional amino acid substitutions, deletions or additions, provided that the additional modification does not eliminate inhibitory activity of the R24K polypeptide. For example, the R24K KD1 polypeptide of the invention can contain one or more of the following additional modifications relative to wild-type KD1: Leu26Arg, Tyr20Thr, Tyr55Glu, Asp19Glu, Tyr55Lys and/or Asp19Tyr. Examples of other modifications that can be made include modifications at one or more other sites shown in FIG. 15A so as to replace one or more amino acids of KD1 with the corresponding amino acid in BPTI. An R24K KD1 polypeptide having two or more mutations can be described as a "double mutant" KD1 polypeptide or a "multiple mutant" KD1 polypeptide. The term "multiple mutant" is inclusive of the term "double mutant" and signifies a plurality of mutations (i.e., two or more) relative to the wild-type KD1 sequence. It should be understood that unless otherwise indicated, the term R24K KD1 polypeptide as used herein includes KD1 polypeptides that have amino acid substitutions, deletions, or additions in addition to the R24K mutation.

The R24K KD1 polypeptide of the invention preferably includes at least a biologically active portion of the first Kunitz-type domain, KD1, of human tissue factor pathway inhibitor-2 (TFPI-2), modified so as to include a lysine residue rather than arginine at position 24. A biologically active portion of a KD1 domain is a portion that exhibits inhibitory activity against a serine protease, such as plasmin or trypsin, that may be responsible for the degradation of fibrinogen or the activation of a wide variety of proteins involved in tumor metastasis, asthma and influenza virus hemagglutinin activation. In a preferred embodiment, the R24K KD1 polypeptide exhibits a higher degree of antifibrinolytic activity, e.g., enhanced activity toward plasmin and/or trypsin, than that exhibited by wild-type KD1.

Notably, the C-terminus of wild-type TFPI-2 is highly positively charged and has been postulated to bind to matrix proteoglycans. Accordingly, in another aspect, the invention provides a KD1 polypeptide that includes, appended to its C-terminus, an amino acid sequence having multiple (two or more) positive charges. Positively charged amino acids include arginine, lysine and histidine. This embodiment of the KD1 polypeptide, having the positively charged C-terminal "tail," is referred to herein as a "targeted" form of a KD1 polypeptide or simply a "targeted KD1 polypeptide" as it is "targeted," in a nonspecific way, to the matrix proteoglycans or other negatively charged molecules.

In a preferred embodiment, the targeted polypeptide thus consists essentially of two components: a KD1 domain, and a positively charged amino acid sequence attached to one or both termini. The targeted polypeptide does not include a KD2 or KD3 domain as does the wild-type TFPI-2. The KD1 domain of the targeted polypeptide can be equivalent to the wild-type KD1 domain, or it can be a KD1 domain that is structurally similar to the wild-type KD1 domain, as described above, as well as subunits, derivatives, analogs and variants thereof. A particularly preferred embodiment of the targeted polypeptide is one that includes a wild-type KD1 domain or an R24K KD1 domain, and a positively charged amino acid sequence at the C- or N-terminus, as further described herein. As used herein, the term "domain" describes a polypeptide; thus for example a KD1 "domain" refers to the polypeptide that makes up the KD1 domain.

Although any positively charged sequence can be used, the C-terminus of wild-type TFPI-2 represents a convenient and natural choice for use as the positively charged amino acid sequence to form the targeted KD1 polypeptide. For example, a targeted KD1 polypeptide can include, appended to its C-terminus, a positively charged amino acid sequence that lies within the region bounded by amino acid 190 in the N-terminal direction and amino acid 213 in the C-terminal direction of wild-type TFPI-2. Preferably, the positively charge sequence begins at amino acid 190, 191, 192, 193, 194, 195, 196, 197, 198, 199 or 200 of wild-type TFPI-2 (SEQ ID NO:1) and ends at amino acid 211, 212 or 213 of wild-type TFPI-2 (SEQ ID NO:1). An example of a preferred positively charged amino acid sequence is one that begins at amino acid 192 and ends at amino acid 211.

Although the targeted KD1 polypeptide of the invention is described primarily with reference to a positively charged amino acid sequence at the C-terminus, the invention also includes a variation wherein the positively charged amino acid sequence is present instead (or in addition) at the N-terminus, prior to the KD1 amino acid sequence. An example of a targeted, N-terminus modified KD1 polypeptide is a KD1 polypeptide that includes a "histidine tag" (multiple histidines) at the N-terminus.

The positively charged terminal amino acid sequence present on the targeted form of the KD1 polypeptide may bind to one or more negatively-charged proteoglycans in the extracellular matrix and assist the polypeptide in increasing its local concentration in the extracellular matrix, thereby facilitating its ability to readily inhibit serine proteases in this environment. This embodiment of the KD1 polypeptide thus can function in vivo pericellularly by virtue of binding to proteoglycans. Targeting the proteoglycan layer may be especially advantageous in connection with use of the protease inhibitor in cancer, asthma and influenza therapies, as described below.

The KD1 polypeptide can also function in the blood and other extracellular locations, for example to inhibit plasmin, particularly if it is present in the form of an embodiment lacking a positively charged terminal sequence as described in the preceding paragraphs. However, forms of KD1 having one or more positively charged targeting sequences at the C- and or N-terminus (including targeted wild-type KD1 and targeted R24K KD1) are expected to function in the blood and at other extracellular locations as well.

A polypeptide of the invention, such as the wild-type KD1 polypeptide, R24K KD1 polypeptide or the targeted form of either of those polypeptides having the multiply positively charged N-terminus or C-terminus, can be produced by recombinant engineering, for example using a bacterial, insect or mammalian host cell, or by using enzymatic or chemical synthesis in vitro. Preferably, the polypeptide is produced by recombinant engineering in a bacterial cell, such as *E. coli*. Conveniently, while the second and third domains (KD2 and KD3) of TFPI-2 have glycosylation sites, the first domain (KD1) has no known glycosylation sites, making it amenable to expression in bacterial systems, as well as eukaryotic systems.

It should be understood that the term polypeptide as used herein does not connote a specific length of a polymer of amino acids, nor is it intended to imply or distinguish whether the polypeptide is produced using recombinant techniques, chemical or enzymatic synthesis, or is naturally occurring.

A polypeptide of the invention, such as the wild-type KD1 polypeptide, R24K KD1 polypeptide or the targeted form of either of those polypeptides having the multiply positively charged N-terminus or C-terminus, can be readily formulated as a pharmaceutical composition for veterinary or human use. The pharmaceutical composition optionally includes excipients or diluents that are pharmaceutically acceptable as carriers and compatible with the biological material. The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like and combinations thereof. In addition, if desired, the pharmaceutical composition may contain minor amounts of auxiliary substances such as wetting or emulsifying agents, pH buffering agents and/or salts. Also, the pharmaceutical composition can include additional therapeutic agents. Methods of making and using such pharmaceutical compositions are also included in the invention.

Also included in the invention is a polynucleotide comprising a nucleotide sequence that encodes a polypeptide of the invention, for example a wild-type KD1 polypeptide, an R24K KD1 polypeptide or a targeted form of either of those polypeptides having the multiply positively charged N-terminus or C-terminus. The term "polynucleotide" refers broadly to a polymer of two or more nucleotides covalently linked in a 5' to 3' orientation. The terms nucleic acid, nucleic acid sequence, and oligonucleotide are included within the definition of polynucleotide and these terms may be used interchangeably. It should be understood that these terms do not connote a specific length of a polymer of nucleotides, nor are they intended to imply or distinguish whether the polynucleotide is produced using recombinant techniques, chemical or enzymatic synthesis, or is naturally occurring. The polynucleotides of the invention can be DNA, RNA, or a combination thereof, and can include any combination of naturally occurring, chemically modified or enzymatically modified nucleotides.

Polynucleotides can be single-stranded or double-stranded, and the sequence of the second, complementary strand is dictated by the sequence of the first strand. The term "polynucleotide" is therefore to be broadly interpreted as encompassing a single stranded nucleic acid polymer, its complement, and the duplex formed thereby. "Complementarity" of polynucleotides refers to the ability of two single-stranded polynucleotides to base pair with each other, in which an adenine on one polynucleotide will base pair with a thymidine (or uracil, in the case of RNA) on the other, and a cytidine on one polynucleotide will base pair with a guanine on the other. Two polynucleotides are complementary to each other when a nucleotide sequence in one polynucleotide can base pair with a nucleotide sequence in a second polynucleotide. For instance, 5'-ATGC and 5'-GCAT are fully complementary, as are 5'-GCTA and 5'-TAGC.

Preferred polynucleotides of the invention include polynucleotides having a nucleotide sequence that is "substantially complementary" to (a) a nucleotide sequence that encodes a polypeptide according to the invention, or (b) the complement of such nucleotide sequence. "Substantially complementary" polynucleotides can include at least one base pair mismatch, such that at least one nucleotide present on a second polynucleotide, however the two polynucleotides will still have the capacity to hybridize. For instance, the middle nucleotide of each of the two DNA molecules 5'-AGCAAATAT and 5'-ATATATGCT will not base pair, but these two polynucleotides are nonetheless substantially complementary as defined herein. Two polynucleotides are substantially complementary if they hybridize under hybridization conditions exemplified by 2×SSC (SSC: 150 mM NaCl, 15 mM trisodium citrate, pH 7.6) at 55° C. Substantially complementary polynucleotides for purposes of the present invention preferably share at least one region of at least 20 nucleotides in length which shared region has at least 60% nucleotide identity, preferably at least 80% nucleotide identity, more preferably at least 90% nucleotide identity and most preferably at least 95% nucleotide identity. Particularly preferred substantially complementary polynucleotides share a plurality of such regions.

Nucleotide sequences are preferably compared using the Blastn program, version 2.2.10, of the BLAST 2 search algorithm, also as described by Tatusova et al. (FEMS Microbiol. Lett, 174, 247-250 (1999)), and available on the World Wide Web at the National Center for Biotechnology Information website, under BLAST in the Molecular Database section. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. Locations and levels of nucleotide sequence identity between two nucleotide sequences can also be readily determined using CLUSTALW multiple sequence alignment software (J. Thompson et al., Nucl. Acids Res., 22:4673-4680 (1994)), available at from the World Wide Web at the European Bioinformatics Institute website in the "Toolbox" section as the ClustalW program.

It should be understood that a polynucleotide that encodes a polypeptide of the invention is not limited to a polynucleotide that contains all or a portion of naturally occurring genomic or cDNA nucleotide sequence, but also includes the class of polynucleotides that encode such polypeptides as a result of the degeneracy of the genetic code. The class of nucleotide sequences that encode a selected polypeptide sequence is large but finite, and the nucleotide sequence of each member of the class can be readily determined by one skilled in the art by reference to the standard genetic code, wherein different nucleotide triplets (codons) are known to encode the same amino acid. It should further be noted that production, purification and use of human Kunitz type inhibitors, specifically TFPI-2, are described in detail in U.S. Pat. No. 5,914,315 (Sprecher et al.). As it is structurally equivalent to or similar to the first domain of TFPI-2, the KD1 polypeptide of the invention (e.g., wild-type KD1 polypeptide or R24K polypeptide) can be produced, purified and used substantially in accordance with the methods described therein.

In the embodiment described in Example I, R24K KD1 is a recombinant polypeptide that includes residues 1-73 of intact human TFPI-2 with substitution of arginine by lysine at residue number 24. In that embodiment, the N-terminus of R24K KD1 includes four additional amino acid residues derived from the expression vector after the thrombin cleavage site which include, in order, glycine (gly, G), serine (ser, S), histidine (his, H), and methionine (met, M).

The KD1 polypeptide of the invention may be prepared by recombinant DNA technology or synthesized directly, either chemically or enzymatically. An illustrative example of a method for producing a recombinant R24K KD1 is shown in Example I. In that example, R24K KD1 was overexpressed as an N-terminal histidine-tagged fusion protein in *Escherichia coli* strain BL21 (DE3)pLys using the T7 promoter system (Studier et al., *Meth. Enzymol.* 185: 60-89, 1990). The recombinant plasmid derived from pET28a (Novagen, Madison, Wis.) bearing a hexahistidine-tag leader sequence followed by a thrombin cleavage site and cDNA encoding the first Kunitz-type domain of wild-type TFPI-2 was prepared according to standard procedures (Sambrook and Russel, Molecular Cloning: A Laboratory Manual, 3$^{rd}$ Edition, CSHL Press, 2001).

Using this recombinant vector as a template, the mutation of arginine-24 to lysine-24 was generated using a Quick-Change® site-directed mutagenesis kit (Stratagene, La Jolla, Calif.) according to the manufacturer's instruction. The recombinant pET28a-R24K KD1 vector was transformed into BL21(DE3)pLysS by the calcium chloride method (Cohen et al., *Proc. Natl. Acad. Sci. USA* 69:2110-2114, 1972). His-tagged R24K KD1 preparations were expressed in *E. coli* grown in rich media containing 100 mg/L ampicillin, and induced at 37° C. with 1 mM isopropyl thiogalactopyranoside (IPTG) at mid log-phase ($A_{600}$=0.6-0.8).

The overexpressed 6-His-tag R24K KD1 was recovered from the cell lysate in the form of inclusion bodies. The solubilized inclusion bodies were recovered by high-speed centrifugation and filtered through a 0.22μ Nalgene® filter before application to a His-Trap® column (Amersham Biosciences Corp., Piscataway, N.J.). The His-Trap affinity column was used in a Pharmacia Fast Protein Liquid Chromatography system (FPLC) and purification carried out following the manufacturer's protocol.

Fractions eluting from the His-Trap column containing denatured, unfolded $His_6$-R24K KD1 were identified by sodium dodecyl sulfate-polyacrylamide gel electrophoresis (SDS-PAGE; Laemmli, *Nature* 227, 680-685, 1970), pooled, and oxidatively refolded according to the procedure described by Stone and coworkers (Stone et al., *Biochem. J.* 310:605-614, 1995) for the refolding of *E. coli*-derived soluble tissue factor. The refolded protein was then purified to homogeneity by anion exchange chromatography using a MONO Q (MONO Q HR 5/5) FPLC column (Amersham Biosciences Corp., Piscataway, N.J.). R24K KD1 was eluted from this column in a linear NaCl gradient consisting of 50 mM Tris-HCl (pH 9.0) and 50 mM Tris-HCl (pH 9.0) containing 1 M NaCl.

Alternatively, the KD1 polypeptide can be purified by Q-Sepharose FF column chromatography under the same conditions used for the MONO Q FPLC purification. Fractions were subjected to SDS-PAGE analysis and fractions containing pure $His_6$-R24K KD1, as evidenced by a single band, were pooled for further analysis. The purified $His_6$-R24K KD1 was then dialyzed against 50 mM Tris-HCl (pH 8) and subsequently treated with human thrombin (1:1000 enzyme:protein molar ratio) for 6 hours at 37° C. to cleave and separate the His-tag leader sequence from the R24K KD1. The liberated His-tag was removed from the digest by FPLC using a His-Trap® column, and the R24K KD1/thrombin mixture eluted in the unadsorbed fraction. Thrombin was removed from the sample by SP-Sephadex C-50 chromatography as described for the purification of thrombin (Kisiel et al., *Blood* 66: 1302-1308, 1985). The concentration of the R24K KD1 was determined by measuring its absorbance at 280 nm using a calculated value for $E^{1\%}$ derived from its tyrosine, tryptophan and cysteine content (Gill and von Hippel, *Anal. Biochem.* 182: 319-326, 1989).

The invention provides a novel method for purifying the KD1 polypeptide of the invention, such as a wild-type KD1 polypeptide or the R24K KD1 polypeptide, as exemplified in Example II. Refolding of the solubilized, denatured polypeptide in urea is facilitated by raising the pH to about 9, such that the protein can be refolded at higher concentrations. Refolding and purification at pH 9 markedly decreases precipitation of the denatured polypeptide commonly observed in refolding strategies. Without intending to limit the invention to any particular mechanism of action, improved solubility and recovery of the R24K KD1 at pH 9 is probably related to the high calculated pI value of R24K KD1 (pI=7.44).

The inhibitory activity of purified recombinant KD1 polypeptide of the invention, such as wild-type KD1 polypeptide, R24K KD1 polypeptide, or the targeted form of either of them having a multiply positively charged N-terminus or C-terminus, toward plasmin is readily assessed, for example, as described in Petersen et al. (*Biochemistry* 35:266-272, 1996). Example I provides an illustrative example of assessment of the inhibitory activity. Briefly, human plasmin (30 nM; Haematologic Technologies Inc., Essex Junction, Vt.) was incubated with various concentrations of R24K KD1 for 15 min at 37° C. in a 96-well microtitration plate. The chromogenic substrate S-2251 (D-Val-Leu-Lys-p-nitroanilide; DiaPharma Group Inc., West Chester, Ohio) was then added and residual plasmin amidolytic activity was measured at 405 nm in a Molecular Devices $UV_{max}$ kinetic microplate reader. The inhibition constant, $K_i$, for R24K KD1 inhibition of plasmin was determined using the non-linear regression data analysis program Ultrafitfv3.0 as described (see Example I).

As demonstrated in Example I, the isolated first Kunitz-type domain (KD1) of human TFPI-2 (see FIG. 2) exhibited stronger inhibitory activity towards several serine proteinases in comparison to intact TFPI-2. The R24K KD1 mutant polypeptide exhibited enhanced inhibitory activity toward plasmin and trypsin in comparison to wild-type KD1. R24K KD1 was prepared by substituting the reactive site $P_1$ arginine residue at position 24 with a lysine residue by site-specific mutagenesis. R24K KD1 was shown to inhibit the fibrinolytic proteinase plasmin with an inhibition constant ($K_i$) of 0.85 nM, which is similar (0.75 nM) to that observed for the inhibition of plasmin by the prototypical Kunitz-type inhibitor known as bovine pancreatic trypsin inhibitor (BPTI), also known commercially as aprotinin or Trasylol®. Unexpectedly, a lysine substitution at the $P_1$ position (R24K) in KD1 significantly increased its inhibitory activity toward plasmin, making it essentially as effective as BPTI toward this proteinase.

The present invention further includes antibodies, both monoclonal and polyclonal, that bind specifically to the R24K KD1 polypeptide, thereby distinguishing it from wild-type KD1. The R24K KD1 polypeptide of the invention can be used as an antigen to produce antibodies, including vertebrate antibodies, hybrid antibodies, chimeric antibodies, humanized antibodies, altered antibodies, univalent antibodies, monoclonal and polyclonal antibodies, Fab proteins and single domain antibodies. Optionally, the polypeptide is covalently linked to an immunogenic carrier such as keyhole limpet hemocyanin (KLH), bovine serum albumin, ovalbumin, mouse serum albumin, rabbit serum albumin, and the like.

If polyclonal antibodies are desired, a selected animal (e.g., mouse, rabbit, goat, horse or bird, such as chicken) is immunized with the R24K KD1 polypeptide. Serum from the immunized animal is collected and treated according to known procedures. If the serum contains polyclonal antibodies that bind to the R24K polypeptide, the polyclonal antibodies can be purified by immunoaffinity chromatography. Techniques for producing and processing polyclonal antisera are known in the art (see for example, Mayer and Walker eds. Immunochemical Methods in Cell and Molecular Biology (Academic Press, London) (1987), Coligan, et al., Unit 9, Current Protocols in Immunology, Wiley Interscience (1991), Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992)).

Monoclonal antibodies directed against R24K KD1 polypeptide are also included in the invention, and can be readily produced by one skilled in the art. The general methodology for making monoclonal antibodies by hybridomas is well known. Immortal antibody-producing cell lines can be created by cell fusion, and also by other techniques such as direct transformation of B lymphocyte cells with oncogenic DNA, or transfection with Epstein-Barr virus (See Monoclonal Antibody Production. Committee on Methods of Producing Monoclonal Antibodies, Institute for Laboratory Animal Research, National Research Council; The National Academies Press; (1999), Kohler & Milstein, Nature, 256: 495 (1975); Coligan et al., sections 2.5.1-2.6.7; and Harlow et al., Antibodies: A Laboratory Manual, page 726 (Cold Spring Harbor Pub. 1988)). Panels of monoclonal antibodies produced against the polypeptide of the invention can be screened for various properties, for example epitope affinity.

Antibodies can also be prepared through use of phage display techniques. Phage display methods to isolate antigens and antibodies are known in the art and have been described (Gram et al., Proc. Natl. Acad. Sci., 89:3576 (1992); Kay et al., Phage display of peptides and proteins: A laboratory manual. San Diego: Academic Press (1996); Kermani et al., Hybrid, 14:323 (1995); Schmitz et al., Placenta, 21 Suppl. A:S106 (2000); Sanna et al., Proc. Natl. Acad. Sci., 92:6439 (1995)).

Antibody specificity can be evaluated, for example, by performing Western blot analysis and comparing the results for wild-type KD1 polypeptide and R24K KD1 polypeptide. Antibodies that bind to R24K KD1 polypeptide but not wild-type KD1 polypeptide are considered to be specific for the R24K KD1 polypeptide of the invention. The R24K KD1 polypeptide of the invention has many therapeutic applications. This polypeptide has structural and functional properties that are virtually identical to aprotinin, and therefore is expected to be advantageous for use in any therapeutic application for which aprotinin is useful. Unlike aprotinin, however, the R24K polypeptide of the invention is based on a polypeptide of human origin. Accordingly, the incidences of reactivity to it are expected to be very low in comparison to aprotinin, which elicits adverse reactions, such as anaphylaxis, in 0.5% to 1% of patients (and a higher rate in patients receiving aprotinin a second time).

Like aprotinin, the polypeptide of the invention can be used as an inhibitor of fibrinolysis and coagulation in patients undergoing surgery for treatment before, during and after cardiovascular surgery such as cardiopulmonary bypass procedures, as well as other therapeutic applications, such as deep vein thrombosis, disseminated intravascular coagulation, pulmonary embolism and for the prevention of thrombosis following surgery. For example, the wild-type KD1 polypeptide or the R24K KD1 polypeptide, or a targeted form of either of them as described herein, can be used prophylactically to reduce perioperative blood loss and the need for blood transfusion in patients undergoing cardiopulmonary bypass (CPB) in the course of coronary artery bypass graft (CABG) surgery. Aprotinin has also been used to block thrombin-mediated PAR 1 activation on platelets of patients undergoing coronary artery bypass grafting (Day et al, Circulation 110: 2597-2600, 2004), and it is expected that the polypeptide of the invention will have analogous activity.

The mode of administration and dosing regimen for the KD1 polypeptide are similar to those used for aprotinin for similar applications. As aprotinin is well known and in current therapeutic use, one of skill in the art will appreciate that the dosing amounts and regimens, and methods of administration, that are applicable to aprotinin can be readily employed for use with the KD1 polypeptide of the invention, such as wild-type KD1 polypeptide or R24K polypeptide. Dosing regimens for aprotinin (Trasylol®, Bayer Corporation, West Haven, Conn.) are applicable to the R24K polypeptide of the invention and can be found in the 2004 Physician's Desk Reference on page 864. A recent article describing aprotinin dosing (Niimi, J. Extra Corpor Technol 36: 384-390, 2004) also sets forth exemplary protocols including amounts, timing, modes of administration, and the like. See also Levy et al., "Efficacy and Safety of Aprotinin in Cardiac Surgery," Orthopedics (June 2004 Supplement) and Levy et al., Aprotinin: A Pharmacologic Overview," (June 2004 Supplement), available online at the HYPERLINK "www.orthosupersite.com." Administration by any convenient route is contemplated, including parenteral administration, such as intravenous injection, intramuscular injection, inhalation or topical application; however, the preferred method of administration is intravenous injection and perfusion.

In addition, since plasmin is a key proteinase in many pathological conditions associated with malignancy and the migration of cells to inflammatory sites in vivo, it is contemplated that the KD1 polypeptide of the invention, such as wild-type KD1 polypeptide, R24K KD1 polypeptide, or the targeted forms of either of them as described herein, finds further therapeutic applications in the treatment of cancer and asthma (see Examples I and III; Chand et al., J. Biol. Chem. 2004; 279(17):17500-7; Epub 2004 Feb. 16. Erratum in: J. Biol. Chem. 2004; 279(23):24906; Chand et al., Blood 103: 1069-1077, 2004; Epub 2003 Oct. 2). In particular, a KD1 polypeptide such as wild-type KD1 as well as the R24K KD1 polypeptide can be used to treat asthma. In an art-recognized animal model, hexahistidine-tagged KD1 was shown to block leukocytes from migrating into the lung (Example IV), thereby indicating that it represents an effective asthma therapy. The KD1 polypeptide can be administered to an asthmatic subject in any convenient manner, such as intravenously, intramuscularly or by inhalation. Intravenous injection can be accomplished using an implanted pump. Preferably, however, the polypeptide is administered via inhalation, for example as an aerosol. The KD1 polypeptide can be administered in acute episodes of asthma, for example as treatment for an asthmatic attack or anaphylaxis or as a continuing, periodic treatment for chronic asthmatic conditions.

A KD1 polypeptide of the invention such as wild-type KD1 as well as the R24K KD1 polypeptide, including the targeted forms thereof, can be used to treat cancer and precancerous conditions. It is known that some tumors downregulate TFPI-2. Tumor cells can secrete one or more proteases, but this may not be accompanied by secretion of one or more protease inhibitors. The uninhibited protease causes proteolytic digestion of basement membranes, for example, and allows the tumor cells to mobilize, facilitating metastases. This process can be counteracted by, for example, administering a wild-type KD1 polypeptide or an R24K KD1 polypeptide to the subject, for example using via indwelling pumps, to reduce tumor growth and tumor metastasis.

Additionally, we have shown that hexahistidine-tagged human KD1 exhibits dose-dependent inhibition of angiogenesis in a commercially available in vitro human endothelial cell angiogenesis assay. The angiogenesis assay is commercially available from Chemicon International, Inc. (Temecula, Calif.), and involves growing human umbilical vein endothelial cells (HUVECs) on a proprietary matrix, followed by assessing angiogenesis on this matrix by counting new branch points in sprouting endothelial cells.

The KD1 polypeptide of the invention, including a wild-type KD1 and an R24K KD1 polypeptide, as well as their targeted forms as described herein, may be also be used therapeutically to treat influenza infections. Aprotinin has been shown to inhibit the cleavage of influenza A virus hemagglutinin in vitro, and diminished the infectivity of the virus (Zhirnov et al., J. Virol. 76: 8682-8689, 2002). The KD1 polypeptide of the invention is expected to have similar activity.

The KD1 polypeptide of the invention, in any form described herein, or polynucleotide encoding it, can advantageously be used to treat a subject in need of inhibition of plasmin activity. At least one activity of plasmin can be inhibited. Examples of subjects who may be in need of inhibition of plasmin activity include subjects undergoing bone remodeling, subjects afflicted with hemophilia, and subjects afflicted with systemic inflammatory response syndrome (SIRS).

In therapeutic applications, it may be particularly advantageous to append to the KD1 polypeptide (such as a wild-type KD1 polypeptide or a R24K KD1 polypeptide) the multiply positively charged C-terminus or N-terminus region as described above, so as to target the extracellular matrix and prevent its breakdown by tumor cell-secreted proteases.

EXAMPLES

The present invention is illustrated by the following examples. It is to be understood that the particular examples, materials, amounts, and procedures are to be interpreted broadly in accordance with the scope and spirit of the invention as set forth herein.

Example I

Structure-Function Analysis of the Reactive Site in the First Kunitz-Type Domain of Human Tissue Factor Pathway Inhibitor-2

Summary

Human tissue factor pathway inhibitor-2 (TFPI-2) is a Kunitz-type proteinase inhibitor that regulates a variety of serine proteinases involved in coagulation and fibrinolysis through their non-productive interaction with a $P_1$ residue (Arg24) in its first Kunitz-type domain (KD1). Previous kinetic studies revealed that TFPI-2 was a more effective inhibitor of plasmin than several other serine proteinases, but the molecular basis for this specificity was unclear. In this study, we employed molecular modeling and mutagenesis strategies to produce several variants of human TFPI-2 KD1 in an effort to identify interactive site residues other than the $P_1$ Arg that contribute significantly to its inhibitory activity and specificity. Molecular modeling of KD1 based on the crystal structure of bovine pancreatic trypsin inhibitor revealed that KD1 formed a more energetically favorable complex with plasmin versus trypsin and/or the factor VIIa-tissue factor complex primarily due to strong ionic interactions between Asp19 ($P_6$) and Arg residues in plasmin (Arg644, Arg719 and Arg767), Arg24 ($P_1$) with Asp735 in plasmin, and Arg29 ($P_5$') with Glu606 in plasmin. In addition, Leu26-28 ($P_2$'-$P_4$') in KD1 formed strong van der Waals contact with a hydrophobic cluster in plasmin (Phe583, Met585 and Phe587). Mutagenesis of Asp19, Tyr20, Arg24, Arg29, and Leu26 in KD1 resulted in substantial reductions in plasmin inhibitory activity relative to wild-type KD1, but the Asp19 and Tyr20 mutations revealed the importance of these residues in the specific inhibition of plasmin. In addition to the reactive site residues in the $P_6$-$P_5$' region of KD1, mutation of a highly conserved Phe at the $P_{18}$' position revealed the importance of this residue in the inhibition of serine proteinases by KD1. Thus, together with the $P_1$ residue, the nature of other residues flanking the $P_1$ residue, particularly at $P_6$ and $P_5$', strongly influences the inhibitory activity and specificity of human TFPI-2.

Introduction

Proteinase inhibitors play a critical role in the regulation of several physiological processes such as blood coagulation, complement fixation, fibrinolysis, and fertilization (Bode et al., 2000, Biochim. Biophys. Acta 1477, 241-252). Most of these inhibitors are proteins having characteristic polypeptide scaffolds, and are grouped into a number of families including the Kunitz (Laskowski et al., 1980, Ann. Rev. Biochem. 49, 593-626), Kazal (Laskowski et al., 1980, Ann. Rev. Biochem. 49, 593-626), Serpin (Potempa et al., 1994, J. Biol. Chem. 269, 15957-15960) and mucus (Wiedow et al., 1990, J. Biol. Chem. 265, 14791-14795) families. The Kunitz-type family, serine proteinase inhibitors that include one or more Kunitz-type inhibitory domains, includes tissue factor pathway inhibitor (TFPI)[1] and type-2 tissue factor pathway inhibitor (TFPI-2). These two inhibitors have been investigated extensively in the past decade, and have been shown to play an important role in inhibiting serine proteinases involved in coagulation and fibrinolysis (Girard et al., 1989, Nature 338, 518-520; Broze et al., 1990, Biochemistry 29, 7539-46; Sprecher et al., 1994, Proc. Natl. Acad. Sci. USA 91, 3353-3357; Bajaj et al., 2001, Thromb. Haemost. 86, 959-972).

Human TFPI-2, originally isolated from placenta and designated as placental protein 5 (PP5), is a matrix-associated inhibitor consisting of three tandemly arranged Kunitz-type proteinase inhibitor domains flanked by a short acidic amino-terminus and a highly basic carboxy-terminal tail (Sprecher et al., 1994, Proc. Natl. Acad. Sci. USA 91, 3353-3357; Miyagi et al., 1994, J. Biochem. 116, 939-942). A wide variety of cells including keratinocytes (Rao et al., 1995, J. Invest. Dermatol. 104, 379-383), dermal fibroblasts (Rao et al., 1995, J. Invest. Dermatol. 104, 379-383), smooth muscle cells (Herman et al., 2001, J. Clin. Invest. 107, 1117-1126), syncytiotrophoblasts (Udagawa et al., 1998, Placenta 19, 217-223), synoviocytes (Sugiyama et al., 2002, FEBS Lett. 517, 121-128) and endothelial cells (Iino et al., 1998, Arterioscler. Thromb. Vasc. Biol. 18, 40-46) synthesize and secrete TFPI-2 primarily into their extracellular matrix. Three variants/isoforms of molecular mass 32 kDa, 30 kDa and 27 kDa are synthesized by these cells and are thought to represent differentially glycosylated forms (Rao et al., 1996, Arch. Biochem. Biophys. 335, 45-52).

TFPI-2 exhibits inhibitory activity towards a broad spectrum of proteinases including trypsin, plasmin, chymotrypsin, cathepsin G, plasma kallikrein and the factor VIIa-tissue factor complex. However, TFPI-2 exhibits little, if any, inhibitory activity towards urokinase-type plasminogen activator (uPA), tissue-type plasminogen activator (tPA) and α-thrombin (Petersen et al., 1996, Biochemistry 35, 266-272). TFPI-2 presumably inhibits proteinases through a $P_1$ arginine residue (R24) in its first Kunitz-type domain, as an R24Q TFPI-2 mutant exhibited only 5-10% inhibitory activity towards trypsin, plasmin and the factor VIIa-tissue factor complex (Kamei et al., 1999, Thromb. Res. 94, 147-152).

Recently, TFPI-2 expression by select tumors has been shown to play a significant role in inhibiting tumor growth and metastasis by a mechanism that involves its inhibitory activity (Konduri et al., 2001, Oncogene 20, 6938-6945; Chand et al., 2004, Blood 103, 1069-1077; Epub 2003 Oct. 2; Example III).

Several approaches have been employed to elucidate the structure-function relationship and broad specificity of Kunitz-type inhibitors using the well-characterized bovine pancreatic trypsin inhibitor (BPTI) as a model. Detailed biophysical and biochemical studies have provided a greater insight into the structural basis for the association of BPTI, or its homologues, to proteinases. Moreover, using semisynthetic (Wenzel et al., 1982, FEBS Lett. 140, 53-57; Tschesche et al., 1987, Biochim. Biophys. Acta 913, 97-101) or recombinant approaches (Stassen et al., 1995, Thromb. Haemost. 74, 655-659; Kraunsoe et al., 1996, FEBS Lett. 396, 108-112), it has been possible to change or enhance the inhibitory activity and spectrum of BPTI, as well as its homologues.

Kunitz-type inhibitors possess a compact pear-shaped structure stabilized by three disulfide bonds containing a reactive site region featuring the principal determinant $P_1$ residue in a rigid conformation. These inhibitors competitively prevent access of the serine proteinase for its physiologically relevant macromolecular substrate through insertion of the $P_1$ residue into the active site cleft (Wlodawer et al., 1987, J. Mol. Biol. 193, 145-156). In addition to the $P_1$ residue, other residues within the reactive site region of BPTI ($P_4$-$P_4$') have been shown to interact with different serine proteinases, and it is generally recognized that the N-terminal side of the reactive site (P) is energetically more important than the P' C-terminal side (Perona et al., 1997, J. Biol. Chem. 272, 29987-29990). In all, about 10-12 amino acid residues in the inhibitor and 20-25 residues in the proteinase are in direct contact in the formation of a stable proteinase-inhibitor complex, and provide a buried area of 600-900 Å (Janin et al., 1990, J. Biol. Chem. 265, 16027-16030). While many proteins structurally similar to BPTI, such as TFPI KD2 (Burgering et al., 1997, J. Mol. Biol. 269, 395-407), APPI (Scheidig et al., 1997, Protein Sci. 6, 1806-1824) and bikunin (Xu et al., 1998, J. Mol. Biol. 276, 955-966), have been isolated and their three dimensional structures determined, there are few studies that have assigned the relative contribution of residues flanking the reactive site residue in the formation of the proteinase-inhibitor complex and their affect on inhibitory activity and specificity (Van Norstrand et al., 1995, J. Biol. Chem. 270, 22827-22830; Castro et al., 1996, Biochemistry 35, 11435-11446; Grzesiak et al., 2000b, J. Biol. Chem. 275, 33346-33352).

In the case of TFPI-2, it is generally believed that its first Kunitz-type domain, in a BPTI-like manner, harbors most of its inhibitory activity, although no studies have definitively shown that this domain is sufficient to mediate this activity. In the present study, the complete first Kunitz domain of human TFPI-2 was expressed and purified, and its inhibitory activity towards selected proteinases was compared with that of full-length TFPI-2 and BPTI. In addition, molecular modeling was employed to obtain three-dimensional structural information on complexes of TFPI-2 KD1-plasmin, TFPI-2 KD1-trypsin and TFPI-2 KD1-factor VIIa in order to identify residues in KD1 involved in its molecular recognition of each proteinase. From this analysis, residues primarily responsible for the interaction and proteinase specificity were then selected for mutagenesis. Select amino acid residues on both the N-terminal and C-terminal side of the reactive site residue ($P_1$) were substituted individually, and the effects of these point-mutations on the proteinase specificity and inhibitory activity were investigated.

Experimental Procedures

Materials

The chromogenic substrates H-D-Val-Leu-Lys-p-nitroanilide (S-2251) and H-D-Ile-Pro-Arg-p-nitroanilide (S-2288) were purchased from DiaPharma Group Inc (West Chester, Ohio, USA). Human plasmin was purchased from Haematologic Technologies, Inc. (Essex Junction, Vt., USA). Human recombinant factor VIIa, porcine trypsin and bovine aprotinin (BPTI) were generously provided by Novo Nordisk (Copenhagen, Denmark). *Escherichia coli* strain BL21 (DE3)pLys and pET19b expression vector were products of Novagen Inc. (Madison, Wis.). The QuickChange® site-directed mutagenesis kit was obtained from Stratagene (La Jolla, Calif.). YM3 ultrafiltration membranes were purchased from Millipore (Bedford, Mass.). His-Trap® columns were obtained from Amersham Biosciences Corp. (Piscataway, N.J.). Novex 4-20% Tris-glycine polyacrylamide gels were purchased from Invitrogen (Carlsbad, Calif.). Recombinant human TFPI-2 (Sprecher et al., 1994, Proc. Natl. Acad. Sci. USA 91, 3353-3357), recombinant soluble tissue factor (Petersen et al., 1996, Biochemistry 35, 266-272), and protein-A Sepharose-purified anti-human TFPI-2 IgG (Iino et al., 1998, Arterioscler. Thromb. Vasc. Biol. 18, 40-46) were prepared according to published methods. All other reagents were the highest purity commercially available.

Molecular Modeling

Three-dimensional structural information on complexes formed between KD1 and plasmin, KD1 and trypsin, and KD1 and factor VIIa was obtained using molecular modeling strategies. The crystallographically-determined structures of factor VIIa-TF inhibited with a BPTI mutant (Zhang et al., 1999, J. Mol. Biol. 285, 2089-2104; pdb code 1fak), factor VIIa-TF (Banner et al., 1996, Nature 380, 41-46; pdb code 1dan), trypsin inhibited with TFPI KD2 (Burgering et al., 1997, J. Mol. Biol. 269, 395-407; pdb code 1tfx), the NMR determined structure of TFPI KD2 (Burgering et al., 1997, J. Mol. Biol. 269, 395-407; pdb code 1adz), trypsin inhibited with BPTI (Huber et al., 1974, J. Mol. Biol. 89: 73-101; pdb code 2ptc), and plasmin (Wang et al., 1998, Science 281, 1662-1665; pdb code 1bml) served as templates in building these models. Bulk solvent was excluded from the proteinase-inhibitor complex and, accordingly, it was anticipated that hydrogen bonds and ionic interactions that may play an important role in specificity could be accurately evaluated. The protocols for modeling these complexes have been described in detail elsewhere (Bajaj et al., 2001, Thromb. Haemost. 86, 959-972). Briefly, the relative positions of the inhibitor and proteinase domains were maintained and adjustments were only made to the side chains. Hydrophobic/van der Waals, hydrogen bonds, and ionic interactions were observed between each proteinase-inhibitor complex. All of these interactions were taken into consideration in evaluating each proteinase-inhibitor complex, and it was assumed that all potential hydrogen bond donors and acceptors would participate in these interactions.

Expression and Purification of Wild-type and Mutant Proteins

The first Kunitz-type proteinase inhibitor domain of human TFPI-2 (KD1) and its mutants were overexpressed as N-terminal His-tagged fusion proteins in *Escherichia coli* strain BL21(DE3)pLys using the T7 promoter system (Studier et al., 1990, Methods Enzymol. 185, 60-89). The recombinant plasmid derived from pET19b bearing a deca-histidine-tag leader sequence followed by an enterokinase cleavage site and cDNA encoding the first Kunitz-domain of TFPI-2 was prepared according to standard procedures (Sambrook et al., 2001, Molecular Cloning: A laboratory Manual, Third Edition, CSHL press). Using this recombinant vector as a template, several other constructs containing the desired point mutations were generated using a QuickChange® site-directed mutagenesis kit according to the manufacturer's instructions. Each recombinant construct was examined for in-frame orientation, integrity and desired mutation by nucleic acid sequencing. Wild-type and mutant His-tag KD1 preparations were expressed in *E. coli* grown in rich media containing 100 mg/L ampicillin, and induced at 37° C. with 1 mM isopropyl thiogalactopyranoside (IPTG) at mid log-phase ($A_{600}$=0.6-0.8). The overexpressed proteins were recovered from the cell lysates in the form of inclusion bodies following sonication in 50 mM Tris-HCl (pH 8.0) containing 0.5 M NaCl, 5 mM 2-mercaptoethanol, and 10 mM imidazole (buffer A). Inclusion bodies were recovered by high-speed centrifugation (20,000×g for 60 minutes) and thoroughly washed overnight at room temperature before solubilizing in buffer A containing 6M guanidine hydrochloride. The solubilized inclusion bodies were recovered by high speed centrifugation and were filtered through 0.22μ Nalgene® filters before application to His-Trap® column individually dedicated to each expressed protein. His-Trap affinity columns were used in a Pharmacia FPLC system and purification was carried out following the manufacturer's protocol. Peak fractions were identified by SDS-PAGE, pooled, and oxidatively refolded by initial dialysis against 50 mM Tris-HCl (pH 8.0) containing 3 mM 2-mercaptoethanol, followed by extensive dialysis against 50 mM Tris-HCl (pH 8.0).

The refolded proteins were purified to homogeneity by Mono Q FPLC at room temperature. KD1 proteins were eluted from this column in a linear NaCl gradient consisting of 50 mM Tris-HCl (pH 8) and 50 mM Tris-HCl (pH 8) containing 1 M NaCl. Peak fractions were subjected to SDS-PAGE analysis, and pure fractions were pooled and concentrated on YM-3 ultrafiltration membranes.

General Methods

The concentration of each purified KD1 protein was determined by measuring its absorbance at 280 nm using calculated values for $E^{1\%}$ derived from its Tyr, Trp and Cys content (Gill et al., 1989, Anal. Biochem. 182, 319-326). The concentration of plasmin was provided by the supplier, whereas the concentrations of all other proteins used in this study were determined according to Bradford (1976, Anal. Biochem. 72, 248-254) using BSA as the reference protein. SDS-PAGE was performed according to Laemmli (1970, Nature 227, 680-685) using 4-20% polyacrylamide gradient gels.

Trypsin and Plasmin Inhibition Assays

Trypsin and plasmin inhibition assays were performed as described elsewhere (Petersen et al., 1996, Biochemistry 35, 266-272). Briefly, trypsin and plasmin were incubated with various concentrations of inhibitor preparations for 15 minutes at 37° C. in a 96-well microtitration plate. The chromogenic substrate S-2251 was then added and residual amidolytic activity was measured in a Molecular Devices $UV_{max}$ kinetic microplate reader.

Inhibition Assay for Factor VIIa-Tissue Factor Amidolytic Activity

Recombinant soluble human tissue factor (100 nM) and factor VIIa (50 nM) were incubated in a TBS-BSA buffer/5 mM $CaCl_2$ for 15 minutes at 37° C. Following this incubation, aliquots (100 μl) were dispensed into a 96-well microtitration plate and treated with serial dilutions of inhibitors dissolved in TBS buffer. After 15 minutes of incubation, 30 μl of S-2288 (final concentration, 1 mM) was added to each well and the absorbance at 405 nm was determined as described earlier.

Inhibition Kinetics

The apparent inhibition constant, $K_i'$ was determined using the non-linear regression data analysis program Ultrafitfv3.0 (Biosoft). Trypsin and plasmin inhibitory data were analyzed according to the following equation for a tight-binding inhibitor:

$$v_i = v_0[\sqrt{(K_i'+[I]_0+[E]_0)^2 - 4[I]_0[E]_0} - (K_i'+[I]_0-[E]_0)]/2[E]_0$$

where $v_i$ and $v_0$ are the inhibited and uninhibited rates, respectively, and $[I]_0$ and $[E]_0$ are the total concentrations of inhibitor and enzyme, respectively. Factor VIIa-tissue factor inhibition data, where $K_i' \gg [E]_0$, were analyzed according to the following equation:

$$v_i = v_0/(1+[I]_0/K_i')$$

$K_i$ values were obtained by correcting for the effect of substrate according to Bieth et al. (Bieth, 1984, Biochem. Med. 32, 387-397), where $K_i = K_i'/(1+[S]/K_m)$.

Results

Molecular Modeling and Selection of Mutations

Previous studies demonstrated that human TFPI-2 is a strong inhibitor of plasmin and trypsin, and a relatively weak inhibitor of the factor VIa-tissue factor complex (Petersen et al., 1996, Biochemistry 35, 266-272). The molecular basis of TFPI-2's specificity for plasmin and trypsin relative to the serine proteinase factor VIIa is unclear, but presumably involves residues other than the $P_1$ Arg in the first Kunitz-type domain of TFPI-2, as well as residues in the active site region of the proteinase. In order to address whether other residues in the reactive site region of TFPI-2 may play a role in its inhibitory potency and specificity, we employed a molecular modeling approach to guide subsequent mutagenesis studies designed to provide information on the functional importance of these residues. As our preliminary data indicated that a recombinant preparation of the first Kunitz-type domain of TFPI-2 (KD1) exhibited better inhibitory activity in comparison to the intact parent molecule (see below), we decided to model complexes of KD1 with plasmin, trypsin and factor VIIa based on the crystal structure of BPTI and each proteinase, respectively. A preliminary inspection of the amino acid sequences surrounding the $P_1$ residue in a number of Kunitz-type inhibitors revealed highly conserved residues at the $P_6$, $P_1$, $P_5'$ and $P_{18}'$ positions (FIG. 4), and our molecular modeling studies thus initially focused on the contributions of these residues in the formation of an energetically stable complex between KD1 and the above proteinases. In the model structures of these complexes, no unfavorable contacts between atoms and no unnatural chiral centers were observed. In the Ramachandran plot of the main-chain φ-φ angles, all of the non-glycine residues are in the most favored or permissive regions. Moreover, there are no gross steric clashes that preclude the interaction of proteinases with KD1. For simplicity and consistency, the residue numbering system employed for KD1 and each proteinase is that of its linear sequence position. In addition, in order to relate each proteinase residue number to its corresponding position in the prototypical proteinase chymotrypsin, each proteinase residue number is followed by its position in chymotrypsin in braces, and is preceded by the letter "c". Finally, the relationship between residues mutated in KD1 and their position in BPTI is indicated in Table I. Note that the residues in KD1 differ by nine from BPTI; thus, residue 24 ($P_1$ residue) in KD1 is equivalent to 15 in BPTI. For simplicity, KD1 numbering system is used in this document.

TABLE I $K_i$ Values For The Inhibition Of Selected Proteinases By Human TFPI-2, KD1, KD1 Point-Mutants and BPTI.

| | $K_i$ [nM] | | |
|---|---|---|---|
| Inhibitor | Plasmin [30 nM] | Trypsin [50 nM] | FVIIa-TF [50/100 nM] |
| TFPI-2 | 9 | 21 | 1910 |
| KD1 | 3 | 13 | 1640 |
| D19A (D10A)[a] | 118 | 15 | 1960 |
| Y20A (Y11A) | 16 | 8 | 1350 |
| G21D (G12D) | 59 | 42 | 26000 |
| R24Q (R15Q) | 48 | 296 | 55740 |
| R24K (R15K) | 0.85 | 8 | 8550 |
| L26Q (L17Q) | 29 | 162 | 53970 |

TABLE I-continued $K_i$ Values For The Inhibition Of Selected Proteinases By Human TFPI-2, KD1, KD1 Point-Mutants and BPTI.

| Inhibitor | $K_i$ [nM] | | |
|---|---|---|---|
| | Plasmin [30 nM] | Trypsin [50 nM] | FVIIa-TF [50/100 nM] |
| R29A (R20A) | 12 | 52 | 3931 |
| R29D (R20D) | 261 | 4600 | 44600 |
| R29K (R20K) | 5 | 20 | 1115 |
| F42A (F33A) | 79 | 155 | 61186 |
| BPTI | 0.75 | 5 | NI[b] |

[a]Number in parenthesis indicate BPTI numbering system
[b]NI, No Inhibition

Figure 5:
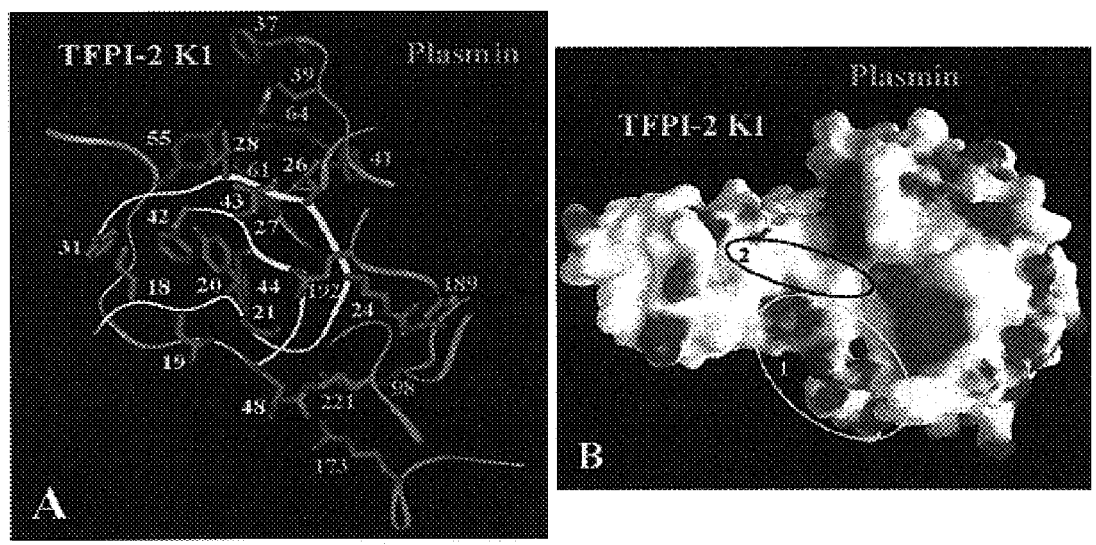
FIG. 5 shows details of the specificity of TFPI-2 KD1 for plasmin. The proteinase domain number of plasmin is based on chymotrypsin numbering. A: Specific interactions between plasmin and TFPI-2 KD1. Red represents oxygen, blue represents nitrogen and green represents carbon atoms. Plasmin is shown with cyan ribbons and TFPI-2 KD1 is shown with yellow ribbons. TFPI-2 KD1 has an acidic patch (Asp19 and Glu48) that interacts with a basic patch on plasmin (Arg644{c98}, Arg719{c173} and Arg767{c221}, where the "c" numbers refer to the analogous positions in chymotrypsin). The $NH_2$ groups of Arg719{c173} in plasmin could make H-bonds with both of the side chain carboxylate groups of Glu48 in TFPI-2 KD1. Gln738{c192} $N_{E2}$ in plasmin appears to make a H-bond with the carbonyl oxygen of Gly21 in TFPI-2 KD1. In addition to these interactions, TFPI-2 KD1 contains a hydrophobic core consisting of Leu18, Tyr20, Tyr31 and Phe42. This hydrophobic core is connected to an interactive hydrophobic patch consisting of Leu26, Leu27, Leu28 and Leu43. This hydrophobic patch in KD1 makes hydrophobic interactions with the $C_B$ of Lys607{c61}, Phe583{c37}, Met585{c39} and Phe587{c41} in plasmin. B: Electrostatic potential between TFPI-2 KD1 and plasmin proteinase domain. The electrostatic potential between TFPI-2 KD1 and plasmin was determined using the program GRASP (Nicholls et al., 1991, Proteins 11, 281-296), and the orientation of the molecules is the same as in A. Blue represents positive, red represents negative, and white represents neutral residues. Region 1 refers to the interactions of the acidic patch on TFPI-2 KD1 (Asp19 and Glu48) and a basic patch on plasmin (Arg644{c98}, Arg719{c173} and Arg767{c221}) described above, and region 2 refers to the hydrophobic interactions between TFPI-2 KD1 and plasmin described above.
Figure 6:
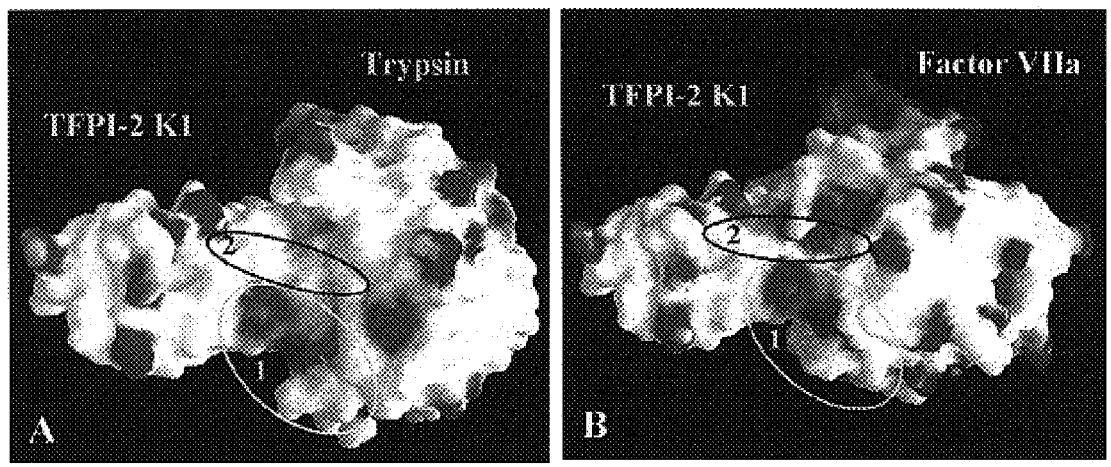
FIG. 6 shows models of the interaction of TFPI-2 KD1 with trypsin and factor VIIa. The orientation of the molecules is the same as FIG. 4. Blue represents positive, red represents negative, and white represents neutral residues. A. Electrostatic potential between TFPI-2 KD1 and trypsin using the program GRASP (Nicholls et al., 1991, Proteins 11, 281-296). Region 1 shows the absence of the interaction between the acidic region (Asp19 and Glu48) of TFPI-2 KD1 and a basic region present in plasmin but absent in trypsin. Instead, this region is acidic in trypsin. Region 2 corresponds to the hydrophobic interactions between TFPI-2 KD1 and trypsin, which is similar to those in the interaction of TFPI-2 KD1 with plasmin. B. Electrostatic potential between TFPI-2 KD1 and factor VIIa determined using the program GRASP (Nicholls et al., 1991, Proteins 11, 281-296). Region 1 shows the absence of the interaction between the acidic region (Asp19 and Glu48) of TFPI-2 KD1 and a basic region, which is present in plasmin but not factor VIIa. Instead, this region is hydrophobic. Region 2 corresponds to the absence of hydrophobic patch interactions between TFPI-2 KD1 and factor VIIa, which are present in both plasmin and trypsin.

In the KD1-proteinase complex, there is an interactive hydrophobic patch and an internal hydrophobic patch in KD1 (FIGS. 5A and 5B). The plasmin-interactive hydrophobic interface is formed by a number of residues in KD1 including Leu26, Leu27, Leu28, Leu43 and Tyr55. The residues Leu18, Tyr20, Tyr31, Phe42 and Tyr44 in KD1 are buried within and contribute to the formation of an internal hydrophobic pocket. Within the interactive patch, Leu27 in KD1 interacts with Phe583{c37}, Met585{c39}, Phe587{c41} and $C_B$ of Lys607{c61} in plasmin (FIGS. 5A and 5B). In addition, Leu28 interacts with Met585{c39} in plasmin. Furthermore, the side chain $C_D$ and $C_E$ of Lys607{c61} could make hydrophobic interactions with $C_{D1}$ and $C_{E1}$ of Tyr55 in KD1 (FIG. 5A). These flanking region interactions at the interface of plasmin and KD1 exhibit a marked variability in structural complementarity when compared to analogous interactions in KD1-trypsin (FIG. 6A) and KD1-factor VIIa (FIG. 6B) complexes. In this regard, the hydrophobic patch observed between KD1 and plasmin does not exist with factor VIIa (FIG. 6B), whereas trypsin appears to have this hydrophobic patch interaction (FIG. 6A). Tyr159{c151} in trypsin is probably involved in hydrophobic interactions with Leu26 and Leu43 of KD1 as is evident from the KD1-trypsin complex. In addition, Phe49{c41} in trypsin is positioned to interact with Leu27 of KD1. We further propose that Lys68{c60} of trypsin may interact with Tyr55 of KD1 and that the side-chain of Lys68{c60} in trypsin may interact with Leu27 via hydrophobic interactions. Finally, there are also main chain interactions between the carbonyl O of Pro22 in KD1 and the amide N of Gly{c216} in serine proteinases, as well as the amide N of Arg24 in KD1 and the carbonyl O of Ser{c214} in serine proteinases. These interactions are common to a serine proteinase interacting with Kunitz-type inhibitors (Janin et al., 1990, J. Biol. Chem. 265, 16027-16030).

Figure 7:
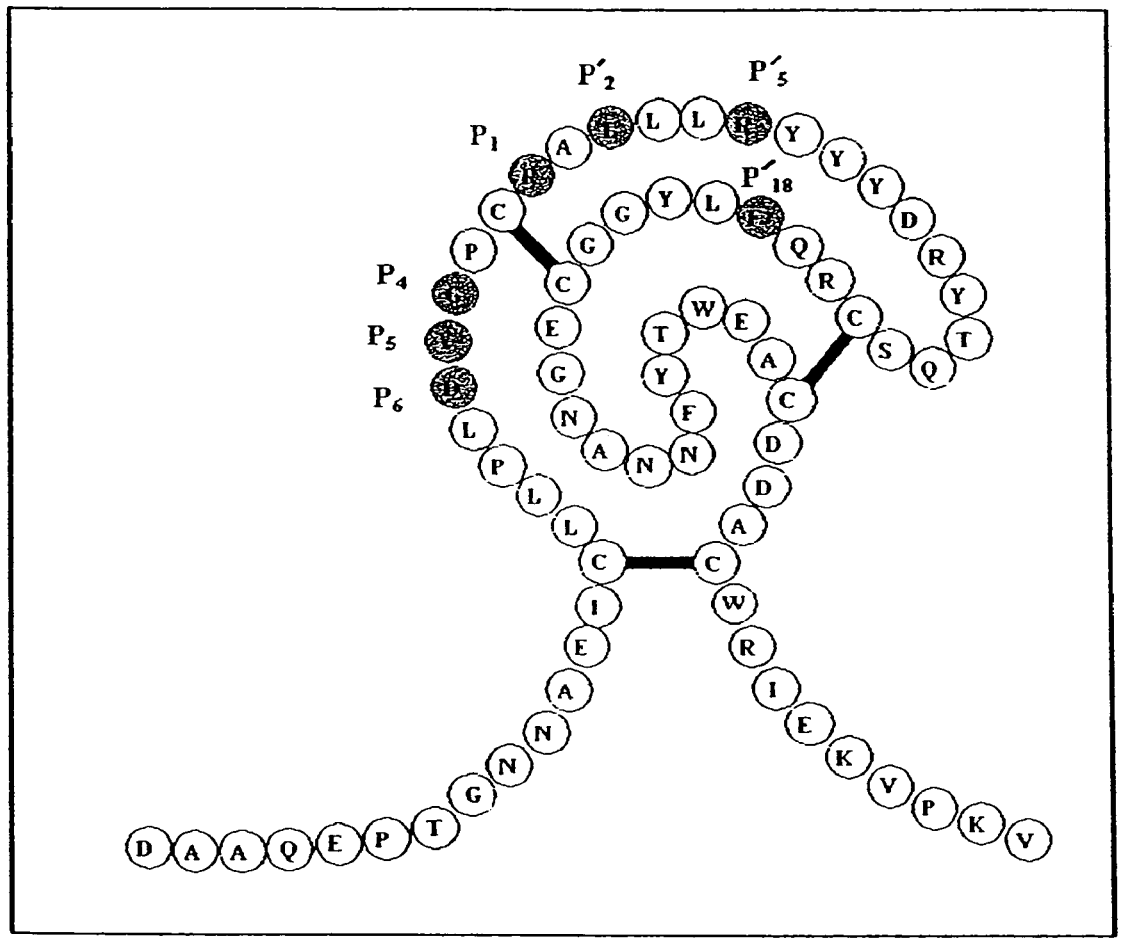
FIG. 7 shows a model structure of the first Kunitz-type domain (KD1) of human TFPI-2 (SEQ ID NO:22). Residues mutated in Example I are shaded.

In addition to hydrophobic interactions, electrostatic attraction/repulsion also plays an important role in forming and stabilizing the KD1-proteinase complex (FIG. 5B). One of the reactive site residues at the $P_6$ position, Asp19, together with Glu48 of the secondary loop, forms an acidic patch in KD1. This acidic patch interacts with a basic patch in plasmin that consists of Arg644{c98}, Arg719{c173}, and Arg767{c221}. Inasmuch as this basic patch is not present in either trypsin or factor VIIa (FIGS. 6A and 6B), we believe that Asp19 in KD1 enhances the specificity of KD1 for plasmin through this electrostatic interaction. Tyr20, the $P_5$ residue, lines the hydrophobic cavity of the internal hydrophobic patch of KD1 and contributes to its structural stability. The following $P_4$ residue, Gly21 is in close proximity spatially to Asp19 and, as observed in the structure $N_{E2}$ of Gln738{c192} in plasmin, makes a hydrogen bond with the backbone C-O of Gly21 in KD1. At the $P_3$ position in KD1, Pro22 is involved in a turn and also fits into a hydrophobic patch in plasmin, trypsin and factor VIIa. Pro22 also sits in the $S_3/S_4$ site of the proteinase. Arg24, the $P_1$ residue, ion pairs with Asp735{c189} at the bottom of the substrate binding pocket in plasmin and is further stabilized through hydrogen bonding to Ser736{c190} Oγ and Gly765{c219}O. Arg29, the highly conserved Arg/Lys at the $P_5'$ of Kunitz-type inhibitors, makes hydrogen bonds with Glu606{c60} in plasmin, and interacts with Tyr67{c59} in trypsin and Asp196{c60} in factor VIIa. Finally, the conserved $P_{18}'$ residue, Phe42 is located in a hydrophobic pocket with Tyr20, Leu18, Tyr31 and Tyr44 in KD1 and probably contributes to the stabilization of the KD1 inhibitory structure. Based on the above molecular modeling studies, KD1 residues Asp 19, Tyr20, Gly21, Arg24, Leu26, Arg29 and Phe42 were selected for mutagenesis. A schematic model representation of the human TFPI-2 KD1 is illustrated in FIG. 7, and highlights residues mutated in this study at the $P_6$, $P_5$, $P_4$, $P_1$, $P_2'$, $P_5'$ and $P_{18}'$.

Preparation and Purification of Human TFPI-2 KD1 and Various KD1 Mutants

Figure 8:
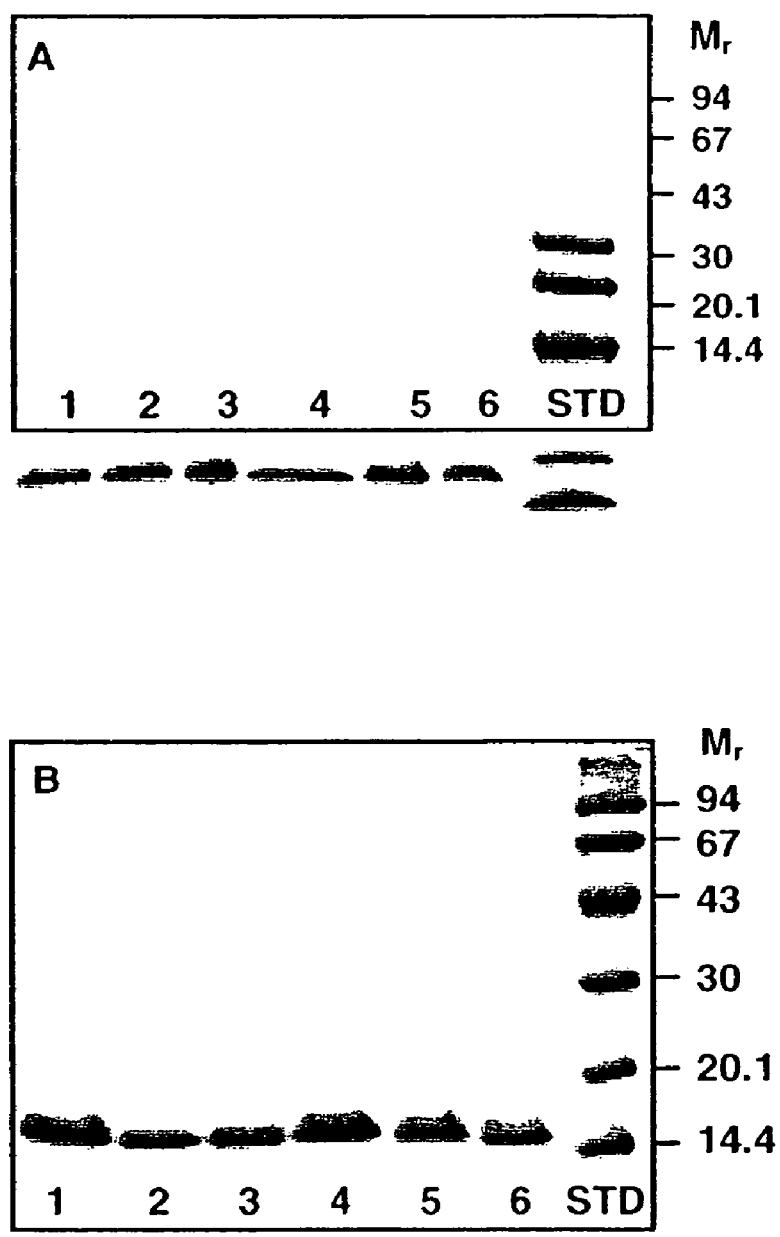
FIG. 8 shows SDS-PAGE of recombinant TFPI-2 KD1 and various KD1 mutants. A: Lane 1, wild-type KD1; lane 2, R24K KD1; lane 3, R24Q KD1; lane 4, R29A KD1; lane 5, R29D KD1; lane 6, R29K KD1; STD, mixture of reduced standard proteins. B: Lane 1, wild-type KD1; lane 2, D19A KD1; lane 3, Y20A KD1; lane 4, G21D KD1; lane 5, L26Q KD1; lane 6, F42A KD1; STD, mixture of reduced standard proteins. Mutant KD1 preparations are designated according to the notation by Shapiro and Vallee (Shapiro, et al., 1989, Biochemistry 28, 7401-7408), in which the single letter code for the original amino acid is followed by its position in the sequence and the single letter code for the new amino acid.

Wild-type and site-specific mutant preparations of human TFPI-2 KD1 were overexpressed as His-tagged fusion proteins in E. coli. The in-frame orientation, integrity and desired mutations in the recombinant constructs were confirmed by nucleic acid sequencing. Each of the recombinant KD1 preparations was expressed and purified from 4 liters of LB broth following induction at 37° C. with 1 mM IPTG. The KD1 preparations obtained from inclusion bodies were solubilized in 6 M guanidine hydrochloride and initially purified on a nickel-charged metal chelating column (His-Trap®), and refolded by sequential dialysis in the presence and absence of reducing agent. The partially purified and refolded KD1 preparations consisted mainly of monomeric KD1 (~70%) with the remainder consisting of KD1 oligomers. Monomeric KD1 was subsequently separated from oligomeric KD1 by Mono Q FPLC. Each of the KD1 preparations migrated as a single band with an average apparent molecular weight of 16 kDa in a denaturing SDS-PAGE gel (FIG. 8). An average yield of 3 mg of purified KD1 was obtained per liter of broth. For each KD1 preparation, the precise molecular weight values were obtained from its amino acid composition, and their mass concentrations were determined spectrophotometrically at 280 nm using a calculated $E^{1\%}$ value based on its Trp, Tyr and Cys content (Gill et al., 1989, Anal. Biochem. 182, 319-326).

Inhibitory Properties of Human TFPI-2 KD1 and Various KD1 Mutants

Recombinant KD1 exhibited stronger inhibitory activity towards each of the three serine proteinases in comparison to the eukaryotically-expressed recombinant full-length TFPI-2 molecule (Table 1), providing strong evidence that the other two Kunitz-type domains of TFPI-2 do not provide any significant effect on TFPI-2's inhibitory properties and that post-translational modifications are not essential for full expression of its inhibitory activity. Wild-type KD1 inhibited plasmin amidolytic activity with roughly a 3-fold higher $K_i$ value than BPTI (Table 1), but was three-fold more potent than full-length TFPI-2. On the other hand, KD1 exhibited approximately two-fold higher trypsin inhibitory activity than full-length TFPI-2, but was two-fold less potent than BPTI (Table 1). Wild-type KD1 inhibited factor VIIa-tissue factor amidolytic activity with a comparable $K_i$ value to that of full-length TFPI-2, while BPTI failed to show any inhibitory activity towards this complex (Table 1). Extra amino acids N-terminal to the mature protein, such as the His-tag region, had little, if any, negative effect on its inhibitory activity. The higher inhibitory activity of the first Kunitz-type domain of TFPI-2 compared to full-length TFPI-2 in all likelihood is attributed to its smaller size and/or flexibility.

The effect of mutations at the $P_6$, $P_5$, $P_4$, $P_1$, $P_2'$, $P_5'$ and $P_{18}'$ are also listed in Table 1. An alanine substitution at the $P_6$ position, Asp19, showed a dramatic (~40-fold) loss of inhibitory activity towards plasmin, but failed to show any significant loss of activity towards trypsin and factor VIIa. From the molecular graphics model, the most rational explanation for this effect is that Asp19 interacts with a basic patch in plasmin consisting of Arg644{c98}, Arg719{c173} and Arg767{c221}. As there are no corresponding basic patches in trypsin or factor VIIa at these positions, the interaction of Asp19 with the basic patch in plasmin appears to confer KD1 with enhanced reactivity, and inhibitory potency, towards plasmin. Mutagenesis of the neighboring $P_5$ residue, Tyr20, to Ala also had a significant negative effect on KD1 inhibition of plasmin, suggesting that this residue either contributes towards the formation of the KD1-plasmin complex, or is critical in maintaining the conformation of the KD1 reactive site towards plasmin. Mutagenesis of Tyr20 to Ala, however, slightly enhanced its ability to inhibit trypsin and factor VIIa (Table 1).

The residue at the $P_4$ position, Gly21, also seems to play a supportive role in the interaction of KD1 with proteinases as shown earlier using BPTI mutants (Grzesiak et al., 2000b, J. Biol. Chem. 275, 33346-33352). In this study, we mutated Gly21 to aspartic acid in order to increase the acidic patch on KD1 and enhance its interaction with the basic patch in plasmin, since Gly21 is in close spatial proximity to Asp19. However, mutation of Gly with Asp did not have the desired effect and this mutant lost inhibitory activity towards all proteinases tested most probably due to perturbation in the main-chain conformation of the KD1 reactive site. In this regard, the phi angle ($\phi$) of Gly is +111° and the psi angle ($\phi$) is -174°, which places Gly21 in a region of the Ramachandran plot accessible only to Gly residues (Creighton et al., 1987, J. Mol. Biol. 194, 11-22). Accordingly, any other residue would conceivably alter the backbone structure by changing the phi and psi angles resulting in an altered main-chain conformation in the vicinity of Gly21.

The side chain of the $P_1$ residue primarily dictates the specificity of a proteinase inhibitor for its cognate proteinase. Systematic substitution at this position in a number of inhibitors revealed a large dynamic range of effects on its association with different proteinases (Castro et al., 1996, Biochemistry 35, 11435-11446; Grzesiak et al., 2000b, J. Biol. Chem. 275, 33346-33352; Ponte et al., 1988, Nature 331, 525-52; Sprecher et al., 1993, Biochemistry 32, 4481-4486; Wun et al., 1988, J. Biol. Chem. 263, 6001-6004; Shimomura et al., 1997, J. Biol. Chem. 272, 6370-6376; Kawaguchi et al., 1997, J. Biol. Chem. 272, 27558-27564; Kaumeyer et al., 1986, Nucleic Acids Res. 14, 7839-7850). The glutamine substitution at the $P_1$ site resulted in a decreased inhibitory activity in KD1 (Table 1), as was observed with the full-length R24Q TFPI-2 mutant (Kamei et al., 1999, Thromb. Res. 94, 147-152). As observed in the model structure of KD1 with plasmin, trypsin and factor VIIa, the Arg24 in KD1 forms a salt bridge, in addition to two hydrogen bonds, with the carbonyl backbone of Asp{c189} and Gly{c219} in order to stabilize the complex. Mutation of Arg to Gln eliminates interaction with the $S_1$ site residue Asp{c189} due to the shorter side chain and its lack of charge. Lysine substitution at this position restores the inhibitory activity of KD1, and the lower $K_i$ values obtained with R24K KD1 against plasmin and trypsin could be the result of an ionic interaction of the protonated amino group with the carboxylate group of Asp{c189}, as well as water-mediated hydrogen bonding between the carbonyl group of Gly{c219} and the hydroxyl group of Ser{c190} with the $P_1$ Lys amino group. In view of this potential bonding pattern, it is curious as to why the inhibitory activity of R24K KD1 for factor VIIa was reduced approximately five-fold, inasmuch as factor VIIa also has a Ser326{c190}. The reason for its reduced inhibitory activity against factor VIIa is not known at this point, but may be due to other residues in the substrate binding pocket of factor VIIa as opposed to that of plasmin and trypsin.

As mentioned above, KD1 contains a cluster of hydrophobic Leu residues at the $P_2'$-$P_4'$ region that interacts with a hydrophobic patch in plasmin, trypsin and factor VIIa. In order to disrupt this cluster, Leu26 was substituted with the highly hydrophilic residue, glutamine. This L26Q mutation resulted in at least a 10-fold reduction in inhibitory potency of KD1 towards each of the proteinases tested (Table 1) and underscores the importance of this hydrophobic interaction in the inhibitory mechanism of KD1. Leu26 is part of a hydrophobic patch and interacts with Leu43 and Leu28 of KD1. Leu26 also has the potential to have hydrophobic interactions with Gln738{c192} in plasmin, with $C_D$ and $C_G$ of Gln200{c192} in trypsin, and with $C_D$ and $C_G$ of Lys328{c192} in factor VIIa. Thus, changing this residue to a non-hydrophobic residue such as Gln will disrupt these interactions and be disruptive for each proteinase.

Virtually all Kunitz-type domains studied have a highly conserved Lys/Arg at the $P_5'$ position (FIG. 4), and three point mutants were made at this position. In plasmin, Glu606{c60} makes hydrogen bonds with Arg29 in KD1, whereas Tyr67{c59} and Asp196{c60} in trypsin and factor VIIa, respectively, interact with this residue. Substitution of Arg29 with alanine resulted in a marginal loss of inhibitory activity towards all three proteinases (Table 1), whereas substitution with aspartic acid presumably caused charge repulsion, as well as disruption of hydrogen bonds, with a major effect on $K_i$ (Table 1). Mutation of Arg29 with lysine could possibly preserve the hydrogen bonding observed with Arg and resulted in minor changes in $K_i$ (Table 1). While the $P_5'$ Arg/Lys residue is important in the inhibitory mechanism of KD1, it does not appear to be a major determinant in KD1 specificity.

Finally, as expected, mutagenesis of the highly conserved Phe42 at the $P_{18}'$ position with alanine resulted in similar losses of inhibitory activity towards all three proteinases (Table 1), presumably by disruption of the internal hydrophobic core in KD1 formed by Phe42, Tyr20, Leu 18, Tyr31, Tyr44 and the side chain of Arg29.

Discussion

In the present study, we have expressed and purified the human TFPI-2 Kunitz-type domain 1 (KD1), and compared its inhibitory activity towards plasmin, trypsin and the factor VIIa-tissue factor (VIIa-TF) complex to that of full-length TFPI-2, BPTI, and nine human TFPI-2 KD1 constructs with mutations in the reactive site region ($P_6$-$P_5'$). The isolated TFPI-2 KD1 exhibited stronger inhibitory activity towards these proteinases in comparison to intact TFPI-2. Alanine substitution at the $P_6$ (D19A) and the $P_5$ (Y20A) positions had a marginal effect on its inhibitory activity towards trypsin and VIIa-TF, but exhibited a marked decrease in activity towards plasmin. Substitution of aspartic acid for alanine was particularly deleterious to plasmin inhibition by KD1 and molecular modeling studies revealed that this was in all likelihood due to the modulation of an ionic interaction between an acidic patch in KD1, formed by Asp 19 and Glu39, and a basic patch unique to plasmin composed of Arg644{c98}, Arg719{c173} and Arg767{c221}. Thus, Asp19 and Tyr20 in KD1 appear to play a major role in the specificity of TFPI-2 for plasmin. In contrast, point mutations at the $P_4$(G21D), $P_1$(R24Q), $P_2'$ (L26Q) and $P_5'$ (R29A) positions all exhibited substantial decreased inhibitory activity towards all of these proteinases. The importance for a highly conserved basic residue (Arg/Lys) at the $P_5'$ position was evident from a substantial loss of inhibitory activity in the R29D KD1, presumably through the loss of either a stabilizing ionic interaction between Arg29 and Glu606/Asp196{c60} in plasmin/VIIa, or by hydrogen bonding of Arg29 to Tyr67{c59} in trypsin. Finally, mutation of a highly conserved phenylalanine at the $P_{18}'$ position (F42A) revealed the importance of this residue in the stabilization of the reactive site structure through internal hydrophobic interactions.

A lysine substitution at the $P_1$ position (R24K) in KD1 significantly increased its inhibitory activity towards both plasmin and trypsin, making it essentially as effective as BPTI towards these proteinases. In sharp contrast, R24K KD1 paradoxically exhibited approximately a five-fold reduction in inhibitory activity towards VIIa-TF, a somewhat surprising result in consideration of the fact that VIIa contains a Ser326{c190} that forms an additional water-mediated hydrogen bond with the protonated 6-amino group in lysine (Bode et al., 2000, Biochim. Biophys. Acta 1477, 241-252) and that VIIa forms a stable interaction with the first Kunitz-type domain of TFPI through its interaction with a $P_1$ lysine residue. On the other hand, BPTI also contains a lysine in its $P_1$ position and failed to inhibit VIIa-TF (Table 1), suggesting that VIIa prefers Arg $P_1$ residues and that other residues in the reactive site region of TFPI-2 KD1 somehow synergistically enhance VIIa inhibition, as has been shown for a BPTI mutant (Zhang et al., 1999, J. Mol. Biol. 285, 2089-2104).

Of potential clinical relevance, R24K KD1 exhibited essentially the same inhibitory activity as BPTI, which is widely used as a plasmin inhibitor during surgery but, being of bovine origin, precipitates episodes of severe anaphylaxis on some occasions (0.5-1%). In this context, these studies may provide a template for the design of improved Kunitz-type serine proteinase inhibitors with considerable therapeutic potential. In this regard, our laboratory, and other laboratories, have demonstrated the importance of serine proteinase inhibition in the growth, migration, angiogenesis and metastasis of a variety of human tumors (Chand et al., 2004, Blood 103, 1069-1077; Epub 2003 Oct. 2, Example III; Soff et al., 1995, J. Clin. Invest. 96, 2593-2600; Konduri et al., 2001, Oncogene 20, 6938-6945; Kobayashi et al., 2004, Cancer 100, 869-877).

These tumor properties are presumably mediated in large part by proteinases such as plasmin and/or trypsin IV (Cottrell et al., J. Biol. Chem. 279: 13532-13539, 2004), and the secretion of inhibitory TFPI-2 by these tumors markedly inhibits their growth and metastasis in animal models (Chand et al., 2004, Blood 103, 1069-1077; Epub 2003 Oct. 2; Example III; Konduri et al., 2001, Oncogene 20, 6938-6945). Moreover, in preliminary studies, we have shown that hexa-histidine tagged-human KD1 exhibits dose-dependent inhibition of angiogenesis in a commercially available in-vitro human endothelial cell angiogenesis assay (see Example VI). In addition, intravenous administration of human KD1 to ovalbumin-sensitized asthmatic mice resulted in a significant decrease in the number of airway macrophages and lymphocytes relative to vehicle-treated asthmatic mice, suggesting that KD1 inhibits the proteinase-mediated transepithelial migration of mononuclear cells from the bloodstream to the airways (see Example IV). Accordingly, administration of KD1, or a more potent KD1 mutant, may conceivably regulate these and other pathological processes dependent upon the activity of serine proteinases. In addition, the availability of human KD1 generated in these studies will facilitate X-ray crystallographic studies of either this inhibitor alone or in complex with serine proteinases, and these studies are currently ongoing in our laboratories.

In summary, these studies provide the initial, definitive evidence that the first Kunitz-type domain of human TFPI-2 contains all the structural elements for the inhibition of a variety of serine proteinases, and underscores the importance of critical residues in its $P_6$-$P_5'$ position in its inhibitory activity towards these proteinases. In addition, these studies reveal the importance of the Asp and Tyr residues at the $P_6$ and $P_5$ positions in the reactive site region of KD1 that appears to confer specificity for plasmin inhibition by TFPI-2.

Example II

Purification of R24K-KD1

Materials

*Escherichia coli* strain BL21 (DE3) and pET28a expression vector were products of Novagen Inc. (Madison, Wis.). The QuickChange® site-directed mutagenesis kit was obtained from Stratagene (La Jolla, Calif.). YM3 ultrafiltration membranes were purchased from Millipore (Bedford, Mass.). His-Trap®☐ columns were obtained from Amersham Biosciences Corp. (Piscataway, N.J.). Novex 4-20% Tris-glycine polyacrylamide gels were purchased from Invitrogen (Carlsbad, Calif.). All other reagents were the highest purity commercially available.

Expression and Purification of R24K-KD1

The R24K mutant of the first Kunitz-type domain of human TFPI-2 (KD1) was overexpressed as N-terminal histidine (His)-tagged fusion protein in *Escherichia coli* strain BL21 (DE3) using the T7 promoter system. The recombinant plasmid derived from pET28a bearing a hexa-histidine leader sequence followed a thrombin cleavage site and cDNA encoding the first Kunitz-domain of TFPI-2 was prepared according to standard procedures (Sambrook et al., 2001, Molecular Cloning: A laboratory Manual, Third Edition, Cold Spring Harbor Laboratory Press, Cold Spring Harbor, Me.). Using this recombinant vector as a template, a R24K-KD1 mutant construct was generated using a QuickChange® site-directed mutagenesis kit according to the manufacturer's instructions. The recombinant construct was examined for in-frame orientation, integrity and desired mutation by nucleic acid sequencing. The 6-His-tag R24K-KD1 fusion protein was expressed in *E. coli* grown in rich media containing 100 mg/L ampicillin (Sigma Chemical Company, St. Louis, Mo.), and induced at 37° C. with 1 mM isopropyl thiogalactopyranoside (IPTG, Gold Biotechnologies Inc., St. Louis, Mo.) at mid log-phase ($A_{600}$=0.4-0.7).

The induced cells were harvested and lysed using a lysozyme-nucleotidase mix, 0.2% Lysozyme (Sigma Chemical Company, St. Louis, Mo.), 20 µg/ml DNase I (Sigma) & 20 µg/ml RNase A (Sigma Chemical Company, St. Louis, Mo.) in 10 mM Tris-HCl (pH 7.5) containing 150 mM NaCl, 1 mM $MgCl_2$, 1 mM PMSF. Cell lysis was carried out at room temperature for 2 hour and the lysate was subjected to centrifugation (20000×g for 15 minutes). The cell pellet was then resuspended in a detergent solution, 3% Igepal® CA-630 (MP Biochemicals LLC, Aurora, Ohio) in 10 mM Tris-HCl (pH 7.5) and 1 mM EDTA, sonicated at 50% power (Sonicator®, Heat Systems Ultrasonic Inc., W-380 model) and inclusion bodies were collected by centrifugation (20000×g for 15 minutes). The inclusion bodies were then washed twice with water following brief sonication and centrifugation (20000×g for 15 minutes). The highly enriched inclusion bodies were then solubilized overnight in 50 mM Tris-HCl (pH 8.0) containing 7 M urea, 0.5 M NaCl and 10 mM 2-mercaptoethanol. The suspension was centrifuged at 20000×g for 3 hour, the supernatant was filtered (0.2µ filters) and subsequently loaded onto a nickel-charged His-Trap column (Amersham Bioscience, Piscataway, N.J.). The column was washed with the equilibration buffer (50 mM Tris-HCl (pH 8.0) containing 7 M urea, 0.5 M NaCl and 10 mM 2-mercaptoethanol), followed by equilibration buffer containing 25 mM imidazole. The 6-His-Tag R24K-KD1 fusion protein was eluted from the column in equilibration buffer containing 500 mM imidazole.

The His-Trap purified protein was reduced by the addition of 50 mM dithiothreitol (Sigma Chemical Company, St. Louis, Mo.). This solution was incubated overnight with rocker-shaking at room temperature and then diluted to a concentration of ~0.5 mg/ml in 50 mM Tris-HCl (pH 9.5) containing 6 M urea and 0.02% azide, and dialyzed against 20 volumes of the same buffer at room temperature. The refolding was then carried out by dialyzing against 50 mM Tris-HCl (pH 9.0) containing 0.3 M NaCl, 2 M urea, 2.5 mM GSH, 0.5 mM GSSG and 0.02% azide (buffer A). The dialysis was performed for 48 hour at 4° C. The sample was then dialyzed against fresh buffer A for another 48 hour at 4° C. The solution was then dialyzed at 4° C. against 50 mM Tris-HCl (pH 9.0) containing 1 M urea followed by extensive dialysis against 50 mM Tris-HCl (pH 9.0) at 4° C.

The refolded protein solution was then filtered (0.2µ filters) and applied to a Q-Sepharose (Pharmacia Biotech) column equilibrated at 4° C. with 50 mM Tris-HCl (pH 9.0). The protein was eluted from the column using a linear 0-1 M NaCl gradient and the fractions were analyzed on SDS-PAGE. The R24K-KD1-containing fractions were pooled and digested with human thrombin (Kisiel et al., Blood. 1985; 66(6):1302-8)) at a 1:1000 enzyme:substrate molar ratio for 6 hour at room temperature. The digestion was confirmed by SDS-PAGE analysis of temporal aliquots. His-Tag-free R24K-KD1 preparations were then applied on His-Trap columns to remove the hexa-histidine peptides followed by SP-Sepharose (Pharmacia Biotech) chromatography equilibrated with 50 mM MES (pH 6.0) buffer, to remove traces of thrombin. The pure, His-Tag-free R24K-KD1 preparations were then dialyzed extensively against 20 mM Tris-HCl (pH 7.5), concentrated to >10 mg/ml (Amicon Ultra-15, 5000 MWCO, Millipore), and stored at −80° C. Each batch preparation was characterized with respect to protein concentration ($A_{280}$), purity (SDS-PAGE analysis) and inhibition kinetics as described in Example I (see also Chand et al., J. Biol. Chem. 2004; 279(17):17500-7; Epub 2004 Feb. 16. Erratum in: *J Biol. Chem.* 2004; 279(23):24906).

Example III

The Effect of Human Tissue Factor Pathway Inhibitor-2 on the Growth and Metastasis of Fibrosarcoma Tumors in Athymic Mice Summary Human tissue factor pathway inhibitor-2 (TFPI-2) is a matrix-associated Kunitz inhibitor that inhibits the plasmin and trypsin-mediated activation of zymogen matrix metalloproteinases involved in tumor progression, invasion and metastasis. To directly assess its role in tumor growth and metastasis in-vivo, we stably-transfected HT-1080 fibrosarcoma cells expressing either fully active wild-type human TFPI-2 (WT) or inactive R24Q TFPI-2 (QT), and examined their ability to form tumors and metastasize in athymic mice in comparison to mock-transfected cells (MT). MT and QT fibrosarcoma tumors grew 2-3 times larger than WT tumors. Tumor metastasis was confined to the lung and was observed in 75% of mice treated with either MT- or QT-cells whereas only 42% of mice treated with WT-cells developed lung metastases. Real time quantitative RT-PCR analyses of each tumor group revealed 3-6-fold lower levels of murine vascular endothelial growth factor gene expression in WT tumors in relation to either MT or QT tumors. Comparative tumor gene-expression analysis revealed that several human genes implicated in oncogenesis, invasion and metastasis, apoptosis and angiogenesis had significantly altered levels of expression in WT-tumors. Our collective data demonstrate that secretion of inhibitory TFPI-2 by a highly metastatic tumor cell markedly inhibits its growth and metastasis in-vivo by regulating pericellular ECM remodeling and angiogenesis.

Introduction

Proteolytic degradation of the extracellular matrix (ECM) is considered to be an essential step for malignant cells to invade and metastasize to distant tissues (Dano et al., Adv. Cancer Res. 1985; 44:139-239; Mignatti et al., Physiol. Rev. 1995; 73:161-195). Proteinase inhibitors capable of protecting the ECM from degradation by tumor-derived proteinases could potentially find utility as therapeutic agents for blocking tumor metastasis. Human tissue factor pathway inhibitor-2 (TFPI-2) is a Kunitz-type serine proteinase inhibitor synthesized and secreted into the ECM by endothelial cells, smooth muscle cells, fibroblasts, keratinocytes and urothelium (Iino et al., Arter. Thromb. Vasc. Biol. 1998; 18:40-46; Herman et al., J. Clin. Invest. 2001; 107:1117-1126; Rao et al., Arch. Biochem. Biophys. 1995; 104: 311-314; Rao et al., J. Invest. Dermatol. 1995; 104:379-383; Deng et al., Proc. Natl. Acad. Sci. USA 2001; 98:154-159). TFPI-2 readily inhibits trypsin, plasmin, chymotrypsin, cathepsin G, plasma kallikrein and the factor VIIa-tissue factor complex, but not urokinase-type plasminogen activator (uPA), tissue-type plasminogen activator or thrombin (Sprecher et al., Proc. Natl. Acad. Sci. USA 1994; 91:3353-3357; Petersen et al., Biochemistry 1996; 35:266-272; Miyagi et al., J. Biochem. 1994; 116:939-942; Rao et al., Arch. Biochem. Biophys. 1996; 335:45-52). TFPI-2 presumably inhibits these proteinases through an arginine residue (R24) in its first Kunitz-type domain, as an R24Q TFPI-2 mutant lost >90% of its inhibitory activity towards trypsin, plasmin and the factor VIIa-tissue factor complex (Kamei et al., Thromb. Res. 1999; 94:147-152). TFPI-2 also strongly inhibited the trypsin or plasmin-mediated activation of promatrix metalloproteinases proMMP-1 and proMMP-3, and suppressed production of active MMP-2 in HT-1080 cells stably-transfected with the TFPI-2 expression vector (Rao et al., Biochem. Biophys. Res. Commun. 1999; 255:94-99; Izumi et al., FEBS Lett. 2000; 481:31-36). In addition, TFPI-2 expression is upregulated in human atherosclerotic coronary arteries in comparison to normal, healthy arteries (Crawley et al., Arterioscler. Thromb. Vasc. Biol. 2002; 22:218-224). Thus, ECM-associated TFPI-2 may play a pivotal role in the regulation of ECM remodeling, a process essential for tumor invasion and metastasis.

Given the inhibitory spectrum of TFPI-2, as well as our previous finding that TFPI-2 inhibited the degradation of fibroblast-derived ECM and Matrigel invasion by the highly invasive HT-1080 fibrosarcoma cell in a dose-dependent fashion (Rao et al., Int. J. Cancer 1998; 75:749-756), we hypothesized that expression of TFPI-2 by HT-1080 cells would markedly reduce its invasive and metastatic properties in an animal model. Since HT-1080 cells do not constitutively synthesize TFPI-2 (Rao et al., Int. J. Cancer 1998; 75:749-756), we prepared stably-transfected HT-1080 cells expressing high concentrations of wild-type human TFPI-2. We demonstrate that, in athymic mice, HT-1080 cells expressing wild-type TFPI-2 produce considerably smaller subcutaneous tumors and exhibited a lower metastatic rate in comparison to mock-transfected HT-1080 cells. Furthermore, HT-1080 cells stably transfected with an expression vector coding for an inactive mutant of TFPI-2, R24Q TFPI-2, produced tumors in size and metastatic rate similar to mock-transfected HT-1080 cells, providing strong evidence that the ability of TFPI-2 to reduce tumor size and metastasis correlated with its serine proteinase inhibitory activity.

Materials and Methods

Materials

The murine myeloma cell line P3×63Ag8U.1 (P3U1) and the human fibrosarcoma cell line HT-1080 were obtained from American Type Tissue Culture Collection (Rockville, Md.). Minimum essential medium Eagle (EMEM), non-essential amino acid solution, trypsin/EDTA solution, RPMI-1640, TMBZ (3,3',5,5'-tetramethylbenzidine), and avidin-peroxidase were from Sigma Chemical Company (St. Louis, Mo.). Lipofectamine plus reagent, sodium pyruvate, penicillin-streptomycin, and PBS were obtained from Gibco BRL Life Technologies, (Rockville, Md.). pcDNA3 vector and proteinase K were obtained from Invitrogen (Carlsbad, Calif.). 5'-bromo-2'-deoxyuridine (BrdU) and monoclonal antibody to BrdU were obtained from Amersham Pharmacia Biotech (Piscataway, N.J.). Histomouse™-SP bulk kit was purchased from Zymed Laboratories (South San Francisco, Calif.). ApopTag®-Peroxidase In-Situ Apoptosis Detection Kit was obtained from Serological Corporation (Norcross, Ga.). The TaqMan® RT reagent kit and the SYBR® Green Master Mix were obtained from Applied Biosystems (Foster City, Calif.). Recombinant human TFPI-2 was purified as described (Sprecher et al., Proc. Natl. Acad. Sci. USA 1994; 91:3353-3357). All other reagents used were the highest quality commercially available.

Antibodies

Rabbit anti-human TFPI-2 IgG was prepared as described (Iino et al., Arter. Thromb. Vasc. Biol. 1998; 18:40-46). Murine monoclonal antibodies against human TFPI-2 were prepared as follows. Six-week-old female Balb/c mice were injected intraperitoneally (IP) on day 0 with 50 µg recombinant TFPI-2 suspended in 50 µl of a PBS/Freund's Complete Adjuvant emulsion. Subsequent injections containing 50 µg of TFPI-2 and Freund's Incomplete Adjuvant were administered IP on days 14 and 35. Mice were given an intravenous boost on days 49, 53 and 56, and sacrificed on day 59. One mouse expressing the highest serum titer ($>10^5$) of anti-TFPI-2 antibodies was sacrificed and its splenocytes fused with P3×63Ag8U.1 myeloma cells. Fusion and hybridoma selection were optimized using standard methodology (Lane et al., Cancer Epid. Biomark. Prev. 2002; 11:809-814). Hybridomas were cultured for seven days and their supernatants screened for antibodies to TFPI-2 by ELISA. Wells considered positive ($A_{405}>1$) were weaned from HAT supplement over 7-10 days, subcloned by limiting dilution, and grown in pristane-primed mice to generate ascites fluid. Monoclonal antibodies to human TFPI-2 (SK8, SK9) were isolated from ascites fluid using Hi Trap® rProtein A affinity columns.

Cell Culture and Transfection

HT-1080 cells were cultured in 6% $CO_2$-94% air and 96% humidity at 37° C. in EMEM supplemented with 10% bovine calf serum (Hyclone, Logan, Utah), sodium pyruvate, nonessential amino acids, L-glutamine, and penicillin-streptomycin. The human TFPI-2 (Sprecher et al., Proc. Natl. Acad. Sci. USA 1994; 91:3353-3357) and R24Q TFPI-2 (Kamei et al., Thromb. Res., 1999, 94:147-152) cDNA were directionally subcloned into the EcoRI site of the pcDNA3 expression vector and the recombinant constructs transfected into HT-1080 cells using the Lipofectamine Plus reagent according to the manufacturer's instructions. Selection of transfected cells with 0.6 mg/ml G418 sulfate (Clontech, Palo Alto, Calif.) was initiated 48 hrs post-transfection and resistant colonies were cloned thrice by limiting dilution, screened for TFPI-2 expression by ELISA, and expanded. The expression levels of wild-type and R24Q TFPI-2 in stably-transfected cells were assessed over a six week period in the presence and absence of G418.

Cell Proliferation

Transfected HT-1080 cells were plated in duplicate at a density of $1\times10^5$ cells/well in a six-well plate. Every seven days, for a total of 42 days, the cells were trypsinized, counted, and replated at the same seeding density.

Human TFPI-2 ELISA

The concentration of wild-type and R24Q human TFPI-2 antigen in stably-transfected HT-1080 cell supernatants was determined by ELISA using monoclonal antibody SK9 and biotinylated monoclonal antibody SK8. In this procedure, 96-well microtitration plates were coated overnight at 4° C. with 100 µl/well of 50 mM carbonate buffer (pH 9.6) containing 10 µg/ml SK9. After washing the plate three times with TBS/0.05% Tween 20, each well was blocked with 200 µl of TBS/1% gelatin/0.02% $NaN_3$ at 37° C. for 2 hours. Following five washes with TBS/Tween, 100 µl samples were added to each well and allowed to incubate at 37° C. for 2 hours. The plate was then washed five times with TBS/Tween and 100 µl of biotinylated SK-8 (100 ng/ml in TBS/0.1% BSA) was added to each well. After 2 hours incubation at 37° C., the plate was washed five times with TBS/Tween and subsequently treated with 100 µl of diluted peroxidase-conjugated avidin for 1 hour. After washing with TBS/Tween, each well was treated with 100 µl of tetramethyl benzidine solution. Following a suitable color development, the reaction was stopped by the addition of 1 N $H_2SO_4$ (100 µl) and the absorbance measured at 450 nm. The concentration of TFPI-2 in test samples was interpolated from a linear standard curve (linear range 6-200 ng TFPI-2) relating $A_{450}$ and known concentrations of recombinant human TFPI-2.

Tumor Growth and Metastasis

All animal procedures were approved by the University of New Mexico Health Sciences Center Laboratory Animal Care and Use Committee. Thirty-six, six week old Balb/c SCID male mice, obtained from Charles River Laboratory (Frederick, Md.) through the NCI Contract Animal Program, were fed and watered ad libitum. The mice were divided into three groups of twelve, and each mouse was injected $5\times10^6$ HT-1080 cells subcutaneously (SQ). Group I was administered mock-transfected HT-1080 cells (MT), group II with wild-type TFPI-2 transfected HT-1080 cells (WT), and group III with R24Q TFPI-2 transfected HT-1080 cells (QT). The subcutaneous growth of tumors was readily visible, and the volume (0.5×length×width$^2$) of each tumor was measured externally by a tumor caliper. Five weeks post-injection, each mouse received an intraperitoneal injection of BrdU (100

μg/g body mass) and was sacrificed 3 hrs later by $CO_2$ narcosis. At sacrifice, the mice were weighed, and visible tumors and several organs were aseptically removed for further analyses.

Tissue Processing

Harvested tumors and organs were formalin-fixed and paraffin-embedded using standard procedures. The organ tissues were visually inspected for the presence of metastatic tumors throughout the procedure. The embedded organ and tumor tissues were sectioned (5μ) for subsequent hematoxylin and eosin (H&E) staining and further analyses.

Immunohistochemical Detection of TFPI-2

Sections were deparafinnized with xylene, rehydrated in a graded series of ethanol, and washed in PBS for immunohistochemical staining. Expression of wild-type or R24Q TFPI-2 was determined using rabbit anti-human TFPI-2 IgG and detected using the Histomouse™-SP Bulk kit according to the manufacturer's instructions. Briefly, rehydrated slides were incubated with 3% $H_2O_2$ to quench endogenous peroxidase activity, blocked, incubated overnight (4° C.) with antibody (1:000 dilution in PBS), followed by incubation with a biotinylated secondary antibody, developed and counterstained with hematoxylin.

Detection of BrdU-Labeled and Apoptotic Cells

Tumor sections were processed as described above with an additional step of trypsin (1 μg/μl) treatment after quenching. The cells were probed by incubation with primary anti-BrdU antibody (1:10 dilution) in nuclease solution. The apoptotic cells in sections were detected by TUNEL staining using the in-situ apoptosis detection kit (Apoptag® Peroxidase Kit) according to the manufacturer's instructions. Briefly, after deparaffinization, the sections were treated with proteinase K (20 μg/ml) for 15 min at room temperature and blocked. The sections were then treated with TdT enzyme for 60 min at 37° C. Anti-digoxigenin peroxidase-conjugate was applied for 30 min at RT, and was detected with the aforementioned substrate-chromogen solution. BrdU-labeled and TUNEL-positive cells were determined by counting five randomly-chosen areas (100×) in each section and averaged from three sections.

Microdissection and DNA Amplification

The cells from sections were microdissected and cellular DNA purified as described (Bernstein et al., Cancer Epid. Biomark. Prev. 2002; 11:809-814). For each group, three 5μ sections were deparaffinized and air dried. Under a dissecting microscope, the regions of interest were microdissected and collected. Fixed control mouse stomach and lung cells were also processed similarly. The microdissected tissue was lysed overnight at 50° C. in 50 μl of buffer containing 50 mM Tris-HCl (pH 8.5)/1 mM EDTA/0.5% Tween 20/200 μg/ml proteinase K, followed by proteinase K inactivation at 95° C. (10 minutes). The cellular DNA obtained was ethanol precipitated, washed, air-dried and redissolved in 10 μl of ADW. An aliquot (3 μl) of each was analyzed for human mitochondrial DNA (mt DNA) and the recombinant vector construct (rvcDNA) by PCR. The amplification of human mt DNA (1071 bp fragment) utilized a forward primer (GCT ATT ACC TTC TTA TTA TTT ACC; SEQ ID NO:23) and reverse primer (GTG CGA TGA GTA GGG GAA GG; SEQ ID NO:24). For the amplification of rvcDNA (700 bp fragment), a forward T7 primer (TAA TAC GAC TCA CTA TAG GG; SEQ ID NO:25) and a TFPI-2-specific reverse primer (GCC TCG AGT TAA AAT TGC TTC TTC CGA TA; SEQ ID NO:26) were employed. The thermocycling profile was set as 5 minutes of initial denaturation at 94° C., followed by 39 cycles of denaturation (94° C. for 30 seconds), annealing for 1 minute (54° C. for rvcDNA; 57° C. for human mtDNA), and elongation (72° C. for 2 minutes). The reaction products were electrophoresed in a 1.2% agarose gel along with appropriate DNA markers.

RNA Isolation

Total RNA was isolated from snap-frozen tumor samples (100-150 mg) using an RNeasy RNA extraction kit (Qiagen, Chatsworth, Calif.), according to the manufacturer's recommendation. Purified RNA samples were stored at −80° C. in 100 μl of DEPC-treated water. An aliquot of each RNA preparation was analyzed and quantitated using the RNA 6000 Nano assay kit in an Agilent Technologies 2100 Bioanalyzer.

VEGF Expression: Real Time Quantitative RT-PCR

A two-step real time quantitative RT-PCR analysis was performed using a SYBR® Green-dye based assay in an ABI Prism® 7000 Sequence Detection System according to the manufacturer's instructions. Total RNA (300 ng) from each sample was reverse-transcribed using random hexamer primers (TaqMan® RT reagents kit). Primers targeting the angiogenesis marker murine VEGF and murine GAPDH, an internal control, were designed using Primer Express software. The primers selected for sense and antisense strand respectively are; mouse VEGF cDNA (GenBank accession number S38083): TTACTGCTGTACCTCCACC (SEQ ID NO:27) and ACAGGACGGCTTGAAGATG (SEQ ID NO:28); mouse GAPDH cDNA (GenBank accession number M32599): AACGACCCCTTCATTGAC (SEQ ID NO:29) and TCCACGACATACTCAGCAC (SEQ ID NO:30). To assure the amplicon specificity of each primer set, the PCR products were subjected to a melting curve analysis and subsequent agarose gel electrophoresis. The PCR reaction was performed in triplicates using the SYBR® Green Master Mix in a total volume of 50 μl. The reaction mixture was incubated at 95° C. for 10 minutes followed by a cycling profile of 45 cycles consisting of denaturation at 95° C. for 9 seconds, annealing at 57° C. for 9 seconds, and extension at 72° C. for 30 seconds. The efficiency for amplification of the target gene (VEGF) and the internal control gene (GAPDH) was examined using serial dilutions of cDNA with gene-specific primers. The mean difference between threshold cycle number values ($\Delta C_T$) was calculated for each cDNA dilution. The VEGF gene expression level in each sample was calculated following normalization to the GAPDH gene level and expressed as relative units.

Tumor cDNA Microarray Analysis

The relative mRNA abundance in the snap-frozen tumor xenograft samples was assessed by oligonucleotide-based microarray analysis using an Affymetrix GeneChip® Human Genome U133 set. This GeneChip® consists of two array units of over one million unique oligonucleotide features covering over 39,000 transcript variants that represent 33,000 of the best characterized human genes. Additional information regarding these chips is available on-line at HYPERLINK "http://www.affymetrix.com/products/arrays/specifc/hgen133.affx." Biotinylated cRNA probe preparation, processing, hybridization and normalization were performed as described in the Affymetrix GeneChip® Expression Analysis Manual. Florescence images were captured using a gene array scanner (Affymetrix) and expression analysis was performed using GeneSpring v5.1 software. The wild-type TFPI-2 transfected (WT) tumor ratio of medians was normalized with that obtained from mock-transfected (MT) tumors. The spots that exhibited a 2-fold or greater difference in expression levels were used to generate the gene clusters.

Results

Characterization of Stably-Transfected HT-1080 Cells

HT-1080 cells were stably transfected with the eukaryotic expression vector pcDNA3 alone (MT-1080), or containing cDNA constructs for either wild-type TFPI-2 (WT-1080) or R24Q TFPI-2 (QT-1080). TFPI-2-expressing stably transfected tumor cells were cloned by limiting dilution resulting in several cell lines secreting different levels of TFPI-2 that ranged from 10-55 ng/ml/day/$10^6$ cells determined by ELISA and consisted of three differential glycosylated forms of TFPI-2 (Mr 32 kDa, 29 kDa, and 26 kDa), similar to that observed for human endothelial and smooth muscle cells (Iino et al., Arter. Thromb. Vase. Biol. 1998; 18:40-46; Herman et al., J. Clin. Invest. 2001; 107:1117-1126; Rao et al., Arch. Biochem. Biophys. 1995; 104: 311-314; Rao et al., J. Invest. Dermatol. 1995; 104:379-383). The TFPI-2-secreting HT-1080 cell lines selected for these studies secreted ~55 ng/ml/day/$10^6$ cells, but this number most likely underestimates the amount of TFPI-2 secreted by these cells into their ECM in-vivo. In this regard, our preliminary findings indicated that the stably-transfected HT-1080 cells, similar to endothelial cells and smooth muscle cells (Iino et al., Arter. Thromb. Vase. Biol. 1998; 18:40-46; Herman et al., J. Clin. Invest. 2001; 107:1117-1126), secrete 4-6 fold higher levels of TFPI-2 into their ECM in cultures in comparison to their luminal secretion.

Figure 9:
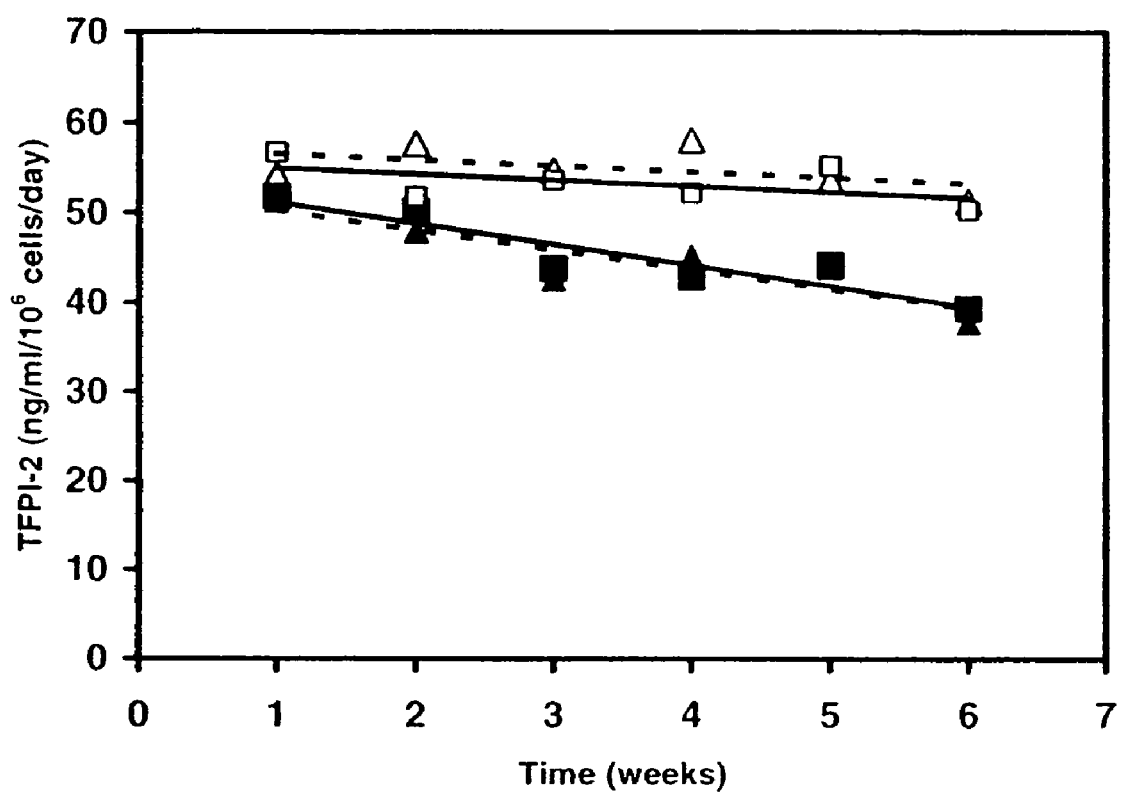
FIG. 9 shows expression of either wild-type or R24Q human TFPI-2 by stably-transfected HT-1080 cells in the presence and absence of G418. Stably-transfected HT-1080 cell lines, with an initial expression level of ~55 ng TFPI-2/ml/day/$10^6$ cells, was continuously cultured, with passaging, in the presence (□, △) and absence (■, ▲) of 0.6 mg/ml G418. The supernatants were assayed weekly for either TFPI-2 (□, ■) or R24Q TFPI-2 (△, ▲) expression by a sandwich ELISA as described in Example II.

Initial in-vitro studies revealed that the TFPI-2-expressing HT-1080 cells in continuous culture for six weeks secreted a relatively constant amount of TFPI-2 while under G-418 selection (FIG. 9). In the absence of G-418, these same cells continued to secrete TFPI-2, but the level declined by about 25% over six weeks of continuous culturing (FIG. 9). Despite the slow and progressive loss of the expression vector in the absence of G-418, i.e., under conditions that would partially mimic the in-vivo growth of this cell line, the TFPI-2 expression level was still about 80% over a five-week period. Accordingly, this period was selected as the time frame to evaluate the effect of TFPI-2 secretion on the in-vivo growth and metastasis of this tumor cell in SCID mice.

Figure 10:
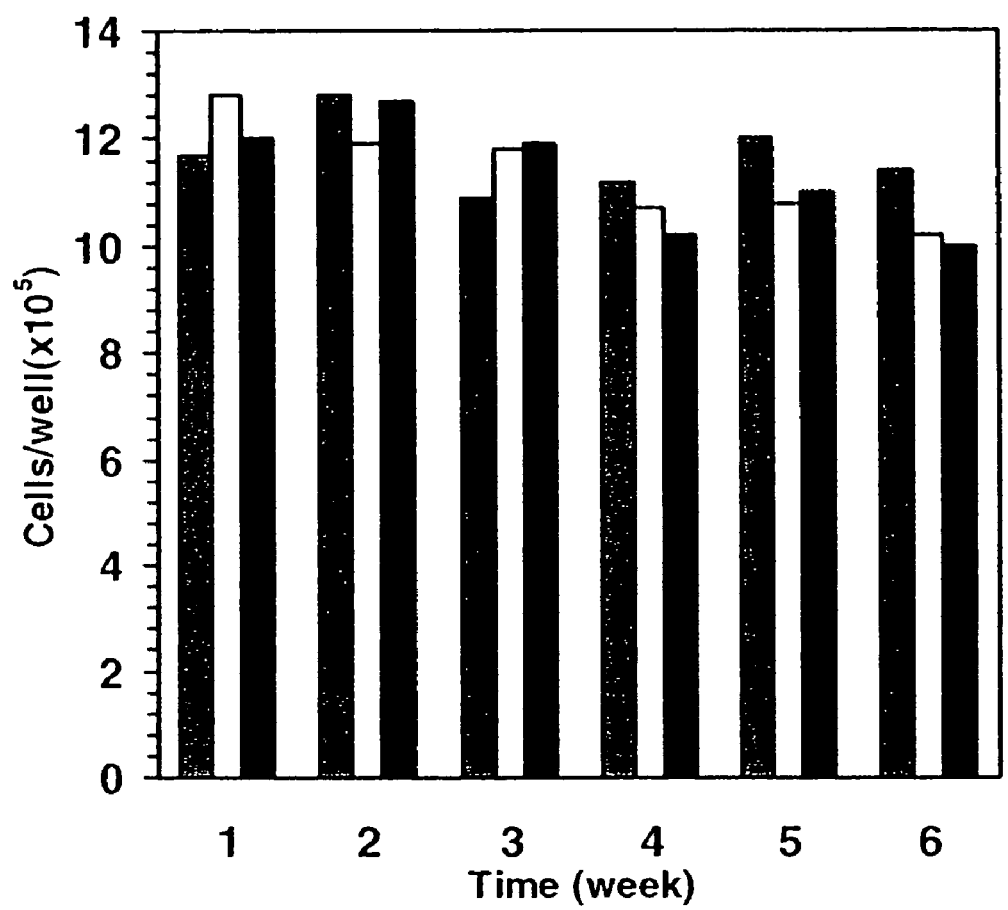
FIG. 10 shows growth rates of MT-1080, WT-1080 and QT-1080 cells in culture. MT-1080 cells (gray bars), WT-1080 cells (white bars), and QT-1080 cells (black bars) were initially plated at a density of $1\times10^5$ cells/well in a six well plate. Every seven days, the cells were trypsinized, counted and replated at the same seeding density.

We next evaluated whether the growth rate of TFPI-2-expressing HT-1080 cells in culture were similar to the mock-transfected HT-1080 cells (MT-1080) over a 6-week period as described elsewhere. Although a slight decline in proliferation rate was noted over time, the proliferative rates of all transfected HT-1080 cells were essentially equivalent, suggesting that TFPI-2 secretion by these cells had no influence on their growth rate in-vitro (FIG. 10).

In separate experiments, transfected HT-1080 cells cultured in the absence of G-418 also exhibited growth rates virtually identical to transfected cells grown in the presence of G-418, providing evidence that G418 was also not affecting the proliferative rate of these cells. Moreover, transfection of these cells had no effect on their proliferative rates, as transfected tumor cells, cultured in the absence of G418, grew at a rate indistinguishable from the parental HT-1080 cell line.

Growth of Transfected HT-1080 Tumors in Athymic Mice

Athymic male Balb/c mice, grouped randomly, were inoculated subcutaneously with $5\times10^6$ cells transfected HT-1080 cells. SQ tumor growth of MT-1080 cells was linear with time and achieved an average volume of 837±104 mm$^3$ five weeks post-inoculation (Table 2). SQ tumor growth of WT-1080 cells was also linear, but in sharp contrast to MT-1080 SQ tumors, these tumors were, on an average, 28-60% smaller than the MT-1080 tumors at comparable times post-inoculation (Table 2). QT-1080 SQ tumors exhibited essentially the same tumor growth rate as the MT-1080 tumors (Table 2), suggesting that secretion of wild-type TFPI-2 by WT-1080 cells was associated with reduced tumor size.

TABLE 2

Effect of TFPI-2 Expression on the Growth of HT-1080 Tumors

| Tumor Type | Tumor Volume (mm$^3$)$^§$ | | | | |
|---|---|---|---|---|---|
| | Week 1 | Week 2 | Week 3 | Week 4 | Week 5 |
| MT-1080 | 24.1 ± 4.7 | 165.9 ± 17.5 | 336.3 ± 38.2 | 570 ± 59.1 | 837 ± 103.8 |
| WT-1080 | 5.5 ± 0.8 | 66.9 ± 14.4 | 161.0 ± 30.6 | 327 ± 57.2 | 462 ± 70.5 |
| QT-1080 | 20.5 ± 4.0 | 155.6 ± 18.9 | 302.4 ± 36.2 | 515 ± 57.4 | 731 ± 78.1 |

$^§$Values are expressed as the Mean ± SEM. Differences between all mean values at a given time point were tested pairwise by one way analysis of variance (ANOVA) and statistical significance was accepted at P ≦ 0.05.

Mice were sacrificed five weeks post-inoculation. At sacrifice, the average weight of the resected MT-1080 and QT-1080 tumors was 2.65±0.56 g, whereas the average weight of the resected WT-1080 tumors was 1.47±0.34 g. Metastasis of MT-1080, WT-1080 and QT-1080 tumor cells in the SCID mice from the primary tumor location was confined exclusively to the lungs. Of the twelve SCID mice inoculated with MT-1080 cells, nine mice (75%) developed metastatic lesions/nodules in the lungs, as compared to a metastatic incidence of 42% (5/12) in mice inoculated with WT-1080 cells (P<0.001). The metastatic incidence of SCID mice inoculated with QT-1080 cells was identical to that observed for mice inoculated with MT-1080 cells. In order to assess the degree of metastasis in each experimental group, four randomly selected paraffin-embedded lungs from each group were sectioned in their entirety, and all sections (except every fourth section) were H&E stained. Examination of these sections revealed as many as 5-8 metastatic sites per tumor-positive lung in mice injected with MT-1080 cells, while only 1-2 metastatic sites were observed in tumor-positive lungs of mice inoculated with WT-1080 or QT-1080. The metastatic tumor size, evaluated from the number of sections they spanned, varied from 30-300μ. As with the growth of SQ tumors in athymic mice, these findings provide evidence that metastasis of HT-1080 tumors was markedly inhibited through their ability to secrete inhibitory TFPI-2.

Histological and Immunohistochemical Analyses of Primary and Metastatic Tumors

Figure 11:
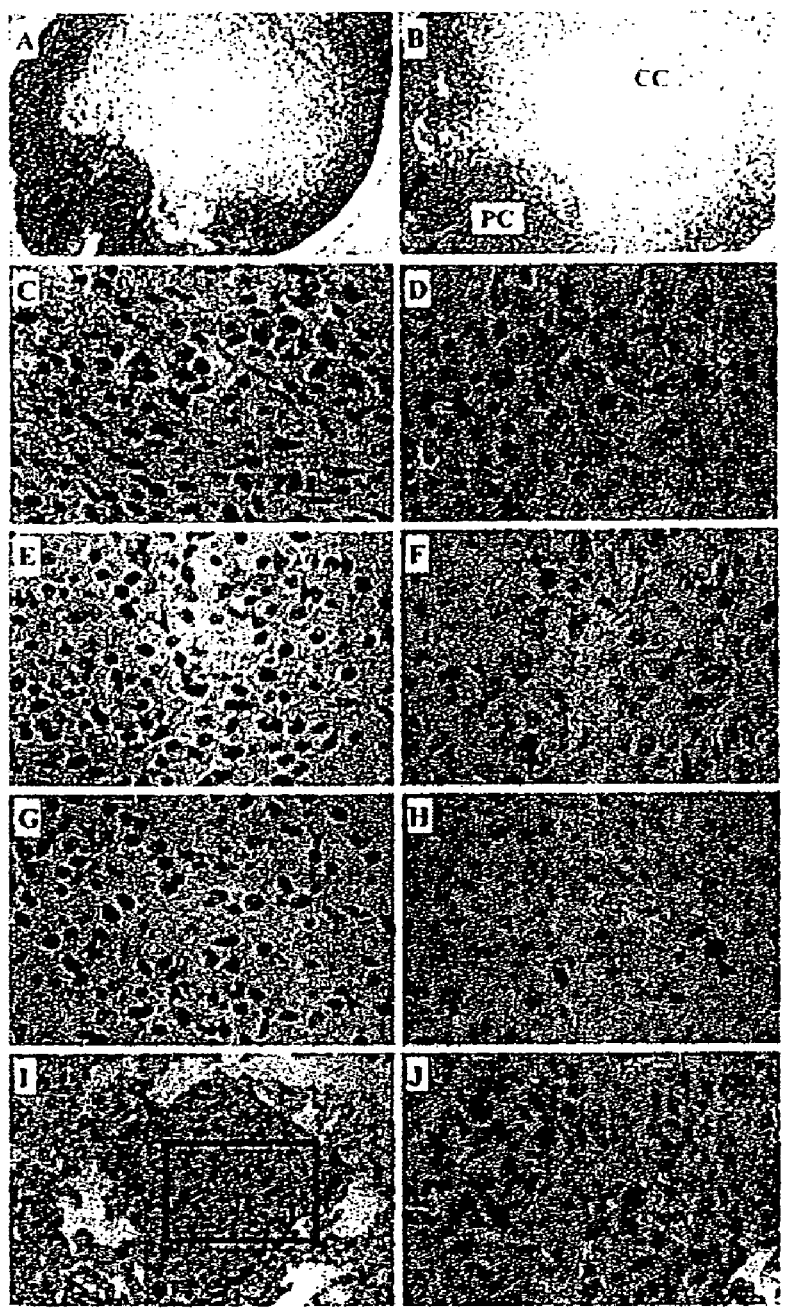
FIG. 11 shows histological and immunohistochemical analyses of paraffin-embedded subcutaneous (A-H) and lung (I,J) tumors. Tumor sections (5µ) were either stained with hematoxylin and eosin (H&E) or treated with antibody as described in Materials and Methods. (Panel A), H & E stained subcutaneous tumor; (Panels B-D), immunohistochemical detection of TFPI-2 (arrows) in subcutaneous tumors; (Panels E,F), immunohistochemical detection of BrdU-positive cells (arrowheads) in subcutaneous tumors; (Panels G,H), TUNEL staining for apoptotic cells (arrowheads) in subcutaneous tumors; (Panels I,J), anti-TFPI-2 IgG immunohistochemistry of metastatic lung tumors. Boxed area in I is magnified an additional 2.5-fold in panel J. PC, peripheral cells (Panels D, F & H). CC, core cells (Panels C, E & G). Magnifications: A and B, 250×; I, 1000×; C-H, J, 2500×.

The histology of all primary SQ tumors, shown in FIG. 11 (Panel A), exhibited a peculiar morphology with loosely distributed cells in a core region (referred to as core cells, or CC) encompassed by rather tightly packed peripheral cells (PC). Initial immunohistochemical analyses of MT-1080, WT-1080 and QT-1080 cell cytospins revealed that MT-1080 cells were negative for TFPI-2 antigen, consistent with the absence of detectable TFPI-2 in parental HT-1080 cell conditioned media by ELISA. On the other hand, WT-1080 and QT-1080 cells, stained strongly positive for TFPI-2 antigen in cell cytospins. In agreement with the cell cytospin analyses, primary MT-1080 tumors exhibited negative immunoreactivity for TFPI-2 antigen both in the PC and CC regions. In contrast, WT-1080 and QT-1080 primary tumors stained positive for TFPI-2 antigen in the PC region (FIG. 11, Panel D), but failed to stain in the CC region (FIG. 11, Panel C). Interestingly, metastatic tumors from all groups of mice, when subjected to immunohistochemical analyses, failed to show any detectable TFPI-2 antigen (FIG. 11, Panels I & J).

Differential Cellular Proliferation and Apoptosis

The relative distribution of proliferating (BrdU positive) cells was also assessed in sections of primary tumors from each experimental group. More than 90% of the PC in all three tumor-types was proliferating (FIG. 11, Panel F), whereas only 8-10% of CC were proliferating in MT-1080 or QT-1080 primary tumors. By comparison, more than 20% of CC region cells in WT-1080 tumors were positive for proliferation (FIG. 11, Panel E). When examined for apoptosis by TUNEL assay, very few cells in the PC or CC regions in MT-1080 and QT-1080 primary tumors stained positive. In the case of the WT-1080 primary tumors, negligible numbers of cells were undergoing apoptosis in the PC region, whereas >40% of cells in the CC region stained positive (FIG. 11, Panel G & H).

Tumor Cell DNA Analyses

Figure 12:
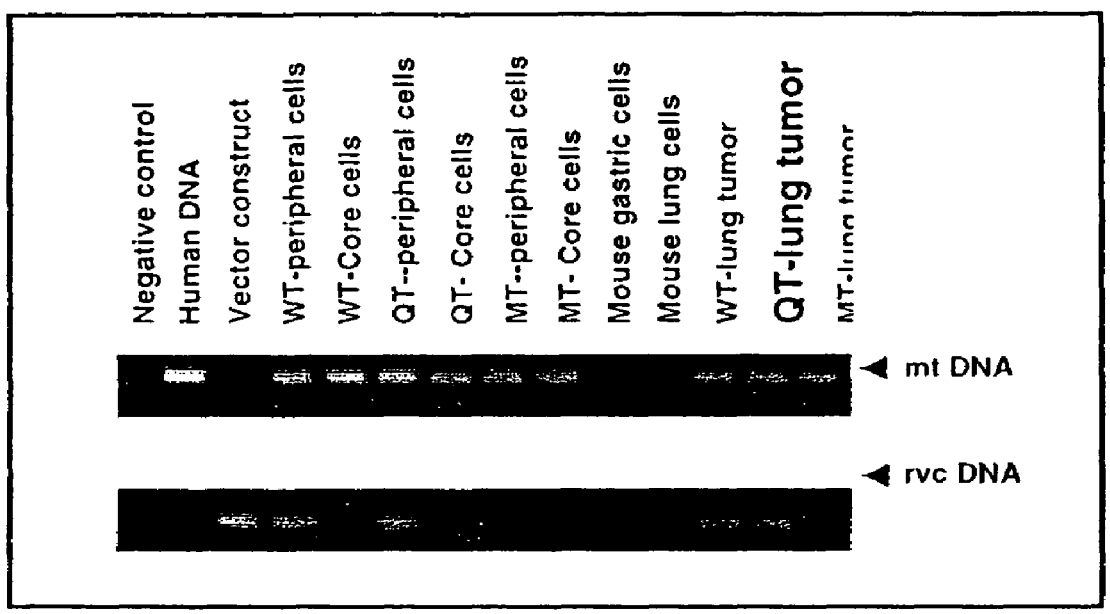
FIG. 12 shows qualitative PCR analyses of cellular DNA obtained from various tissues by microdissection. Cellular DNA used as a template in these PCR reactions was obtained from microdissected cells as described in Materials and Methods, and PCR products resolved electrophoretically in 1.2% agarose gels. Cellular DNA from mouse gastric and lung cells were processed in an identical manner to exclude the possibility that the human-specific primer pair cross-reacted with mouse DNA.

To address the possibility that the core cells were of murine origin recruited into the growing tumor mass, a PCR-based qualitative analysis was performed on each cell type (PC and CC) found in the three primary tumors, as well as cells of metastatic tumors. Cellular DNA was prepared from microdissected cells as described earlier. By qualitative PCR amplification using human mitochondrial (mtDNA)-specific primers, both PC and CC cell types were positive for human mitochondrial DNA (FIG. 12, top panel), providing evidence that these regions contain human cells. PCR amplification of the recombinant vector/construct (rvcDNA)-specific region revealed that only cellular DNA from the PC regions of WT-1080 and QT-1080 tumors was positive (FIG. 12, bottom panel). No rvcDNA amplification was observed in MT-1080 tumor cells (FIG. 12, bottom panel). The metastatic lung tumors also demonstrated the presence of human mitochondrial DNA attesting to their human origin (FIG. 12, top panel). Somewhat surprisingly, cellular DNA derived from WT-1080 and QT-1080 lung tumors tested positive for the intact rvcDNA region following PCR amplification (FIG. 12, bottom panel), in spite of undetectable TFPI-2 antigen in these cells. The reason for this discrepancy is not known, but most probably relates to the relative sensitivities between immunohistochemistry and PCR amplification techniques. Alternatively, TFPI-2 synthesis and expression may be downregulated by lung-specific signaling molecules from the metastatic tumor microenvironment.

VEGF Expression in Tumors

Figure 13:
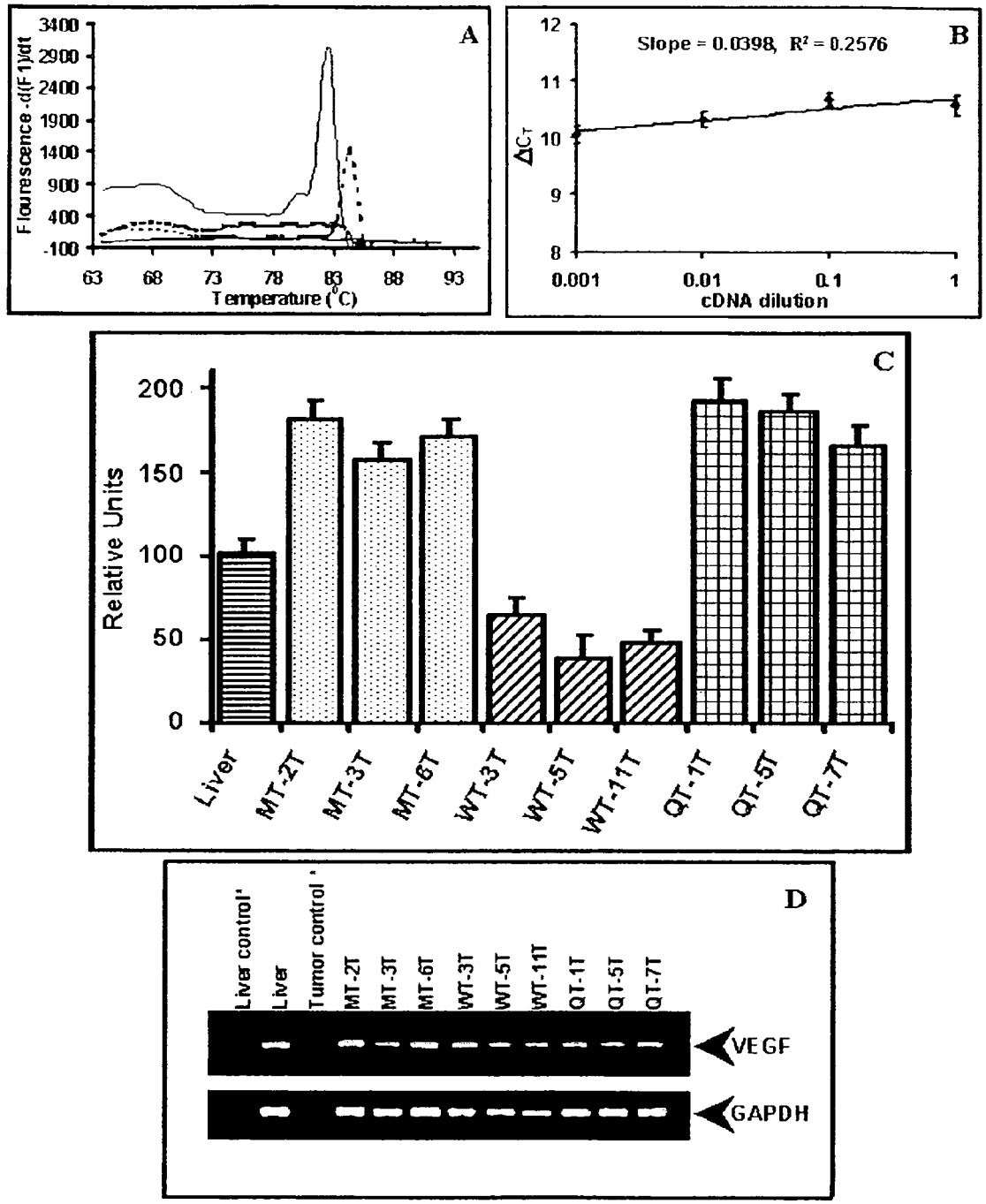
FIG. 13 shows real time quantitative RT-PCR analysis of murine VEGF gene expression in tumors. A: melting curve analysis of the VEGF and GAPDH amplicons. Distinct melting curves of VEGF (dashed line) and GAPDH (solid line) are shown together with controls. B: relative efficiency plot of VEGF and GAPDH. The $\Delta C_T$ (difference in $C_T$ values of VEGF and GAPDH) were calculated for each cDNA dilution. C: murine VEGF gene expression levels in MT-1080, QT-1080 and WT-1080 tumor samples. Mouse liver RNA (line-filled bar) was used as a positive control. Each column represents the average of three amplification reactions (error bars represent standard deviation) performed on a single cDNA sample reverse-transcribed from RNA derived from each tumor sample. Samples MT-2T, MT-3T and MT-6T are representative MT-1080 tumors (dot-filled bars). Samples WT-3T, WT-5T and WT-11T are representative WT-1080 tumors (reverse-hatched bars), while samples QT-1T, QT-5T, and QT-7T are representative QT-1080 tumors (small square bars). D: agarose gel analyses of PCR products obtained following specific amplification of murine VEGF (upper panel) and murine GAPDH (lower panel) amplicons. Asterisks indicate negative controls lacking reverse transcriptase in first strand cDNA synthesis.

As VEGF expression is critical for tumor microvasculature formation (Shih et al., Am. J. Pathol. 2002; 161:35-41), we performed a real time quantitative RT-PCR analysis to assess murine VEGF gene expression levels in three tumor samples randomly selected from each tumor group. Melting curve analyses of the amplified PCR products revealed predominately a single product with distinct $T_m$ values ($T_m$=82.6° C. for GAPDH and $T_m$=84.4° C. for VEGF; FIG. 13A). The efficiencies for the VEGF and GAPDH amplification were similar as the slope obtained from a plot of log cDNA dilution versus $\Delta C_T$ was <0.1 (FIG. 13B), thus validating the primer sets. The relative VEGF levels (mean ±SEM) for mouse liver and three representative samples of each tumor type were then plotted as shown in FIG. 13C. Tumors arising from MT-1080 cells showed a 3-6-fold higher expression of VEGF mRNA than tumors derived from WT-1080 cells, whereas VEGF mRNA expression in QT-1080 cells was essentially identical to VEGF mRNA levels found in MT-1080 cells. The final PCR reaction products revealed amplification of a single, specific band for VEGF (FIG. 13D, upper panel) and GAPDH (FIG. 13D, lower panel) on agarose gel electrophoresis.

Genes Regulated by TFPI-2 Expression

Using four-independent tumor samples in the Affymetrix GeneChip® microarray system, a relative gene expression profile was obtained. Comparative differential gene-expression analysis revealed that 80 genes had significantly altered levels of expression, directly or indirectly regulated by TFPI-2 expression in these tumors. Among these, 43 genes were upregulated and 37 genes were downregulated. Further analysis revealed that 15 mRNA species were induced by more than 4-fold and 10 mRNA species were repressed by 4-fold or more. In Table 3, the proteins encoded by these genes are grouped according to their functions. The analysis of the genes according to a gene ontology system showed that TFPI-2 expression regulated genes in almost every category including those implicated in transcription, signal transduction, cell growth and proliferation, extracellular matrix, oncogenesis, invasion and metastasis, apoptosis and angiogenesis.

TABLE 3

Genes regulated by TFPI-2 expression in fibrosarcoma xenografts obtained from SCID mice.

| GeneBank Accession no. | Fold Change* | Description |
| --- | --- | --- |
| | | Transcription factors |
| NM_001186 | −2.11 | Helicase, Basic leucine zipper transcription factor-1 |
| NM_006963, AA744771 | +29.27 | Zinc finger protein 22 (KOX 15) |
| NM_006291 | +5.05 | Zinc finger protein 185 (LIM domain) |
| NM_014368 | +2.91 | LIM homeobox protein 6 |
| NM_001290 | −5.20 | LIM domain binding 2 |
| NM_002586 | −2.75 | PBX-2, Pre-B cell leukemia transcription factor-2 |
| X16155 | −2.79 | COUP-transcription factor |
| | | Signal transduction |
| NM_004445 | −2.38 | Erythropoietin-producing hepatocyte kinase, EphB6 |
| NM_002547 | +2.95 | Oligophrenin 1 |
| NM_002821 | +2.33 | protein tyrosine kinase 7 |
| U71075 | −2.48 | Protein tyrosine phosphatase, receptor type, U |
| D30751 | +2.79 | Bone morphogenetic protein 4 |
| NM_022159 | −2.92 | EGF-TM7-latrophilin-related protein |
| | | Cell growth, proliferation and maintenance |
| NM_013975 | +2.04 | Ligase III, DNA |
| NM_006567 | +2.11 | Phenylalanine-tRNA synthetase |
| AU118882, NM_001957 | −2.90 | Endothelin receptor type A |
| NM_002349 | +14.32 | Lymphocyte antigen 75, gp200-MR6 |
| NM_005330 | −7.63 | Hemoglobin, epsilon 1, oxygen transport |
| NM_000385 | +2.30 | Aquaporin 1 |
| AF052169 | +2.48 | voltage-gated potassium channel activity |

TABLE 3-continued

Genes regulated by TFPI-2 expression in fibrosarcoma xenografts obtained from SCID mice.

| GeneBank Accession no. | Fold Change* | Description |
|---|---|---|
| BE742268 | −4.21 | sortilin 1 (SORT1) |
| AW206786 | −2.32 | enigma (LIM domain protein) |
| | | Invasion and Metastasis |
| M34064 | −2.13 | N-Cadherin |
| NM_014751 | +2.06 | Metastasis suppressor gene |
| NM_002961 | +2.79 | S100 calcium-binding protein A4 |
| NM_021111 | +2.64 | Reversion-inducing-cysteine-rich protein with kazal motif (RECK) |
| AF348491, AJ224869 | −4.21, −27.40 | Chemokine (C-X-C motif), receptor 4 (fusin) |
| NM_022842 | −18.70 | CUB domain-containing protein 1 (CDCP1) |
| | | Oncogenes/Tumor suppressor genes |
| NM_021991 | −2.21 | Junction plakoglobin |
| NM_003287 | +2.10 | Tumor protein D52-like 1 |
| NM_001958 | +6.85 | EEF1A2, Eukaryotic translation elongation factor 1 alpha 2 |
| | | Apoptosis |
| NM_005892 | −2.14 | Formin like (FRL) |
| NM_020371 | −2.11 | Cell death regulator Aven |
| | | Angiogenesis |
| NM_002019 | −2.24 | FLT, VEGFR1, Fms-related tyrosine kinase receptor |
| NM_000584 | −6.99 | Interleukin-8 (IL-8, C-X-CL8) |
| AI812030 | −3.39 | thrombospondin 1 precursor |
| LO1639 | −8.03 | Neuropeptide Y receptor |
| U58111 | −2.41 | Vascular endothelial growth factor C |
| NM_006291 | +2.98 | Tumor necrosis factor, alpha-induced protein 2 |
| | | Extracellular matrix |
| NM_002607 | +2.53 | platelet derived growth factor alpha polypeptide |
| NM_021599 | −4.62 | ADAM-TS2 |
| BC002416 | −2.29 | Biglycan |
| NM_000088 | +3.51 | Collagen, type I, alpha 1 |
| AI264196 | −2.48 | fibrillin 1 precursor |
| D32039 | −2.13 | Chondroitin sulfate proteoglycan 2 (versican) |
| AI146848 | +2.87 | dermatopontin precursor |
| AJ276395 | −3.80 | Fibronectin 1 |
| AA669336 | +7.26 | Alpha 1 chain of Type XII Collagen |
| | | Others |
| NM_002759 | +2.51 | EIF2Ak1, protein kinase, PKR |
| NM_004988 | −2.95 | MAGE-A1, Melanoma antigen family A1 |
| NM_016931 | −2.46 | Nox 4, NADPH oxidase 4 |
| NM_021822 | +2.80 | Phorbolin-like protein MDS019 |
| NM_001785 | +35.30 | Cytidine deaminase |

*The number indicates the -fold change in mRNA abundance in TFPI-2 expressing tumors over mock-transfected tumors determined by microarray data analysis. + and − indicate increased and decreased mRNA levels.

Discussion

In the present study, we have prepared stably-transfected human HT-1080 fibrosarcoma cell lines expressing either wild-type human TFPI-2 or an inactive mutant TFPI-2 (R24Q TFPI-2), and assessed their ability to grow and metastasize in athymic Balb/c mice in relation to a mock-transfected HT-1080 cell line. We observed that stably-transfected WT-1080 cell tumor grew at a substantially lower (about 28-60%) rate than MT-1080 solid tumors. QT-1080 produced subcutaneous tumor masses essentially identical in volume to that observed for the MT-1080, providing suggestive evidence that the expression of inhibitory TFPI-2 was associated with restricted tumor growth. In addition to the substantially decreased growth rate of WT-1080 tumors, the metastatic rate of WT-1080 cells (42%) was also markedly lower than that observed for QT-1080 or MT-1080 cells (75%). The decreased metastatic rate of WT-1080 cells in all likelihood relates to a smaller primary tumor mass burden rather than TFPI-2 expression, as immunohistochemical analyses revealed that the WT-1080 metastatic tumors paradoxically failed to stain for immunoreactive TFPI-2 but retained the vector/construct as shown by PCR. The reason(s) for this discrepancy is not known but may be related to different sensitivities between these two techniques and/or downregulation of TFPI-2 expression in the metastatic tumor microenvironment.

Our in vivo findings are clearly consistent with and extend previous in-vitro results demonstrating a dose-dependent inhibition of HT-1080 invasiveness in Matrigel and ECM degradation by exogenous TFPI-2 (Rao et al., Int. J. Cancer 1998; 75:749-756). Our results are also consistent with a recent report by Konduri and colleagues (Konduri et al., Oncogene 2001; 20:6938-6945) demonstrating that high-grade SNB19 glioma cells stably-transfected with the human TFPI-2 expression vector formed smaller intracerebral tumors in contrast to its mock-transfected counterpart. Finally, our data agree, in part, with that very recently published by Jin and coworkers (Jin et al., Gync. Oncol. 2001; 83:325-333) who demonstrated that TFPI-2-expressing human choriocarcinoma cells (JAR) exhibited decreased invasive properties in Matrigel relative to mock-transfected JAR tumor cells, as well as decreased invasiveness in-vivo in nude mice following SQ transplantation. However, in contrast to our findings using HT-1080 fibrosarcoma cells, mock-transfected and TFPI-2-expressing human choriocarcinoma tumors were essentially identical in mass and failed to metastasize (Jin et al., Gync. Oncol. 2001; 83:325-333).

Histological analyses on primary and metastatic tumors were performed to evaluate the effects of TFPI-2 on tumor growth and metastasis. HT-1080 tumors consisted of two distinct regions; a homogeneous core of cells with condensed nuclei, and peripheral cells that appeared morphologically similar to cultured HT-1080 cells. Although both regions demonstrated the presence of human mtDNA, only cells occupying the peripheral regions were positive for TFPI-2 antigen and demonstrated presence of the vector construct. BrdU and TUNEL staining confirmed that cells present in the peripheral region were still proliferating, while most of the cells occupying the core region were undergoing apoptosis. Since tumor volumes were significantly smaller in WT-1080-treated mice, TFPI-2 most likely affects those processes involved in tumor mass formation in-vivo, such as neovascularization, rather than inhibiting the proliferative rate of individual tumor cells.

The precise mechanism(s) whereby genetically engineered expression of functional TFPI-2 by a TFPI-2 null cell reduces tumor size and its aggressive phenotype in-vivo is unclear. During tumor growth, malignant cells invade normal adjacent tissues, and regulation of plasmin activity on the surface of tumor cells has been shown to influence the invasive and metastatic behavior of tumor cells (Crowley et al., Proc. Natl. Acad. Sci. USA 1993; 90:5021-5025; Stahl et al., Cancer Res. 1994; 54:3066-3071; Min et al., Cancer Res. 1996; 56:2428-2433). However, plasmin associated with the ECM or the membranes of cultured cells is resistant to inhibition by known physiologically-relevant proteinase inhibitors (Bizik et al., Cell Regul. 1990; 1:895-905; Quax et al., J. Cell Biol. 1991; 115:191-199; Reinartz et al., Exp. Cell Res. 1993; 208:197-208), and it has been suggested that metastatic tumor cells generate "unregulated" plasmin activity which potentiates metastatic behavior (Kwaan et al., Cancer Metastasis Rev. 1992; 11:291-311; Kramer et al., Cancer Metastasis Rev. 1994; 14:210-222). Many tumor cells, including the HT-1080 fibrosarcoma cell line utilized in this study, employ the uPA-uPAR system to activate plasminogen, resulting in plasmin-mediated ECM degradation and invasion, as well as proMMP-1 and proMMP-3 activation that further enhances tumor invasion and metastasis (Rao et al., Biochem. Biophys. Res. Commun: 1999; 255:94-99). In addition, tumor growth is highly dependent on an adequate blood supply, and plasmin presumably plays an important role in tumor angiogenesis (Tarui et al., J. Biol. Chem., 2002, 277:33564-33570). In this regard, Soff and coworkers (Soff et al., J. Clin. Invest. 1995; 96:2593-2600) have reported that expression of PAI-1 by a stably-transfected human prostate carcinoma cell line (PC-3) markedly reduced the growth rate of these primary tumors in an athymic mouse model in relation to the parental PC-3 cell line, providing clear evidence that regulation of plasmin formation reduced the aggressive phenotype of these cells. In view of its ability to strongly inhibit plasmin in vitro, it is not unreasonable to speculate that ECM-associated TFPI-2 generated by WT-1080 tumors inhibits ECM turnover mediated by plasmin and plasmin-activated matrix metalloproteinases, thereby inhibiting tumor invasiveness and metastases in-vivo. In this connection, preliminary studies have shown that wild-type human TFPI-2 exhibited a potent and dose-dependent anti-angiogenic effect in both the VEGF-induced chorioallantoic membrane assay and the FGF-2-induced cornea pocket assay. Accordingly, the ability of secreted TFPI-2 to reduce tumor size may be dependent, in part, on its anti-angiogenic properties.

To establish the role of TFPI-2, if any, in neovascularization essential for tumor growth and metastasis, host VEGF gene expression was quantitated in these tumors by real time quantitative RT-PCR. MT- and QT-1080 tumors expressed essentially the same levels of VEGF mRNA, whereas WT-1080 tumor VEGF mRNA levels were reduced 3-6-fold in relation to MT- and QT-1080 tumors. Accordingly, a clear quantitative correlation was observed between murine VEGF expression levels and tumor size, suggesting that active TFPI-2 plays a suppressive role on host-derived VEGF gene expression and, by extension, on VEGF-mediated angiogenesis. The cellular origin of murine VEGF mRNA isolated from these tumors is not known, although host stromal cells may be one cell responsible for VEGF synthesis. Clearly, the higher apoptotic rate of WT-1080 tumor core cells strongly suggests decreased tumor angiogenesis in this portion of the tumor architecture that may be related to either lower host VEGF mRNA expression in these tumors, or elevated levels of angiostatin, or both. Although wild-type HT-1080 cells constitutively secrete human VEGF (Sawaji et al., Br. J. Cancer 2002; 86:1597-1603) that presumably contributes greatly to neovascularization in these tumors, recent studies have shown that complete inhibition of rhabdomyosarcoma xenograft growth and neovascularization in nude mice required inhibition of both tumor and host-derived VEGF (Gerber et al., Cancer Res. 2000; 60:6253-6258).

The relative assessment of genes in the snap-frozen tumor xenograft by oligonucleotide-based microarray analysis revealed no significant change in the human (tumor) VEGF gene levels, although a 2-fold or greater decrease in FLT-1 (VEGFR1) and VEGF-C mRNA levels was observed. VEGF-C and VEGFR1, a VEGF receptor, have been implicated in tumor-related angiogenesis (Andre et al., Int. J. Cancer 2000; 86:174-181; Olofsson et al., Proc. Natl. Acad. Sci. USA 1998; 95:11709-11714; Mandriota et al., EMBO J. 2001; 20:672-682). Thus, induced TFPI-2 expression does not regulate tumor VEGF mRNA levels but rather appears to suppress its angiogenic effect by downregulating receptor (VEGFR1) levels. Among other angiogenic regulators, IL-8, THBS-1 and neuropeptide-Y receptor gene levels were also down-regulated, whereas the tumor necrosis factor alpha-induced protein 2 (TNF-AIP2) levels were upregulated. Interleukin-8 is not expressed constitutively, but on TNF-α induction inhibits apoptosis via NF-kappaB and Akt signaling pathways (Osawa et al., Infect. Immun. 2002; 70:6294-6301). IL-8 also exhibits potent angiogenic activity and thus may play a role in tumor progression. Thrombospondin (THBS-1) suppresses tumor growth, inhibits activation of MMP-9 and inhibits VEGF binding to receptor suppressing capillary morphogenesis (Rodriquez-Mazaneque et al., Proc. Natl. Acad. Sci. USA 2001; 98:12485-12490). Surprisingly, its expression is downregulated by TFPI-2, partially reducing its anti-tumor growth function. However, another anti-angiogenic gene, neuropeptide Y receptor-2 regulates angiogenesis-dependent tumor repair (Ekstrand et al., Proc. Natl. Acad. Sci. USA 2003; 100:6033-6038), and is down-regulated. Thus, at the transcriptional level, TFPI-2 expression regulates both pro- and anti-angiogenic regulators, which, in concert, could affect tumor angiogenesis.

The pro-invasive and pro-metastatic genes such as N-cadherin, CDCP1 and chemokine receptor 4 are suppressed by TFPI-2 induction in these tumor cells. N-cadherin, a cell adhesion molecule, makes heterotypic contacts with catenin (α, β, γ)-p120$^{ctn}$ promoting matrix invasion and transendothelial migration by convergence of TGF-β signaling (Mareel et al., Physiol. Rev. 2003; 83:337-76). The junction plakoglobin (γ-catenin) (Winn et al., Oncogene 2002; 21:7497-7506) is also suppressed by TFPI-2. Protein tyrosine phosphatase receptor µ (PTPRmu) (Zondag et al., J. Biol. Chem. 2000; 275:11264-11269), another component of this cadherin-catenin complex that dephosphorylates p120$^{ctn}$, is also down-regulated. Thus, most of the components of the cadherin-catenin complex are suppressed, possibly leading to an imbalance between levels of activated N-cadherin and E-cadherin necessary for cell motility and tumor invasion (Mareel et al., Physiol. Rev. 2003; 83:337-76). Furthermore, the ectodomain of E-cadherin (sE-CAD) is shed by plasmin, stromelysin-1 and matrilysin (MMP7) cleavage thereby stimulating tumor invasion, in part, by upregulation of MMP-2, MMP-9 and MT1-MMP (Mareel et al., Physiol. Rev. 2003; 83:337-76; Ryniers et al., Biol. Chem. 2002; 383:159-165; Nawrocki-Raby et al., Int. J. Cancer 2003; 105:790-795). Since it is thought that metastatic tumor cells generate "unregulated" plasmin activity (Kwaan et al., Cancer Metastasis Rev. 1992; 11:291-311; Kramer et al., Cancer Metastasis Rev. 1994; 14:210-222), the tumor growth suppression could also be affected by the plasmin-inhibitory activity of TFPI-2 suppressing sE-CAD production.

Tumor invasion metastasis suppressor genes, MIM (Lee et al., Neoplasia 2002; 4:291-294) and RECK are induced more than 2-fold in TFPI-2 over-expressing tumors. Overexpression of RECK has been shown to form HT-1080 tumors defective in vasculature due to inhibition of angiogenic sprouting through excessive degradation of the ECM (Oh et al., Cell 2001; 107:789-800). Moreover, RECK negatively regulates matrix-metalloproteinases MMP-2, MMP-9 and MT1-MMP, thereby inhibiting tumor invasion, metastasis and angiogenesis (Noda et al., Cancer Metastasis Rev. 2003; 22:167-175; Takahashi et al., Proc. Natl. Acad. Sci. USA 1998; 95:13221-13226). However, the prometastatic gene, S100A4/MTS1/metastasin, upregulated in medulloblastoma, brain cancer cells, and murine melanoma (Mazzucchelli, Am. J. Pathol. 2002; 1601:7-13), was also upregulated in these tumors.

Two of the pro-apoptotic genes, FRL (Yayoshi-Yamamoto et al., Mol. Cell. Biol. 2000; 20:6872-6881), and chemokine receptor 4 (CXC-R4) (Bodner et al., J. Neuroimmunol. 2003; 140:1-12) are downregulated, suggesting the induction of genes that support tumor cell growth and survival. In contrast, the anti-apoptotic gene, Aven (Chau et al., Mol. Cell. 2000; 6:31-40), is downregulated. Genes encoding for extracellular matrix constituents like ADAM-TS2, biglycan, fibronectin 1, versican, and fibrillin 1 precursors are suppressed, whereas dermatopontin and collagen I alpha 1 genes are upregulated, suggesting regulation of ECM remodeling at the transcriptional level. In addition, a large number of genes found to be regulated by TFPI-2 in this model are implicated in general cellular functions including signal transduction, cell growth and proliferation and the synthesis of some transcription factors, which in turn regulate other genes that affect other cellular processes.

While the genomic response to TFPI-2 overexpression appears complex, most of the genes regulated by TFPI-2 would result in an overall decrease in tumor growth and metastatic potential. The molecular mechanism whereby TFPI-2 expression and function affects tumor cell gene expression is not known, but presumably involves its ability to regulate proteinases such as trypsin, plasmin or the factor VIIa-tissue factor complex either on the tumor cell or in the tumor microenvironment that, in turn, affect a variety of tumor cell signaling processes involved in growth and angiogenesis. Future studies focused on the regulation and functional significance of the target genes reported here are likely to increase our understanding of the role of TFPI-2 in the regulation of pericellular ECM remodeling in normal and tumor cells.

Example IV

Plasmin Inhibitor TFPI-2/KD1 Blocks Mononuclear Cell Migration into Airways in a Murine Model of Allergic Asthma Recent published work, using plasminogen knockout mice, has demonstrated that plasminogen and its activated form, the serine proteinase plasmin, regulate cellular recruitment and pathogenesis in a murine model of asthma. In addition to playing a major role in fibrinolysis and matrix metalloproteinase activation, plasmin cleaves cell surface G-coupled proteins (protease activated receptors) leading to signal transduction events, increased mRNA expression and increased cellular migration.

We have recently demonstrated that constitutive expression of tissue factor pathway inhibitor-2 (TFPI-2), a Kunitz-type plasmin inhibitor, by a fibrosarcoma tumor cell markedly decreased its subcutaneous growth and metastasis in athymic mice in a process that partly involves decreased tumor angiogenesis (Example III). We were interested in testing whether a recombinant preparation of the first Kunitz-type domain of TFPI-2 (KD1) that inhibits plasmin activity in vitro ($K_i$=3 nM) affects the putative plasmin-mediated development of allergic lung inflammation and the recruitment of leukocytes to the airways.

$B_6D_2F1$ mice were immunized with ovalbumin (OVA) adsorbed to alum (days 0 and 5) and received two OVA aerosols on day 12. A subgroup of mice were treated with hexahistidine-tagged KD1, delivered via the lateral tail vein, on days 11-14. Mice were sacrificed on day 15 for the enumeration and differentiation of cells in the airway and lung tissue compartments.

Treatment with hexahistidine-tagged KD1 resulted in a statistically significant decrease in total numbers of cells, macrophages and lymphocytes recoverable from the airways after OVA aerosol in comparison to vehicle treated mice. Total numbers of cells recovered by collagenase digestion of lung tissue was equivalent in mice treated with hexahistidine-tagged KD1 as compared to vehicle. These data suggest that plasmin mediates transepithelial, but not transendothelial, migration of mononuclear cells in a murine model of asthma. See Wilder et al., Am. J. Resp. Crit. Care Med. 2004; 169(7): A803.

Example V

Crystal Structure of Kunitz Domain 1 (KD1) of Tissue Factor Pathway Inhibitor-2 with Trypsin and Molecular Model of KD1 with Plasmin and Factor VIIa/Tissue Factor: Implications for KD1 Specificity of Inhibition Tissue factor pathway inhibitor-2 (TFPI-2), also known as matrix serine protease inhibitor or placental protein 5, contains three Kunitz-type inhibitory domains in tandem. A variety of cells including keratinocytes, dermal fibroblasts, smooth muscle cells, syncytiotrophoblasts, synoviocytes, and endothelial cells synthesize and secrete TFPI-2 into the extracellular matrix (ECM). Kunitz domain 1 (KD1) of TFPI-2 inhibits plasmin ($K_i$=3 nM), trypsin ($K_i$=13 nM), and FVIIa/TF ($K_i$=1640 nM).

We employed crystallography and molecular modeling approaches to elucidate the basis of the specificity of KD1 for plasmin versus trypsin or FVIIa/TF. Crystals of the complex of KD1 with bovine trypsin were obtained that diffracted to 1.8 Å and belonged to the space group $P2_12_12_1$ with unit cell parameters, a=74.11, b=77.01, and c=125.42. Each asymmetric unit contained two KD1-trypsin complexes. The structure of KD1 thus obtained was then used in conjunction with the known structures of plasmin and FVIIa/TF to model the KD1-plasmin and KD1-FVIIa complexes. KD1 contained a hydrophobic core consisting of residues Leu-9 (BPTI numbering), Tyr-11, Tyr-22, and Phe-33.

In all structures, Arg-15 (P1 residue) of KD1 interacted with Asp-189 (chymotrypsin numbering) at the bottom of the specificity pocket. A hydrophobic patch involving residues Leu-17, Leu-18, Leu-19, and Leu-34 of KD1 was identified to interact with a hydrophobic patch in plasmin and trypsin but not in FVIIa/TF. This complementary hydrophobic patch in plasmin consists of Phe-37, Met-39, Phe-41, and the carbon side chains of Gln-192 and Glu-141. In trypsin, it consists of Tyr-39, Phe-41, Tyr-151 and the carbon side chain of Gln-192. Furthermore, a basic patch involving Arg-98, Arg-173 and Arg-221 in plasmin was identified to interact with an acidic patch in KD1 consisting of residues Asp-10 and Glu-39. This electrostatic interaction is absent in trypsin and in FVIIa/TF. Moreover, Tyr-46 in KD1 can make H-bonds with Lys-61 and Arg-64 in plasmin as well as with Lys-60A in FVIIa/TF; however, these interactions are absent in trypsin. Further, Arg-20 of KD1 is important for making a H-bond with Glu-60 in plasmin, with Lys-60 through a water molecule in trypsin and with Asp-60 in FVIIa/TF.

Cumulatively, the crystal structure and refined modeling data confirm our previous predictions and illustrate the molecular basis for preference of KD1 to inhibit plasmin versus trypsin or FVIIa/TF. KD1 interacts with plasmin through hydrophobic and electrostatic interactions whereas the electrostatic contacts are limited in trypsin. Notably, both the electrostatic and hydrophobic interactions are sparse in FVIIa/TF. Thus, both the crystal and modeled structures validate the differential effects of mutations in KD1 involving residues surrounding the P1 site, including D10A, L17Q, R20D, and F33A, reported earlier (Chand et al., J. Biol. Chem. 279, 17500-17507, 2004). Knowledge gained from such studies may help in the development of a potent and specific TFPI-2 KD1 molecule that specifically inhibits plasmin without targeting other proteases. Such a molecule could have a large pharmacologic impact specifically in preventing tumor metastasis, retinal degeneration, and degradation of collagen in the ECM.

Example VI

Inhibition of Angiogenesis by TFPI-2

Materials and Methods

A semi-quantitative assay for in vitro angiogenesis was utilized. Human umbilical vein endothelial cells (HUVEC, Clonetics) were maintained in 25 cm$^2$ flasks in EGM-2 media (Clonetics) supplemented with 2% fetal bovine serum, gentamicin, amphotericin-B, hEGF, hydrocortisone, VEGF, hFGF-B, R$^3$-IGF-1, ascorbic acid and heparin. For assay, a 48-well tissue culture plate was coated with 100 µl of ECMatrix™ (Chemicon) followed by incubation at 37° C. for 1 hour. Approximately 5×10$^4$ cells were then seeded onto the surface of the polymerized matrix. Varying concentrations of full-length human TFPI-2, diluted in EGM-2 media and filtered, were added to the wells and plate was placed in 37° C.-humidified $CO_2$ incubator. Each treatment was performed in duplicate wells. Separately, VEGF was used as a positive control. The 3-dimensional organization of cells was examined every hour under an inverted photomicroscope. The capillary tube branch point formation was counted in each well following 8 hours of incubation. For each concentration, eight randomly chosen areas under 250× magnified field were observed. The results are expressed as number of branching points (mean +SEM) and the differences between each mean value was tested by one way analysis of variance (ANOVA). Statistically p-value <0.05 was accepted.

To examine the effect of full-length human TFPI-2 on morphogenesis (capillary-like tube formation) of endothelial cells, HUVECs were seeded on the matrigel and treated with full-length human TFPI-2 (0.2 µM-5 µM).

Results

Figure 14:
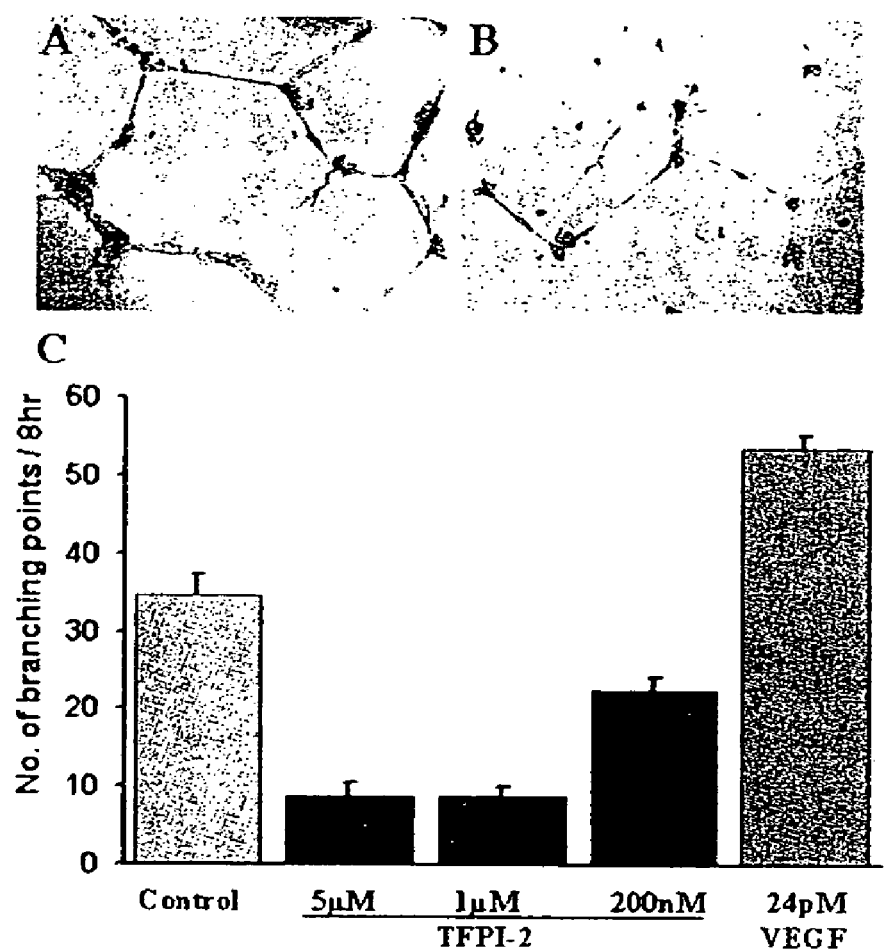
FIG. 14 shows the effect of TFPI-2 on endothelial cell capillary tube formation. A, 6 hour HUVEC tube formation in the absence of TFPI-2; B, 15 hour HUVEC tube formation in the presence of 5 µM TFPI-2; C, number of branch points formed in 8 hours in control endothelial cells (-TFPI-2) and endothelial cells treated with exogenous TFPI-2 or VEGF at the indicated concentrations.

Capillary-like tube formation, an indication of in-vitro angiogenesis, was well developed in control HUVECs after 6 hours (FIG. 14A) whereas with TFPI-2 (5 µM) treatment there was no complete tube formation even after overnight incubation (FIG. 14B). Additionally, TFPI-2 treatment significantly inhibited the capillary-like tube formation of HUVECs in a dose-dependent manner compared to controls (FIG. 14C). Addition of the pro-angiogenic agent, VEGF, yielded a significant increase in number of tube formation (FIG. 14C) with the first visible tube forming within 3 hours of incubation compared to approximately 4 hours in the control. Further, angiogenesis-related genes are modulated by full-length TFPI-2. As described in Example III, VEGF-C was down regulated 2.41 fold, VEGF-R1 (FLT1) was down regulated 2.24 fold and IL-8 another pro-angiogenic gene was down regulated 6.99 fold in human fibrosarcomas secreting wild-type human TFPI-2.

We have shown that hexahistidine-tagged KD1 and wild-type TFPI-2 inhibit angiogenesis. However, preliminary experiments have indicated that wild-type KD1 does not inhibit angiogenesis. Thus, we postulate that a positively charged amino acid sequence at either the N-terminus or the C-terminus facilitates this anti-angiogenic activity, perhaps by a charge-mediated targeting mechanism.

Example VII

Structural Differences Between Bovine Pancreatic Trypsin Inhibitor (Aprotinin) and Kunitz Domain 1 (KD1) of Human TFPI-2 in Binding to Plasmin: Designing an Improved KD1 Molecule for Therapeutic Use Bovine pancreatic trypsin inhibitor (BPTI) is a Kunitz-type serine protease inhibitor. It readily inhibits plasmin and is widely used in open heart surgery and recommended in orthopaedic surgery to minimize preoperative bleeding and administration of blood products (D. Taggart et al., *J Thorac Cardiovasc Surg* 126: 1087-94, 2003; A. Kokoszka et al., *J Bone Joint Surg Am* 87:1129-36, 2005). Recently, the plasminogen/plasmin system has also been implicated in development of rheumatoid arthritis (J. Li et al., *Am J Pathol* 166: 783-92, 2005; M. Judex et al., *Am J Pathol* 166: 645-647, 2005; H. Lijnen et al., *J Thromb Haemost* 1:35-45, 2005; G. Hilal et al., *Arthritis Rheum* 41:891-899, 1998; H. Ronday et al., *Br J Rheumatol* 36:9-15, 1997), as well as in bone remodeling and resorption (J. Novak et al., *J Bone Miner Res* 12:1035-1042, 1997; E. Daci et al., *J Bone Miner Res* 14:946-52, 1999; E. Daci et al. *J Miner Res* Bone 18:1167-76, 2003) and angiogenesis (H. Lijnen et al., *J Thromb Haemost* 1:35-45, 2005; P. Choong et al., *Clin Orthop Relat Res* 415:S46-S58, 2003 (Suppl); F. Castellino et al., *Thromb Haemost* 93:647-54, 2005).

Human tissue factor pathway inhibitor-2 (TFPI-2), also known as matrix serine protease inhibitor or placental protein 5, contains three Kunitz-type (similar to BPTI) domains in tandem with a short acidic N-terminus and very basic C-terminal tail (C. Sprecher et al., *Proc Natl Acad Sci USA* 91:3353-7, 1994; Y. Miyagi et al., *J Biochem* (Tokyo) 116: 939-42, 1994). A variety of cells, including keratinocytes, dermal fibroblasts, smooth muscle cells, syncytiotrophoblasts, synovioblasts, and endothelial cells synthesize and secrete TFPI-2 into the extracellular matrix (ECM) (C. Rao et al., *J Invest. Dermatol.* 104, 379-383, 1995; K. Udagawa et al., *Placenta* 19, 217, 223, 1998; T. Sugiyama et al., *FEBS Lett.* 517, 121-128, 2002; M. Iino et al., *Arterioscler. Thromb. Vasc. Biol.* 18, 40-46, 1998). TFPI-2 is found in three forms due to differences in glycosylation with $M_r$ 27,000, 30,000 and 32,000 (M. Iino et al., *Arterioscler. Thromb. Vasc. Biol.* 18, 40-46, 1998; C. Rao et al., *Arch. Biochem. Biophys.* 335, 45-52, 1996). The first Kunitz domain (KD1) of human TFPI-2 is homologous to BPTI and also inhibits plasmin (H. Chand et al., *J Biol Chem* 279:17500-17507, 2004). Although KD1 is specific for inhibiting plasmin, the other two Kunitz domains in TFPI-2 have no discernable inhibitory activity. The C-terminal basic tail, however, may anchor TFPI-2 to glycosaminoglycans in the ECM for localized inhibition of plasmin.

The crystal structure of BPTI (R. Huber et al., *J Mol Biol.* 89:73-101, 1974) and that of the KD1 (A. Schmidt et al., *J Biol Chem.* 280:27832-27838, 2005) with trypsin have been determined. The crystal structure of the proteinase domain of human plasmin has also been determined (X. Wang et al., *Science* 281, 1662-1665, 1998). Using these structures as templates, we have modeled the complexes of plasmin with BPTI, as well as plasmin and KD1, with a high degree of accuracy. The relative positions of the inhibitors and the proteinase domain of plasmin were maintained and minor adjustments were only made in the side chains. Hydrophobic/van der Waals, hydrogen bonds, and ionic interactions were observed between each proteinase-inhibitor complex. All of these interactions were taken into consideration in evaluating each inhibitor-proteinase complex, and it was assumed that all potential hydrogen bond donors and acceptors would participate in these interactions. Bulk solvent was excluded from the proteinase-inhibitor complex and, accordingly, it was anticipated that hydrogen bonds and ionic interactions that may play an important role in specificity could be accurately evaluated. The protocols for modeling these complexes have been described earlier (M. Bajaj et al., *Thromb. Haemost.* 86, 959-972, 2001).

Figure 15:
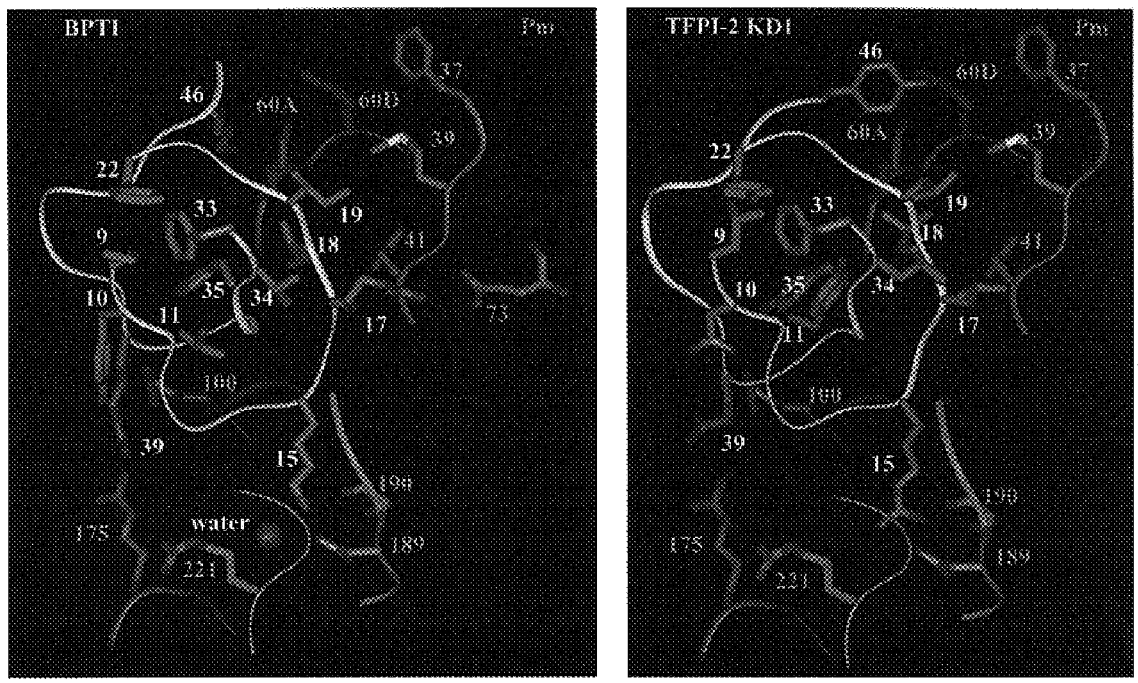
FIG. 15 shows A (upper panel), a sequence alignment for a portion of the amino acid sequences of BPTI and KD1 (using the numbering system in common use for BPTI, rather than the KD1 number system; addition of 9 to the sequence will result in KD1 numbering); as well graphical representations of the residues in B (left panel), BPTI, and C (right panel), KD1, that interact with plasmin. In the model (left and right panels), plasmin structure is depicted as cyan ribbons, and BPTI and KD1 structures are shown as yellow ribbons. On the left is the BPTI:plasmin complex and on the right is the KD1:plasmin complex. Residues 9, 11, 22, 33 and 35 both in the BPTI and KD1 form the hydrophobic core. The hydrophobic patch in BPTI, as well as in KD1, comprised of residues 17, 18, 19, and 34, is shown interacting with the hydrophobic patch in plasmin consisting of residues 37{583}, 39{585}, and 41 {587}. Glu39 of the acidic patch in KD1 interacts directly with Arg175 {719} and possibly through water molecules to Arg100 {644} and Arg221 {767} of the basic patch in plasmin; since in BPTI residue 39 is Arg, such interactions with plasmin are not possible. Tyr46 of KD1 interacts with Lys60A {607} and Arg60D {610} in plasmin; since residue 46 is Lys in BPTI, such interactions are not possible. Arg17 in BPTI interacts with Glu73 {623} in plasmin; since residue 17 is Leu in KD1, such interaction are not possible. Thr11 in BPTI hydrogen bonds with the side chain N of Gln192{738}; since residue 11 is Tyr in KD1, such interactions are not possible. Residue 192 is not shown in the figure. Also not shown is residue 20, which is Arg in both BPTI and KD1 that interacts with the Glu60 {606} in plasmin. The P1 residue 15 in BPTI is Lys that interacts with the side chain 0 of Ser190 {736} and Asp189 {735} through a water molecule is shown. The P1 residue 15 in KD1 is Arg that also interacts with Ser190 and Asp 189 in plasmin is shown. The numbering system used for plasmin is that of chymotrypsin. Where insertions occur, the chymotrypsin numbering is followed by a capital letter such as 60A and 60D. The numbers in braces represent plasminogen numbering. In the sequence alignment green represents hydrophobic, red represents acidic, blue represents basic, and purple represents polar residues.

FIG. 15 shows (A) a sequence alignment for a portion of the amino acid sequences of BPTI and KD1, along with the residues in (B) BPTI and (C) KD1 that interact with plasmin. Note that the numbering system used in FIG. 15 is the BPTI numbering system, not the KD1 numbering system. For example, Cys23 in KD1 is the equivalent of Cys14 in BPTI, and Arg24 in KD1 is at the same position as Lys15 in BPTI. From the models presented in FIG. 1, changing Leu17 to Arg, and Tyr11 to Thr in KD1 should yield a molecule that has significantly higher affinity and specificity towards human plasmin. Changing Tyr46 to Glu and Asp 10 to Glu are also expected to increase affinity and specificity towards inhibiting plasmin. On the other hand, changing Glu39 to Arg and Tyr46 to Lys should result in substantial loss of affinity of KD1 for human plasmin. Systematically, changing those residues that result in gain of function such as modified KD1 with Thr11 and Arg17 should yield a molecule that is more potent than BPTI and native KD1. Such a molecule should also be less immunogenic than BPTI. Interestingly, BPTI-induced hypersensitivity reaction occurs in about 1.2 to 2.7 percent of patients re-exposed to aprotinin (W. Beierlein et al., Ann Thorac Surg. 79:741-748, 2005). Of these reactions, 50 percent are life threatening with a 9 percent fatality rate (W. Beierlein et al., Ann Thorac Surg. 79:741-748, 2005). Obviously, a human molecule that is selectively engineered to increase its inhibitory potency is highly desirable. Such a molecule is also expected to be less immunogenic than BPTI. It is further anticipated that a construct containing the KD1 with enhanced inhibitory activity and the basic tail of TFPI-2 at its C-terminus would result in a molecule with an increased half-life in the extracellular matrix.

Example VIII

Inhibition of Human Plasmin Amidolytic Activity by TFPI-2 KD1 Mutants

Site-directed Mutants

Single and double mutants of KD1 were prepared and purified substantially as described in Examples I and II.

Human Plasmin Inhibition Assay

The plasmin inhibition assays was performed as described by Petersen et al., 1996 (Petersen et al., *Biochemistry* 35: 266-272, 1996). Briefly, plasmin [30 nM] was incubated with various concentrations of inhibitors preparations for 15 minutes at 37° C. in a microtitration plate. The chromogenic substrate S-2251 [660 μM] was then added and the residual amidolytic activity was measured at $A_{405}$ nm using $UV_{max}$ kinetic microplate reader (Molecular Devices, Sunnyvale, Calif., USA). TBS/BSA (0.1%) was used as a diluent. Inhibitor concentrations were corrected for light scattering ($A_{320}$) using $A_{280}$(corrected)=$A_{280}$ (observed)−1.695×$A_{320}$ (observed)

Inhibition Kinetics

The apparent inhibition constant, $K_i'$ was determined using the non-linear regression data analysis program Ultrafitfv3.0 (Biosoft, USA)

$$v_i=v_0[\sqrt{(K_i'+[I]_0+[E]_0)^2-4[I]_0[E]_0}-(K_i'+[I]_0-[E]_0)]/2[E]_0$$

$K_m$ is the Michaelis constant for the enzyme-substrate pair, and $K_i'$ is the apparent inhibition constant. The actual $K_i$ values were obtained by correcting for the effect of substrate according to the following equation:

$$K_i=K_i'/(1+[S]/K_m)$$

According to the manufacturer's data sheet, the Michaelis constant ($K_m$) for plasmin towards its substrate S-2251 is 300 μM.

Results

In an initial experiment, wherein the concentration of plasmin (pn)=30 nM; total volume, $V_T$=300 uL; and the concentration of the chromogenic substrate, S-2251=660 μM, the following results were obtained for the double mutant R24K/L26R in comparison with BPTI:

| | $K_i'$ | $K_i$ ($K'_i$/3.2) |
|---|---|---|
| BPTI | 0.97 | 0.3 |
| R24K/L26R KD1 | 7.4 | 2.2 |

In an experiment comparing the single R24K KD1 mutant and double mutant R24K/L26R KD1, wherein Pn=30 nM; $V_T$=300 uL, the following results were obtained:

| | $K_i'$ | $K_i$($K_i'$/3.2) |
|---|---|---|
| BPTI | 2.6 | 0.8 |
| R24K/L26R KD1 | 3.4 | 1.06 |
| R24K KD1 | 4.26 | 1.33 |
| KD1 | 31 | 9.7 |

In another experiment, wherein Pn=30 nM; $V_T$=300 uL; S-2251=660 μM, the following results were obtained:

| | $K_i'$ | $K_i$($K_i'$/3.2) |
|---|---|---|
| BPTI | 1.16 | 0.36 |
| R24K/L26R KD1 | 4.0 | 1.25 |
| R24K KD1 | 3.27 | 1.02 |
| KD1 | 20.5 | 6.4 |

In yet another experiment, wherein Pn=10 nM; $V_T$=100 uL; S-2251=1000 μM, and incubation time=30 mts+CaCl2 (20 mM), the following results were obtained:

| | $K_i'$ | $K_i$ ($K_i'$/4.33) |
|---|---|---|
| BPTI | 1.5 | 0.35 |
| R24K/L26R KD1 | 6.54 | 1.5 |
| R24K KD1 | 20.08 | 4.6 |
| KD1 | 32.6 | 7.5 |

In yet another experiment, wherein Pn=30 nM; $V_T$=300 uL; S-2251=660 μM, incubation time=30 mts and diluent: TBS/Tween-20 (0.05%), the following results were obtained:

|  | $K_i'$ | $K_i(K_i'/3.2)$ |
|---|---|---|
| BPTI | 0.75 | 0.23 |
| R24K/L26R KD1 | 2.0 | 0.625 |
| R24K KD1 | 3.52 | 1.1 |
| KD1 | 16.92 | 5.3 |

When the single mutant L26R KD1 was compared to the other site-directed mutants, it was observed that the L26R mutant exhibited more inhibitory activity than the wild-type KD1, but less inhibitory activity than the R24K/L26R double mutant.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An isolated polypeptide comprising the primary structure of the wild-type KD 1 domain of human tissue factor pathway inhibitor-2 (TFPI-2) of SEQ ID NO: 2 or a biologically active subunit thereof, wherein the biological activity is serine protease inhibition, with the proviso that said polypeptide or a biologically active subunit thereof includes a lysine instead of arginine at position 24 and at least one of the following additional changes with respect to the wild-type KD 1 primary structure selected from the group consisting of:

an arginine instead of a leucine at position 26;
a threonine instead of a tyrosine at position 20;
a glutamate or a tyrosine instead of an aspartate at position 19; and
a glutamate or a lysine instead of a tyro sine at position 55;

wherein the amino acid numbering is as defined for the wild-type KD 1 amino acid sequence.

2. The isolated polypeptide of claim 1, as set forth in SEQ ID NO:3 modified to include at least one of the following additional changes with respect to the wild-type KD 1 primary structure selected from the group consisting of:

an arginine instead of a leucine at position 26;
a threonine instead of a tyrosine at position 20;
a glutamate or a tyrosine instead of an aspartate at position 19; and
a glutamate or a lysine instead of a tyrosine at position 55;

wherein the amino acid numbering is as defined for the wild-type KD1 amino acid sequence.

3. The isolated polypeptide of claim 1 wherein the biologically active subunit of KD 1 is characterized by deletions of 1, 2, 3, 4, 5, 6, 7, 8, 9, or 10 amino acid residues at either or both of the amino-terminal or carboxy-terminal end relative to the wild-type KD 1 sequence.

4. The isolated polypeptide of claim 1 comprising a primary structure that is similar to the primary structure of the wild-type KD1 domain of TFPI-2 of SEQ ID NO: 2, or a biologically active subunit thereof, wherein the biological activity is serine protease inhibition, with the proviso that said polypeptide includes at least one conservative amino acid substitution relative to the primary structure of the wild-type KD1 domain of TFPI-2, and with the further proviso that said polypeptide includes a lysine instead of arginine at position 24 and at least one of the following additional changes with respect to the wild-type KD 1 primary structure selected from the group consisting of:

an arginine instead of a leucine at position 26;
a threonine instead of a tyrosine at position 20;
a glutamate or a tyrosine instead of an aspartate at position 19; and
a glutamate or a lysine instead of a tyrosine at position 55;

wherein the amino acid numbering is as defined for the wild-type KD1 amino acid sequence.

5. The isolated polypeptide of claim 1 wherein the polypeptide exhibits inhibitory activity against a serine protease that degrades fibrinogen.

6. An isolated polypeptide comprising the polypeptide of claim 1; and
a multiple positively charged amino acid sequence disposed at either or both of the N-terminal or C-terminal end of the polypeptide.

7. The isolated polypeptide of claim 6 wherein the multiple positively charged amino acid sequence comprises an amino acid sequence from the C-terminus of wild-type TFPI-2.

8. The isolated polypeptide of claim 7 wherein the multiple positively charged amino acid sequence comprises amino acids 192 through 211 of SEQ ID NO: 1.

9. A pharmaceutical composition comprising:
the isolated polypeptide of claim 1; and
a pharmaceutically acceptable carrier.

10. A method for treating a subject for a condition treatable by aprotinin, said method
comprising administering to the subject an effective amount of the polypeptide of claim 1.

11. The method of claim 10 wherein the condition treatable by aprotinin is associated
with surgery or cardiovascular disease.

12. A method for treating a subject afflicted with allergies or asthma, said method
comprising administering to a subject an effective amount of the polypeptide of claim 1.

13. A method for treating a subject afflicted with cancer or a precancerous condition,
said method comprising administering to a subject an effective amount of the polypeptide of claim 1.

14. A method for treating a subject afflicted with an influenza infection, said method comprising administering to a subject an effective amount of the polypeptide of claim 1.

15. A method for treating a subject in need of surgery comprising administering an effective amount of the polypeptide of claim 1 to the subject before, during and/or after surgery.

16. The method of claim 15 wherein the surgery is performed on a component of the cardiovascular system.

17. The method of claim 15 wherein the surgery is orthopedic surgery.

18. A method for treating a subject in need of inhibition of plasmin activity, said method comprising administering to a subject an effective amount of the polypeptide of claim 1.

19. The method of claim 18 wherein the subject is undergoing bone remodeling.

20. The method of claim 18 wherein the subject is afflicted with hemophilia.

21. The method of claim 18 wherein the subject is afflicted with systemic inflammatory response syndrome (SIRS).

22. A method for inhibiting at least one activity of plasmin comprising contacting plasmin with an effective amount of the polypeptide of claim 1.

23. The isolated polypeptide of claim 1 wherein a ligand is attached to the polypeptide.

\* \* \* \* \*

UNITED STATES PATENT AND TRADEMARK OFFICE
CERTIFICATE OF CORRECTION

PATENT NO. : 7,585,842 B2  Page 1 of 1
APPLICATION NO. : 11/646776
DATED : September 8, 2009
INVENTOR(S) : Kisiel et al.

It is certified that error appears in the above-identified patent and that said Letters Patent is hereby corrected as shown below:

On the title page Item (73) Assignee: correct the listing of the assignee from "The Reagents of the University of California, Oakland, CA (US)" to read --The Regents of the University of California, Oakland, CA (US)--

Signed and Sealed this

Twenty-ninth Day of December, 2009

David J. Kappos
*Director of the United States Patent and Trademark Office*

SEQUENCE LISTING

<160> NUMBER OF SEQ ID NOS: 30

<210> SEQ ID NO 1
<211> LENGTH: 213
<212> TYPE: PRT
<213> ORGANISM: Homo sapiens

<400> SEQUENCE: 1

Asp Ala Ala Gln Glu Pro Thr Gly Asn Asn Ala Glu Ile Cys Leu Leu
1               5                   10                  15

Pro Leu Asp Tyr Gly Pro Cys Arg Ala Leu Leu Leu Arg Tyr Tyr Tyr
            20                  25                  30

Asp Arg Tyr Thr Gln Ser Cys Arg Gln Phe Leu Tyr Gly Gly Cys Glu
        35                  40                  45

Gly Asn Ala Asn Asn Phe Tyr Thr Trp Glu Ala Cys Asp Asp Ala Cys
    50                  55                  60

Trp Arg Ile Glu Lys Val Pro Lys Val Cys Arg Leu Gln Val Ser Val
65                  70                  75                  80

Asp Asp Gln Cys Glu Gly Ser Thr Glu Lys Tyr Phe Phe Asn Leu Ser
                85                  90                  95

Ser Met Thr Cys Glu Lys Phe Phe Ser Gly Gly Cys His Arg Asn Arg
            100                 105                 110

Ile Glu Asn Arg Phe Pro Asp Glu Ala Thr Cys Met Gly Phe Cys Ala
        115                 120                 125

Pro Lys Lys Ile Pro Ser Phe Cys Tyr Ser Pro Lys Asp Glu Gly Leu
    130                 135                 140

Cys Ser Ala Asn Val Thr Arg Tyr Tyr Phe Asn Pro Arg Tyr Arg Thr
145                 150                 155                 160

Cys Asp Ala Phe Thr Tyr Thr Gly Cys Gly Gly Asn Asp Asn Asn Phe
                165                 170                 175

Val Ser Arg Glu Asp Cys Lys Arg Ala Cys Ala Lys Ala Leu Lys Lys
            180                 185                 190

Lys Lys Lys Met Pro Lys Leu Arg Phe Ala Ser Arg Ile Arg Lys Ile
        195                 200                 205

Arg Lys Lys Gln Phe
    210

<210> SEQ ID NO 2
<211> LENGTH: 73
<212> TYPE: PRT

-continued

```
<213> ORGANISM: Homo sapiens

<400> SEQUENCE: 2

Asp Ala Ala Gln Glu Pro Thr Gly Asn Asn Ala Glu Ile Cys Leu Leu
1               5                   10                  15

Pro Leu Asp Tyr Gly Pro Cys Arg Ala Leu Leu Leu Arg Tyr Tyr Tyr
            20                  25                  30

Asp Arg Tyr Thr Gln Ser Cys Arg Gln Phe Leu Tyr Gly Gly Cys Glu
        35                  40                  45

Gly Asn Ala Asn Asn Phe Tyr Thr Trp Glu Ala Cys Asp Asp Ala Cys
    50                  55                  60

Trp Arg Ile Glu Lys Val Pro Lys Val
65                  70

<210> SEQ ID NO 3
<211> LENGTH: 73
<212> TYPE: PRT
<213> ORGANISM: Artificial
<220> FEATURE:
<223> OTHER INFORMATION: mutated active domain

<400> SEQUENCE: 3

Asp Ala Ala Gln Glu Pro Thr Gly Asn Asn Ala Glu Ile Cys Leu Leu
1               5                   10                  15

Pro Leu Asp Tyr Gly Pro Cys Lys Ala Leu Leu Leu Arg Tyr Tyr Tyr
            20                  25                  30

Asp Arg Tyr Thr Gln Ser Cys Arg Gln Phe Leu Tyr Gly Gly Cys Glu
        35                  40                  45

Gly Asn Ala Asn Asn Phe Tyr Thr Trp Glu Ala Cys Asp Asp Ala Cys
    50                  55                  60

Trp Arg Ile Glu Lys Val Pro Lys Val
65                  70

<210> SEQ ID NO 4
<211> LENGTH: 11
<212> TYPE: PRT
<213> ORGANISM: Reactive Site Region

<400> SEQUENCE: 4

Tyr Thr Gly Pro Cys Lys Ala Arg Ile Ile Arg
1               5                   10

<210> SEQ ID NO 5
<211> LENGTH: 11
<212> TYPE: PRT
<213> ORGANISM: Reactive Site Region

<400> SEQUENCE: 5

Glu Thr Gly Pro Cys Arg Ala Met Ile Ile Arg
1               5                   10

<210> SEQ ID NO 6
<211> LENGTH: 11
<212> TYPE: PRT
<213> ORGANISM: Reactive Site Region

<400> SEQUENCE: 6

Met Thr Gly Pro Cys Arg Ala Val Met Pro Arg
1               5                   10

<210> SEQ ID NO 7
```

```
<211> LENGTH: 11
<212> TYPE: PRT
<213> ORGANISM: Reactive Site Region

<400> SEQUENCE: 7

Asp Asp Gly Pro Cys Lys Ala Ile Met Lys Arg
1               5                   10

<210> SEQ ID NO 8
<211> LENGTH: 11
<212> TYPE: PRT
<213> ORGANISM: Reactive Site Region

<400> SEQUENCE: 8

Asp Pro Gly Ile Cys Arg Gly Tyr Ile Thr Arg
1               5                   10

<210> SEQ ID NO 9
<211> LENGTH: 11
<212> TYPE: PRT
<213> ORGANISM: Reactive Site Region

<400> SEQUENCE: 9

Asp Leu Gly Leu Cys Arg Ala Asn Glu Asn Arg
1               5                   10

<210> SEQ ID NO 10
<211> LENGTH: 11
<212> TYPE: PRT
<213> ORGANISM: Reactive Site Region

<400> SEQUENCE: 10

Asp Tyr Gly Pro Cys Arg Ala Leu Leu Leu Arg
1               5                   10

<210> SEQ ID NO 11
<211> LENGTH: 11
<212> TYPE: PRT
<213> ORGANISM: Reactive Site Region

<400> SEQUENCE: 11

Val Asp Asp Gln Cys Glu Gly Ser Thr Glu Lys
1               5                   10

<210> SEQ ID NO 12
<211> LENGTH: 11
<212> TYPE: PRT
<213> ORGANISM: Reactive Site Region

<400> SEQUENCE: 12

Asp Glu Gly Leu Cys Ser Ala Asn Val Thr Arg
1               5                   10

<210> SEQ ID NO 13
<211> LENGTH: 11
<212> TYPE: PRT
<213> ORGANISM: Reactive Site Region

<400> SEQUENCE: 13

Lys Val Gly Arg Cys Arg Gly Ser Phe Pro Arg
1               5                   10

<210> SEQ ID NO 14
<211> LENGTH: 11
<212> TYPE: PRT
```

<210> SEQ ID NO 14
<211> LENGTH: 11
<212> TYPE: PRT
<213> ORGANISM: Reactive Site Region

<400> SEQUENCE: 14

Asp Thr Gly Leu Cys Lys Glu Ser Ile Pro Arg
1               5                   10

<210> SEQ ID NO 15
<211> LENGTH: 11
<212> TYPE: PRT
<213> ORGANISM: Reactive Site Region

<400> SEQUENCE: 15

Val Val Gly Arg Cys Arg Ala Ser Met Pro Arg
1               5                   10

<210> SEQ ID NO 16
<211> LENGTH: 11
<212> TYPE: PRT
<213> ORGANISM: Reactive Site Region

<400> SEQUENCE: 16

Val Thr Gly Pro Cys Arg Ala Ser Phe Pro Arg
1               5                   10

<210> SEQ ID NO 17
<211> LENGTH: 11
<212> TYPE: PRT
<213> ORGANISM: Reactive Site Region

<400> SEQUENCE: 17

Ser Ala Gly Pro Cys Met Gly Met Thr Ser Arg
1               5                   10

<210> SEQ ID NO 18
<211> LENGTH: 11
<212> TYPE: PRT
<213> ORGANISM: Reactive Site Region

<400> SEQUENCE: 18

Tyr Thr Gly Pro Cys Lys Ala Arg Met Ile Lys
1               5                   10

<210> SEQ ID NO 19
<211> LENGTH: 11
<212> TYPE: PRT
<213> ORGANISM: Reactive Site Region

<400> SEQUENCE: 19

Tyr Thr Gly Pro Cys Arg Ala His Phe Ile Arg
1               5                   10

<210> SEQ ID NO 20
<211> LENGTH: 11
<212> TYPE: PRT
<213> ORGANISM: Reactive Site Region

<400> SEQUENCE: 20

Lys Thr Gly Pro Cys Lys Ala Ala Phe Gln Arg
1               5                   10

<210> SEQ ID NO 21
<211> LENGTH: 11
<212> TYPE: PRT
<213> ORGANISM: Reactive Site Region

```
<400> SEQUENCE: 21

Asp Val Gly Arg Cys Arg Ala Ser His Pro Arg
1               5                   10

<210> SEQ ID NO 22
<211> LENGTH: 73
<212> TYPE: PRT
<213> ORGANISM: Artificial
<220> FEATURE:
<223> OTHER INFORMATION: mutated active domain

<400> SEQUENCE: 22

Asp Ala Ala Gln Glu Pro Thr Gly Asn Asn Ala Glu Ile Cys Leu Leu
1               5                   10                  15

Pro Leu Asp Tyr Gly Pro Cys Arg Ala Leu Leu Leu Arg Tyr Tyr Tyr
                20                  25                  30

Asp Arg Tyr Thr Gln Ser Cys Arg Gln Phe Leu Tyr Gly Gly Cys Glu
            35                  40                  45

Gly Asn Ala Asn Asn Phe Tyr Thr Trp Glu Ala Cys Asp Asp Ala Cys
    50                  55                  60

Trp Arg Ile Glu Lys Val Pro Lys Val
65                  70

<210> SEQ ID NO 23
<211> LENGTH: 24
<212> TYPE: DNA
<213> ORGANISM: Artificial
<220> FEATURE:
<223> OTHER INFORMATION: primer sequence

<400> SEQUENCE: 23
gctattacct tcttattatt tacc                                           24

<210> SEQ ID NO 24
<211> LENGTH: 20
<212> TYPE: DNA
<213> ORGANISM: Artificial
<220> FEATURE:
<223> OTHER INFORMATION: primer sequence

<400> SEQUENCE: 24
gtgcgatgag taggggaagg                                                20

<210> SEQ ID NO 25
<211> LENGTH: 20
<212> TYPE: DNA
<213> ORGANISM: Artificial
<220> FEATURE:
<223> OTHER INFORMATION: primer sequence

<400> SEQUENCE: 25
taatacgact cactataggg                                                20

<210> SEQ ID NO 26
<211> LENGTH: 29
<212> TYPE: DNA
<213> ORGANISM: Artificial
<220> FEATURE:
<223> OTHER INFORMATION: primer sequence

<400> SEQUENCE: 26
gcctcgagtt aaaattgctt cttccgata                                      29
```

-continued

```
<210> SEQ ID NO 27
<211> LENGTH: 19
<212> TYPE: DNA
<213> ORGANISM: Artificial
<220> FEATURE:
<223> OTHER INFORMATION: primer sequence

<400> SEQUENCE: 27
ttactgctgt acctccacc                                                19

<210> SEQ ID NO 28
<211> LENGTH: 19
<212> TYPE: DNA
<213> ORGANISM: Artificial
<220> FEATURE:
<223> OTHER INFORMATION: primer sequence

<400> SEQUENCE: 28
acaggacggc ttgaagatg                                                19

<210> SEQ ID NO 29
<211> LENGTH: 18
<212> TYPE: DNA
<213> ORGANISM: Artificial
<220> FEATURE:
<223> OTHER INFORMATION: primer sequence

<400> SEQUENCE: 29
aacgacccct tcattgac                                                 18

<210> SEQ ID NO 30
<211> LENGTH: 19
<212> TYPE: DNA
<213> ORGANISM: Artificial
<220> FEATURE:
<223> OTHER INFORMATION: primer sequence

<400> SEQUENCE: 30
tccacgacat actcagcac                                                19
```